US005891438A

United States Patent [19]

Silverman

[11] Patent Number: 5,891,438
[45] Date of Patent: Apr. 6, 1999

[54] METHOD FOR STIMULATING PRODUCTION OF VARIABLE REGION GENE FAMILY RESTRICTED ANTIBODIES THROUGH B-CELL SUPERANTIGEN VACCINATION

[75] Inventor: Gregg J. Silverman, Encinitas, Calif.

[73] Assignee: The Regents of the University of California, Oakland, Calif.

[21] Appl. No.: 428,197

[22] PCT Filed: Oct. 29, 1993

[86] PCT No.: PCT/US93/10555

§ 371 Date: Jul. 14, 1995

§ 102(e) Date: Jul. 14, 1995

[87] PCT Pub. No.: WO94/09818

PCT Pub. Date: May 11, 1994

Related U.S. Application Data

[63] Continuation-in-part of Ser. No. 969,936, Oct. 30, 1992, abandoned.

[51] Int. Cl.[6] .......................... A61K 39/00; A61K 38/00; A01N 37/18; A01N 43/04
[52] U.S. Cl. .................................... 424/185.1; 424/203.1; 424/234.1; 514/2; 514/8; 514/12; 514/23; 514/54; 530/300; 530/324
[58] Field of Search ............................ 424/130.1, 184.1, 424/201.1, 203.1, 185.1, 234.1; 514/2, 8, 12, 23, 54; 530/300, 324

[56] References Cited

PUBLICATIONS

Shuttleworth et al (Gene, 1987, 58:283–295).

Mayforth (Designing Antibodies, Academic Press, 993, NY p. 77.

Silverman, "Huamn Antibody Responses to Bacterial Antigens: Studies of a Model Conventional Antigen And a Proposed Model B Cell Superantigen." *Intern. Rev. Immunol.* vol. 9, 1992, pp. 57–78.

Moks, et al. . "Staphylococcal protein A consists of five IgG–binding domains," *Eur. J. Biochem.* 156, 637–643 (1986).

Schroeder, et al., "Sequence Analysis of Two Human Monoclonal Antibodies With Specificity for Type 3 Pneumococcal Polysaccharide (PPS–3)," *Mechanisms of Antibody Diversity* (1656–1660).

Tsai, et al., "Measurements of lipopolysaccharide (endotoxin) in meningococcal protein and polysaccharide preparations for vaccine usage," *Journal of Biological Standardization* (1989) 17:249–258.

Allison, et al., "Immunological Adjuvants: Desirable Properties and Side–Effects," *Molecular Immunology*, vol. 28, No. 3, pp. 279–284, 1991.

Peeter, et al., "Pneumococcal conjugate vaccines," *Immunology Letters*, 30 (1991) 267–274.

Verheul, et al., "Modulation of the Immune Response to Pneumococcal Type 14 Capsular Polysaccharide–Protein Conjugates by the Adjuvant Quil A . . .." *Infection and Immnity*, Apr. 1989, pp. 1078–1083.

Silverman, et al., "Variable Region Diversity in Human Circulating Antibodies Specific for the Capsula Polysaccharide of *Haemophilus influenzae*," *J. Clin. Invest.* vol. 88., Sep. 1991, 911–920.

Adderson, et al., "Restricted Ig H Chain V Gene Usage in the Human Antibody Response to *Haemophilus influenzae* Type b Capsular Polysaccharide," *Journal of Immunology*, vol. 147, 1667–1674, No. 5, Sep. 1, 1991.

Eliasson, et al., "Structural and Functional Analysis of the Human IgG–Fab Receptor Activity of Streptococcal Protein G," *Molecular Immunology*, vol. 28, No. 10, pp. 1055–1062, 1991.

Donnellt, et al., "Imunogenicity of a *Haemophilus influenzae* Polysaccharide–*Neisseria meningitidis* Outer Membrane Protein Complex Conjugate Vaccine," *Journal of Immunology*, vol. 145, 3071–3079, No. 9, Nov. 1, 1990.

Bouvet, et al., "Non–immune VH–binding Specificity of Human Protein Fv," *Scand. J. Immunol.* 33:381–386, 1991.

Seppala, et al., "Mouse Ig Coded by $V_H$ Families S107 or J606 Bind to Protein A[1]," *Journal of Immunology*, vol. 145, 2989–2993, No. 9, Nov. 1, 1990.

Lowenadler, et al., "Production of specific antibodies against protein A fusion proteins," Kabigen AB, Dept. of Biochemistry and Biotechnology, IRL Press Limited, Oxford, England, pp. 2393–2398.

Sasso, et al., "Human IgM Molecules that Bind Staphylococcal Protein A Contain $V_H$III H Chains," *Journal of Immunology*, vol. 142, 2778–2783, No. 8, Apr. 18, 1989.

Pascual, et al., "B–cell superantigens?", *Immunology*, vol. 1, No. 5, 1991.

(List continued on next page.)

*Primary Examiner*—Lila Feisee
*Assistant Examiner*—Susan Ungar
*Attorney, Agent, or Firm*—Fish & Richardson P.C.

[57] ABSTRACT

Criteria for identifying potential B cell superantigens are disclosed, together with a method for determining whether these candidate antigens have B cell superantigenic activity. Methods for constructing and using a vaccine including B cell superantigens are also disclosed. Identification is based on characterizing the structure of Ig binding sites which interact with the candidate antigen assessment of Ig V region diversity on binding of candidate and conventional antigens, confirmation of sAg activity in interactions between candidate antigens and whole cells, confirmation of whether the candidate antigen induces B cell mitogenesis, determination of the earliest point in B cell development where cellular co-factors are required for sAg activity and, for reference, determination of V region usage in responder populations. Once a B cell superantigen is characterized, it is purified and conjugated by chemical means to a polysaccharide or glycoprotein component from a microbial capsule, cell wall, envelope or other component preferably using components which stimulate production of antibodies with the same V region restriction as antibodies whose production is stimulated by the B cell superantigen.

3 Claims, 12 Drawing Sheets

OTHER PUBLICATIONS

Berberian, et al., "Immunoglubin $V_H3$ Gene Products: Natural Ligands for HIV gp120," *Science,* vol. 261, 17 Sep. 1993.

Goni, et al., "Sequence Similarities and Cross–Idiotypic Specificity of L Chains Among Human Monoclonal IgMk With Anti–y–Globulin Activity," *Journal of Immunology,* vol. 135, No. 6, Dec. 1985, pp. 4073–4079.

Taylor, et al., "T–Cell Modulation of the Antibody Response to Bacterial Polysaccharide Antigens," *Infection and Immunity,* vol. 57, Jan. 1989, pp. 180–185.

Sasso, et al., "Human IgA and IgG F(ab')$_2$ That Bind to Staphylococcal Protein A Belong to the $V_H$III Subgroup," *Journal of Immunology,* vol. 147, 1877–1883, No. 6, Sep. 15, 1991.

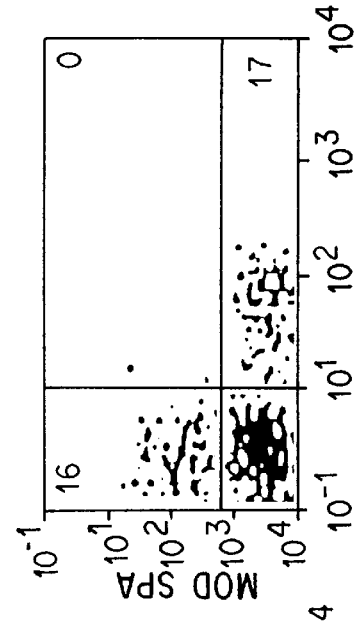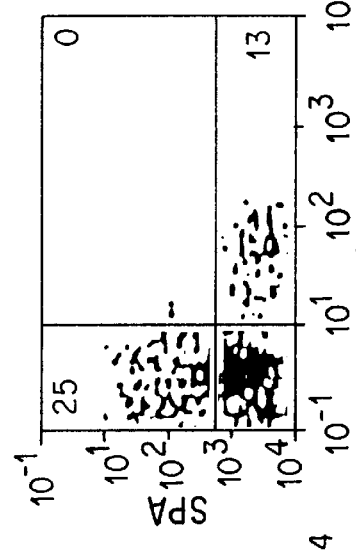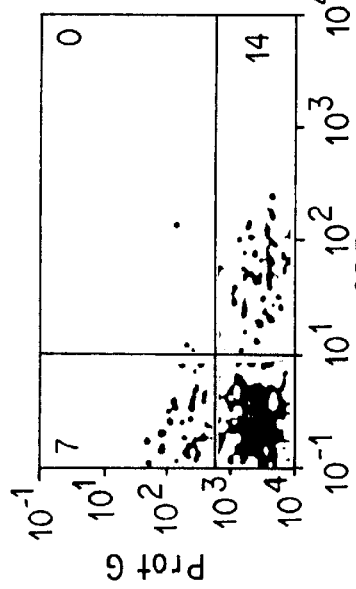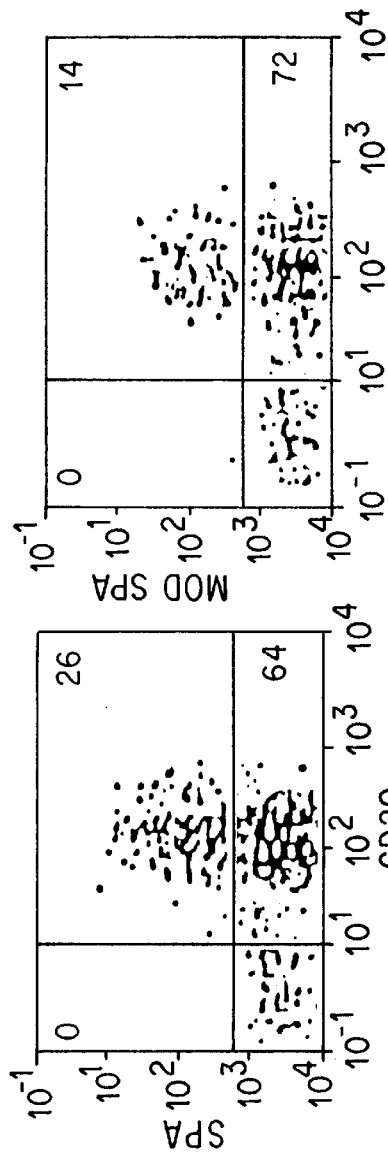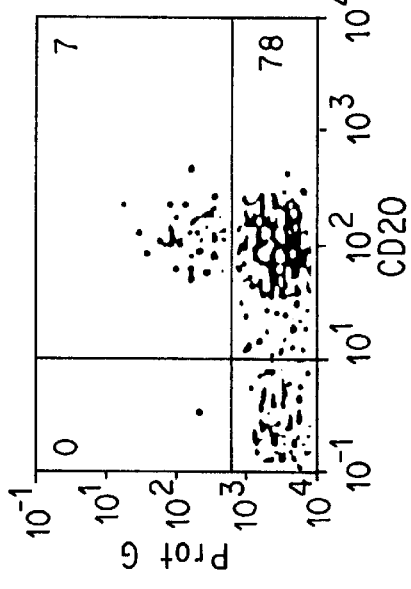

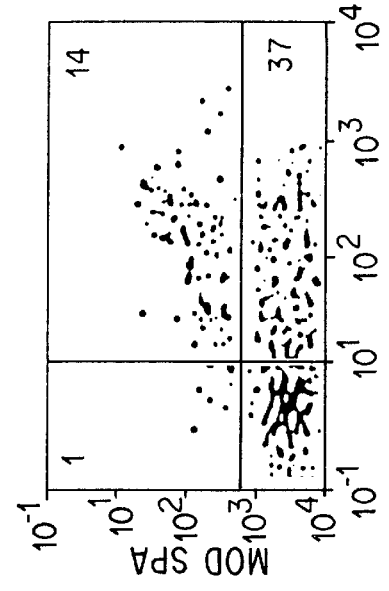
FIG. 4G
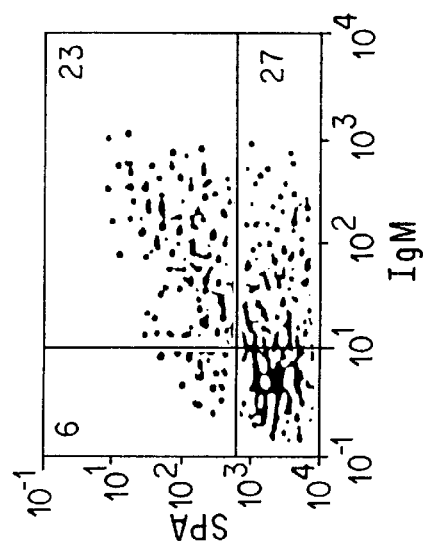
FIG. 4H
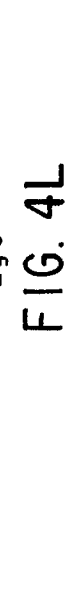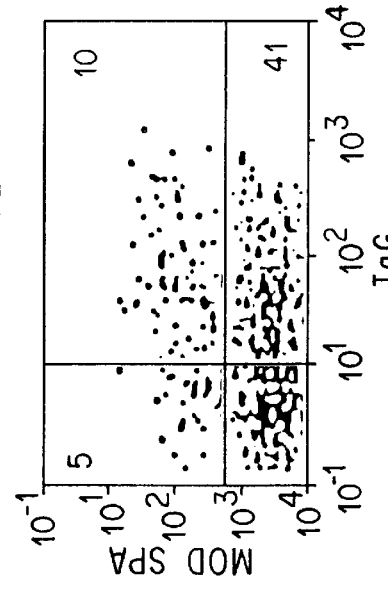
FIG. 4I
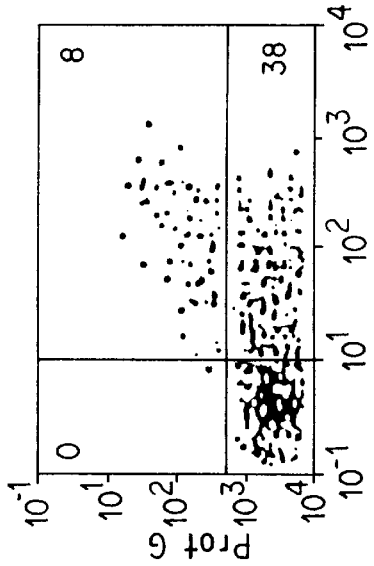
FIG. 4J
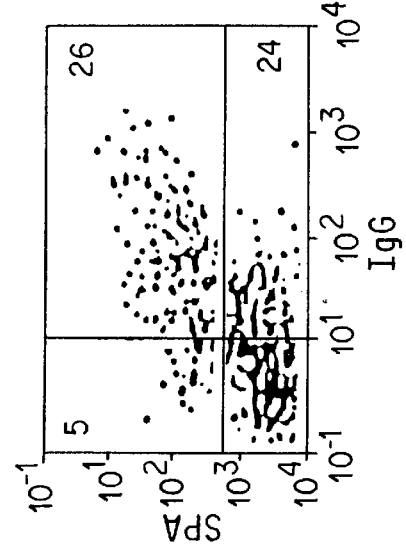
FIG. 4K
FIG. 4L

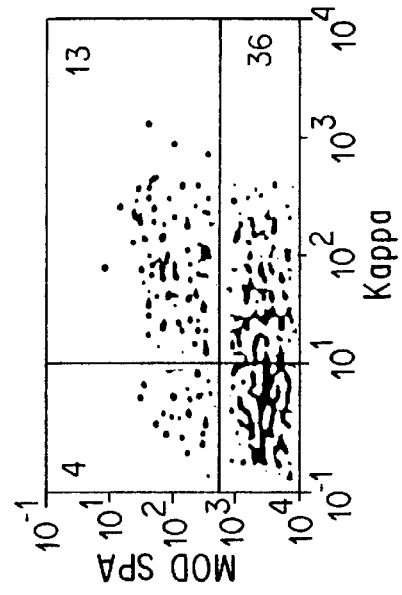
FIG. 4M
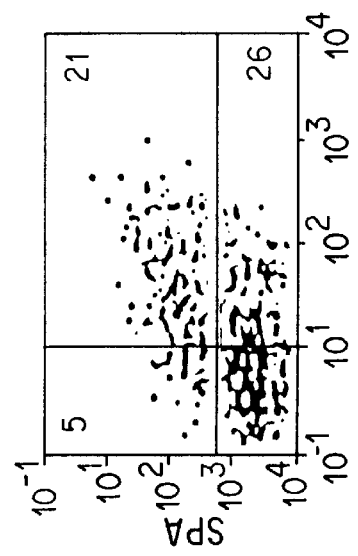
FIG. 4N
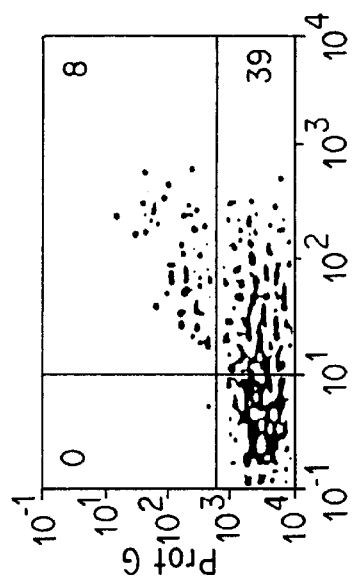
FIG. 4O
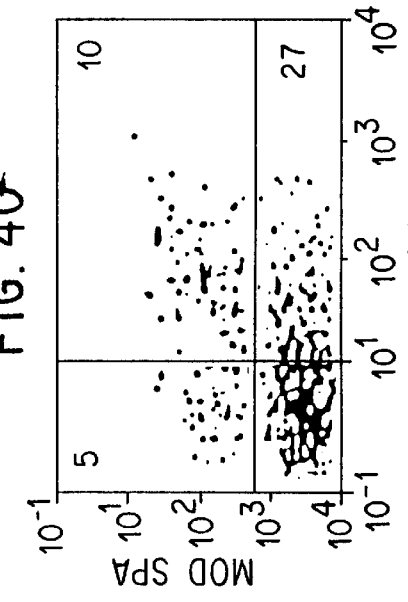
FIG. 4P
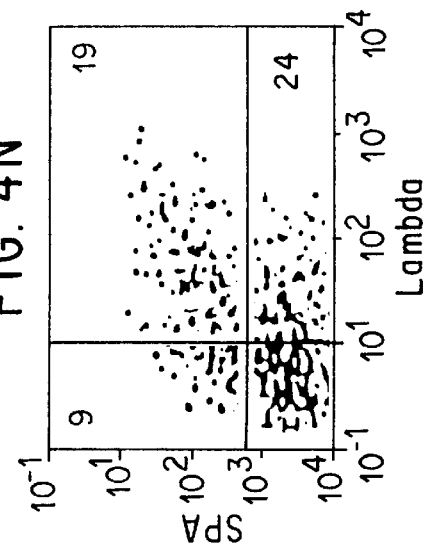
FIG. 4Q
FIG. 4R

$V_H$ Diversity of Post-Immunization Antibodies Antibodies to C Polysaccharide

| SUBJECT | $V_H1$ | $V_H4$ | $V_H3$ | 20PI/9-1-assoc | | 30PI/VH26-assoc* | |
|---|---|---|---|---|---|---|---|
| | | | | VH3-HV2a* | VH3-FR3a | VH3-HV2b | |
| 1. 06 | – | – | ++++ | ++ | + | – | |
| 2. 05 | – | ++++ | ++++ | +++ | ++ | – | |
| 3. 16 | – | – | ++ | – | – | – | |
| 4. 20 | + | + | ++++ | + | + | – | |
| 5. 17 | – | – | ++++ | ++++ | +++ | + | |
| 6. 07 | – | – | +++ | ++++ | ++ | – | |
| 7. 10 | – | – | ++++ | – | ++ | – | |
| 8. 15 | – | – | ++++ | ++ | ++ | – | |
| 9. 11 | – | – | ++ | ++ | ++ | + | |
| 10. 12 | ++++ | +++ | ++++ | ++ | ++ | – | |
| 11. 08 | – | + | ++++ | +++ | ++ | – | |
| 12. 18 | – | +++ | ++++ | – | ++++ | +++ | |
| 13. 13 | +++ | + | ++++ | ++++ | ++++ | – | |
| 14. 03 | +++ | – | +++ | – | ++ | – | |
| | 4 | 7 | 14 | 10 | 13 | 3 | |

FIG. 5

V_H Diversity of Post-Immunization
IgG Antibodies to Type 19 Capsular Polysaccharide

| SUBJECT | V_H1 | V_H4 | V_H3 | 20PI/9-1-assoc | | 30PI/VH26-assoc |
|---|---|---|---|---|---|---|
| | | | | VH3-HV2a* | VH3-FR3a | VH13-HV2b* |
| 1. 10 | +++ | +++ | +++ | − | +++ | − |
| 2. 15 | − | ++++ | ++ | − | +++ | − |
| 3. 07 | +++ | − | − | +++ | + | − |
| 4. 12 | − | − | ++ | +++ | + | − |
| 5. 18 | − | − | ++++ | − | + | − |
| 6. 03 | − | +++ | − | + | ++ | − |
| 7. 01 | − | ++++ | ++ | + | + | − |
| 8. 02 | ++++ | − | ++ | − | ++ | − |
| 9. 05 | ++++ | − | + | ++ | ++ | − |
| 10. 09 | − | − | | ++ | ++ | − |
| | 4 | 4 | 7 | 6 | 10 | 0 |

FIG. 6

V_H Diversity of Post-Immunization
IgG Antibodies to Type 14 Capsular Polysaccharide

| SUBJECT | V_H1 | V_H4 | V_H3 | 20PI/9-1-assoc VH3-HV2a* | | 30PI/VH26-assoc VH3-HV2b* |
|---|---|---|---|---|---|---|
| | | | | VH3-HV2a | VH3-FR3a | |
| 1. 10 | – | – | +++ | +++ | + | – |
| 2. 15 | – | – | + | – | – | – |
| 3. 11 | – | – | + | +++ | – | – |
| 4. 12 | + | – | ++ | ++++ | – | – |
| 5. 08 | – | +++ | – | – | – | – |
| 6. 18 | – | ++ | ++++ | ++++ | ++ | – |
| 7. 13 | – | – | ++ | ++ | – | – |
| 8. 03 | – | +++ | +++ | ++++ | – | – |
| 9. 20 | – | ++ | ++++ | ++++ | +++ | – |
| 10. 12 | + | – | ++++ | ++++ | +++ | – |
| | 2 | 4 | 9 | 6 | 4 | 0 |

FIG. 7

METHOD FOR STIMULATING PRODUCTION OF VARIABLE REGION GENE FAMILY RESTRICTED ANTIBODIES THROUGH B-CELL SUPERANTIGEN VACCINATION

RELATED U.S. PATENT APPLICATIONS

This is a continuation-in-part of U.S. application Ser. No. 07/969,936, filed Oct. 30, 1992, now abandoned.

BACKGROUND OF THE INVENTION

1. Field of Invention

The field of this invention relates to antigenic stimulation of specific immune responses. Specifically, the invention relates to identification of B cell superantigens and their use as adjuvants and/or carrier proteins to enhance a specific immune response to bacterial or viral pathogens having polysaccharide or glycoprotein components in their cell walls, cell membranes, capsules or envelopes. More particularly, it relates to a method of enhancing the immune response by administration of said polysaccharide or glycoprotein with a B cell superantigen either concomitantly or in a chemically conjugated form.

2. History of the Prior Art

For a complete understanding of the invention, a brief summary of the role of clonal development of B cells in immune responses is helpful.

In the germ-line cells, there are three sets of germ-line genes involved in immunoglobulin coding: one set codes for the heavy chains, and the other two code for two types of light chain designated by the Greek letters kappa ($\kappa$) and lambda ($\lambda$), which differ significantly in the amino acid sequence of their constant domains. Immunoglobulins are composed of heavy and light chain heterodimers, which contribute to the conventional antigen binding site in the Fab portion. B cells themselves are lymphocytes which have immunoglobins on their cell surface which serve as receptors for antigens. Binding of antigen, in most instances together with additional signals from T cells, causes the original B cell to proliferate, forming clones. The expanded clonal population differentiates into memory cells and plasma cells, the latter of which synthesize and secrete antibodies which generally will have identical binding sites for the antigen which triggered the B cell activation. Polyclonal activation occurs when certain antigens (known to include mitogens and the Epstein-Barr virus) stimulate clonal expansion regardless of the antigen specificity of the B cells involved.

The human antibody repertoire is responsible for the acquisition of a dynamic and responsive immune defense system, but dysregulation within the B cell compartment can result in a wide spectrum of clinical conditions, including inappropriate B cell clonal expansions (e.g., B cell neoplasms), inadequate immune defense from infection, or autoimmune disease. During fetal development, antibody specificities are acquired slowly in a developmentally ordered fashion.

Referring for purposes of illustration to humans, the V, J, and D genes code in human cells for the variable regions of the antibody molecule and the C genes code for the constant regions. Each of the three germ-line sets contain from two to at least 300 alternative V genes, together with a small number of alternative J genes; the heavy-chain set also has alternative D genes. Any of these genes can contribute in the variable regions of antibody molecules. Each set has from one to five alternative C genes coding for different constant regions.

As a germ-line cell differentiates into a mature but "naive" B cell (i.e. one that is reactive to but has not yet encountered its matching antigen), somatic recombination of the germ-line genes takes place. In each cell, one of the V genes from each of the three germ-line sets is "selected" by an unknovin molecular process, together with one of the adjacent J genes (and in heavy chains, also with one of the D genes). These selected genes are brought together in the genome when the intervening DNA is excised. The basis of diversity in the antigen-recognition structure of an antibody molecule rests initially on this recombination event, since different genes are recombined in different B cells.

Although the first source of variation in the structure of the antibody molecule is brought about by somatic recombination of alternative V, D and J genes, further diversity in the amino acid sequence of the variable domains results from variable recombinations; i.e., slight variations in the exact location of the "cutting points" as first the germ-line DNA and later the mRNA transcripts are cut and spliced. Both these sources of variation occur before contact with antigen.

More variation arises after contact with antigen. Single base changes ("somatic mutation") occur in the DNA of activated B cells, mainly during the process of memory-cell formation.

A consequence of somatic mutation is that some of the binding sites produced by the mutated DNA have a better affinity for the antigen, and some have a worse affinity. Somatic mutations occur mainly during clonal expansion and memory-B cell formation, so the memory B cells from a single clone end up with receptors (i.e. surface immunoglobulin) for the same antigen, but with a range of antigen affinities (see, re development of the human antibody repertoire generally, Davey, *Immunology: A Foundation Text* (1990) Chapter 4, sections 4.3–4.3.2).

The process of repertoire selection may be the result of long-term exposure to many exogenous and endogenous contentional ligands, but a dramatic skewing of the immune repertoire can also be induced by a single limited exposure to certain unconventional antigens. These antigens, of bacterial or viral origin, were first distinguished based on an ability to interact with a large proportion of T lymphocytes. In contrast to conventional antigens, which generally stimulate less than 0.01% of T cells, these superantigens can stimulate 5–25% of all T cells. In explanation, many superarntgens are recognized by most (or all) T cells that use a particular V$\beta$ family. Based on available data, superantigen reactivity is little affected by differences in V$\beta$ junctional sequences, or by the alpha chains that are co-expressed. Moreover, recent studies indicate that an alternative site, remote from conventional antigen binding sites, allows for superantigen recognition by a large proportion of the T cell pool, usually those having particular V$\beta$ elements.

Superantigens have been proposed to contribute to the shaping of the mature T cell repertoire by clonal selection and/or deletion. Individual inbred strains of mice have been shown to carry different murine Mammary Tumor Virus encoded endogenous superantigens, and each exhibits a distortion of the distribution of T cell receptor V$\beta$ expression. This is usually due to deletion of T cells with certain V$\beta$ families, although there may also be more subtle effects on positive selection. Similar acute fluctuations may also occur in patients with toxic shock syndrome and Kawasaki's disease, presumably due to a T cell superantigen. Several recent papers have also suggested that superantigen exposure of predisposed individuals may, at times, result in immunosuppression, the production of autoantibodies, the development of autoimmune disease, or the abolition of an autoimmune process (see also, re characteristics of T cell superantigens, Fraser, et al. (1992) *J. Exp. Med* 175:1131–1134, and Taub, (1992) *Cell Immunol.* 140:267–281).

With this background, interest in the possibility that B cell superantigens (hereafter sAg) may exist can be understood. Several candidate sAg's are suggested by recent reports. For example, human IgM, IgA and IgGF(ab')$_2$ that bind to bacterial membrane protein staphylococcal protein A (SpA) have been shown to include a family of V$_H$ genes which encode polypeptides belonging to the V$_H$3 protein subgroup (the largest human family) (Sasso, et al., *J. Immunol.* (1991) 147:1877–1883 and Sasso, et al., *J. Immunol.* (1989) 142:2778–2783). As described further herein, SpA binds to the Fab region of a large proportion of V$_H$3 restricted immunoglobins at an alternative binding site different from its known, F$_C$γ binding sites and in greater proportion than conventional antibody binding. Further, the Fab sites which bind SpA are found on antibodies with diverse specificities.

Protein F$_V$, a sialoprotein released into the digestive tract during viral infection, has also been reported to interact with the Fab fragment of immunoglobins at an unconventional binding site believed to be in the V$_H$ domain (Bouvet, *Scand. J. Immunol.* (1991) 33:381–386). Further, based on reported binding by human Ig via the Fab region (in a setting in which prior immunization to create antibodies to conventional components is not required), known protein components of other microorganisms may also serve as B cell sAg.

The present invention includes a means of characterizing and identifying B cell sAg and using them to enhance production of V$_H$, particularly V$_H$3, restricted antibodies. In particular, the sAg will be identified, purified and administered concomitantly with a polysaccharide or glycoprotein component from a bacterial or viral cell wall or capsule or, preferably, as a carrier for a conjugate vaccine to the bacteria or virus. B cell superantigens with specificity for other Variable (V) region gene families may also exist, and be useful in certain vaccines.

In the past, there has been no rationale for selection of carriers for conjugate vaccines except the experience with these proteins as immunogens themselves. In each case, diphtheria toxoid, tetanus toxoid and OMB (outer membrane protein of *N. meningitides*) the carriers were selected and/or used clinically to elicit immunity to the pathogen. As a result they were shown to be immunogenic and safe for human use. Prototype conjugate vaccines were then made and tested in animal models, usually rabbit or mice. The only possible exception is the present OMB conjugate, which uses a liposome delivery system (Donnely et al., *J. Immunol* (1990) 145: 3071–3079).

SUMMARY OF THE INVENTION

In this application, the carrier or adjuvant sAg will be selected to specifically enhance a patient's antibody repertoire by specifically causing B cell activation and clonal expansion, in particular that which will produce V$_H$ and V$_H$3 restricted antibodies. This method is expected to be particularly effective in assisting patients to mount a defense to invasive infection by encapsulated bacteria and viruses because that defense is highly dependent on the production of antibodies specific for capsular or cell wall polysaccharides or envelope glycoproteins. Further, the very young and elderly members of a population, as well as certain ethnic populations of humans, are at increased risk of these infections due to impairments in the production of these antibodies. Use of a V region specific polyclonal activator should, therefore, be of particular value in treatment of these individuals.

Further, particularly when using a purified sAg, the potential for toxicity is far lower than that reported for conventional conjugate vaccines, because the stimulatory activity of the sAg will be limited to the B cell compartment. Compare this activity to, for example, the anti-haemophilus influenzae B (Hib) vaccine reported by Donnely, sugra, which uses an OMB protein carrier naturally contaminated with an endotoxin responsible for fever and other toxicity.

In addition, a B cell superantigen will by definition bind a larger proportion of Ig than would be bound by a conventional antigen. The percentage of surface Ig in a given B cell population which will normally bind to a particular superantigen can be quantified. The B cell superantigen may therefore serve as a phenotypic marker for a B cell population. Further, observed abnormalities in the binding pattern for a particular superantigen in a given B cell population may signal the onset or existence of a malignancy.

BRIEF DESCRIPTION OF THE DRAWINGS

FIG. 4A through R is a reproduction of stained flow cytometry studies showing binding to normal human tonsillar mononuclear cells by Protein G, SpA and hyperiodinated SpA. Protein G, SpA and hyperiodinated (mod) SpA are identified along the horizontal axis of each reproduction, while the antibody isotype (IgM or IgG) is identified along the vertical axis of each reproduction.

FIGS. 5–7 depict, in tabular form, the results of reactivity tests between human anti-polysaccharide bacterial antibodies and serologic reagents for variable region restriction of antibodies.

DESCRIPTION OF THE PREFERRED EMBODIMENTS

Figure 1:
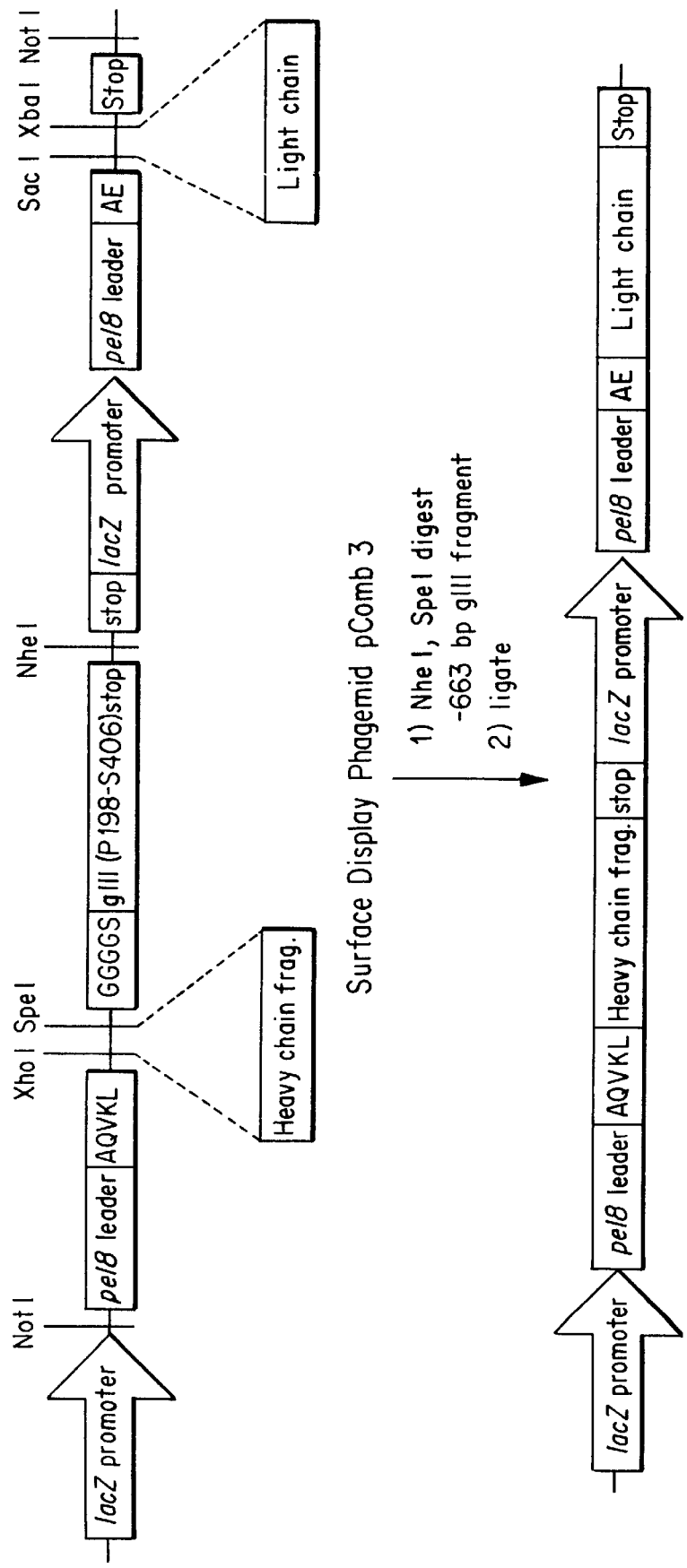
FIG. 1 diagrammatically depicts the pCOMB3 vector in its surface display and Fab producing forms.

A. CHARACTERISTICS OF sAg AND CANDIDATE ANTIGENS.

The first task in developing the inventive vaccine is to identify useful B cell sAg. Based on known qualities of T cell superantigens (described above) and the analytic work disclosed below, it is proposed that B cell superantigens will possess the following structural and functional properties:

1. Structural properties.

A) Superantigens should interact with isolated Ig and surface Ig.

B) Superantigen binding should be expressed by a large proportion of non-immune Ig of different isotopes (constant regions). This proportion should be much greater than might be expected to bind to a conventional antigen (e.g.,>1%).

C) Superantigen binding should be present on antibodies that also express diverse conventional antigen binding activities.

D) Superantigen binding should be restricted by subgroup or V family, and this interaction should correlate with conserved sequences that are outside of the conventional antigen binding site.

2. Functional properties.

A) In vitro stimulation with a superantigen should contribute to the selective stimulation of $V_H$ family restricted B cell populations.

B) In vivo stimulation with superantigen should result in dramatic shifts in the presentation within the B cell repertoire, which numerically are much greater than can occur after hyperimmunization with a conventional antigen.

To characterize a candidate antigen as a B cell superantigen, analytical methods are described below which will confirm whether the antigen possesses the above-listed characteristics. Depending on whether the candidate antigen is already known to possess certain characteristics, certain steps of the approach described below may be viewed by those skilled in the art as optional. It will also be clear to those skilled in the art upon review of the disclosed approach that certain steps may be accomplished by other means (using, for example, a different vector in the development of combinatorial Fab libraries, or an analytical method other than flow cytometry to gauge sAg candidate binding specificities). However, the methods identified below have proved to be efficient and useful means of characterizing a B cell sAg.

For purposes of clarity, it should be noted that the below approach has been described in a specific context; i.e., toward characterizing staphylococcal protein A (SpA) as a B cell sAg. However, the approach is not so limited and can be applied to other candidate antigens as well. In this regard, candidate antigens for characterization as sAg based on their demonstrated binding to human Ig via the Fab region include:

1. Protein A (from *Staphylcoccus aureus* [cell membrane]).
2. Protein L (from *Peptococcus magnus* [in cell wall]).
3. Protein P (from *Clostridia pertingens*, [cell surface component]) with molecular weight (MW) of 190,000.
4. Protein B (from Group B Streptococcus [certain strains] protein with MW of 25,000).
5. *Brucella abortus* (protein component from certain strains).
6. *Taylorella equigeuitalis* (whole bacteria)
7. *Streptococcus zooepidemicus* (whole bacteria).
8. *Aeromonas salmonicida* (protein component with MW of 49,000).
9. Protein $F_V$ (human liver protein with $V_H$ restricted binding to Fab).

B. ANALYTIC METHODS FOR IDENTIFICATION OF sAg (USING SpA EXAMPLE).

Step 1. Structurally characterize the site on Ig receptors responsible for interaction with the candidate antigen.

i. Immunoblotting analysis.

Incorporated by reference herein is a disclosure of serologic reagents to distinguish the products of V kappa gene families in humans. Each of these antisera identifies a sequence selected from a first framework (FW) region portion that is highly conserved by members of a particular $V_k$ family, but differs from the homologous FW sequences from other $V_k$ families (Silverman, et al., (1986)) *J. Immunol. Methods* 95:249–257). A second reference, also incorporated herein, discloses reagents to discriminate the genetic origin of heavy (H) chains, based on analyses of V region DNA sequence homology identifying at least six distinct $V_H$ gene families (Berman, et al., (1988) *EMBO, J.* 7:727–738 [re $V_H$ gene families]; see also (incorporated herein) Silverman, et al. (1988) *J. Clin. Invest.* 82:469–475; Silverman, et al. (1988) *J. Exp. Med.* 168:2361–2366; and, Silverman, et al. (1990) *Arthritis Rheum.* 33:1347–1360 [re reagents]).

Polyclonal or monoclonal Ig may be separated into binding and non-binding fractions by, for example, passage over affinity columns such as agarose (e.g., "SEPHAROSE" having the candidate antigen bound to the solid phase. These fractions are then analyzed by immunoblotting with the V family specific serologic reagents (for further reference see, incorporated herein, Sasso, et al., (1988) *J. Immunol.* 140:3098–3107 [re polyclonal and monoclonal IgM rheumatoid factor specificities]; and, Sasso, et al. (1989) *J. Immunol.* 142:2778–2783 [re human IgM specificities for SpA]).

ii. Application to SpA.

To apply this method to SpA, the binding activity of its purified recombinant form (available from Calbiochem, La Jolla, Calif. under the trademark "ULTRAPURE") is tested against panels of purified monoclonal IgM and IgG proteins that are representative of all known $V_k$ and $V_H$ families, as well as the binding activity of SpA modified by hyperiodination to destroy IgG Fc binding activity (mod-SpA). (It should be noted that although as further noted herein other forms of SpA may be used, the recombinant form is preferred. Therefore, unless otherwise indicated, SpA as referred to herein will mean the recombinant form). In the binding tests, both SpA and mod-SpA were biotinylated according to means known in the art, for use in an enzyme linked immunoassay (i.e., EUSA) and flow cytometry.

As shown in Table I, within this limited panel of monoclonal IgM, the mod-SpA (without Fc binding activity) was bound by 15/16 $V_H3$, but none of the 7 $V_H1$, 7 $V_H4$, 1 $V_H5$ and 1 $V_H6$ proteins tested. Among monoclonal IgG, mod-SpA bound only 2/6 $V_H3$ (GER and SFL), but none of the 4 $V_H1$, 1 $V_H2$, and 1 $V_H4$ proteins tested. Therefore, these data demonstrate that using Ig examples of the $V_H$ families, $V_H1$, $V_H2$, $V_H4$, $V_H5$ and $V_H6$ proteins, did not express SpA binding capacity, because SpA binding was limited to certain Fab that contain $V_H3$ H chains ($X^2$, P<0.001). Moreover, SpA binding was present in Ig from at least four $V_L$ families, including both kappa and lambda L chains and SpA binding activity was not restricted to antibodies with a single conventional antigen binding activity. Also, H chains denatured and reduced in Western immunoblot analysis cannot bind SpA.

This data supports the impression that the $V_H$ binding site for SpA is a conformational component, which requires L chain for expression even though L chains may not be directly involved in SpA binding. In addition, although this panel contained antibodies with a variety of conventional antigen binding actities, both autoreactive (RF, anti-DNA, anti-Sm) and anti-bacterial (anti-Haemophilus and anti-pneumococcal) antibodies, SpA binding activity was not restricted to antibodies with a single conventional antigen binding activity. Further, it should be noted that binding to the "alternative binding site" of SpA may be less common in the products of more mature B cell populations as a much larger proportion of the $V_H3$ IgM (17/19) than $V_H3$ IgM (2/7) bound the modified SpA ($X^2$, P<0.005). A partial compilation of this data is shown in Table I in the left hand columns.

hand column). Sequence analysis confirmed that the $V_H$ regions of Ig that bind SpA share considerable homology in the framework (FW) regions. However, the composition of the hypervariable regions vary greatly, because these H chains express $V_H$ regions that represent rearrangements of at least five different $V_H3$ germline genes.

Immunization with a conventional epitope often induces antibody clones with the same (or very similar) V genes within a family, which often share conserved sequences in the hypervariable loops of $V_H$ and/or $V_L$ regions that may be intimately responsible for antigen binding. In contrast, a $V_H$ specific superantigen would be predicted to interact with diverse members within a $V_H$ family, which do not necessarily share sequences within the hypervariable loops. Therefore, conservation of $V_H$FW residues in Ig with SpA binding likely reflect the B cell superantigen functional

TABLE 1

Structural and functional properties of monoclonal Ig proteins.

| | $V_H1$ | | $V_H2$ | | $V_H3$ | | $V_H4^+$ | | $V_H5$ | | $V_H6$ | |
|---|---|---|---|---|---|---|---|---|---|---|---|---|
| | SPA | $V_L$ | SPA | $V_L$ | SPA | $V_L$ | SPA | $V_L$ | SPA | $V_L$ | SPA | $V_L$ |
| IgM | | | | | | | | | | | | |
| And | − | κ3 | | | Buc | + | κ1 | Cor | − | κ3 | A224* | − | λ | L16* | − | λ |
| Bor | − | κ3 | | | Cha | + | κ1 | Far | − | λ | | | | | | |
| Gil | − | κ4 | | | Chr | + | κ1 | Gre | − | κ3 | | | | | | |
| Jan | − | κ3 | | | Dau* | + | κ3 | Les | − | κ3 | | | | | | |
| Kas | − | κ3 | | | Erik | + | κ3 | Odo* | − | κ3 | | | | | | |
| Pal | − | κ3 | | | Glo | + | κ3 | Ore | − | κ3 | | | | | | |
| Sic | − | κ3 | | | Hea | + | κ3 | Ple | − | κ3 | | | | | | |
| | | | | | Kim 4.6* | + | κ3 | | | | | | | | | |
| | | | | | Lay | + | κ1 | | | | | | | | | |
| | | | | | Pom | + | κ3 | | | | | | | | | |
| | | | | | Riv | + | κ3 | | | | | | | | | |
| | | | | | Sim | + | κ4 | | | | | | | | | |
| | | | | | 18/2* | + | κ1 | | | | | | | | | |
| | | | | | 4B4* | + | κ4 | | | | | | | | | |
| | | | | | 591* | + | λ | | | | | | | | | |
| | | | | | Ioh | − | κ4 | | | | | | | | | |
| pG | | | | | | | | | | | | |
| Fine* | − | κ2 | Cess* | − | λ | Ger* | + | NT | Cla* | − | κ1 | |
| Heb* | − | λ | | | | SFL* | + | κ3 | | | | |
| Hou* | − | κ1 | | | | Cal* | − | λ | | | | |
| Long* | − | λ | | | | Do* | − | κ1 | | | | |
| | | | | | | Fnz* | − | λ | | | | |
| | | | | | | Mag* | − | NT | | | | |

Regarding the site on SpA which is responsible for $V_H3$ binding, the data set forth in Example I below demonstrate that the "D" domain of SpA contains an Ig Fab binding domain. This domain may itself be utilized as the sAg for use in the vaccination methods of the invention.

To explain, it is known that SpA has 5 independent, homologous domains which can bind Ig (commonly referred to as domains A, B, D, E and X). However, it has not been known which of these regions, if any, possess Fab (as opposed to Fc) binding activity. The work described in Example I demonstrated for the first time that domain D not only will bind Ig Fab, but will also preferentially bind Fab of $V_H3$ restricted Ig. As a result, SpA and this domain of SpA can be used as a carrier or adjuvant in an immunization protocol to specially enhance the production of $V_H3$ restricted antibodies by a patient.

iii. Correlation of $V_H$ region sequence with SpA binding activity.

All available $V_H$ sequence data from the above-described panel were compiled to determine whether Ig that bind mod-SpA have conserved structural motifs (Table II, right capacities, because the interaction is outside of the conventional antigen binding pocket.

In Table II.A the amino acid sequences of H chains from Ig reactive with mod-SpA are displayed. The amino acid sequences of H chains for evaluation of binding to mod-SpA by immunoassay are displayed (all are $V_H3$ region derived). The single letter code for amino acid residues is used, and # represents a pyrrolidonecarboxylic acid residue, X is undetermined, and * is a space. The IgM proteins 4B4, 18/2, KIM4.6 and L16 directly derive from the germline configuration of $V_H$ gene segments, and these genes are listed under GL $V_H$. SB5/D6 and ED8.4 are anti-hameophilus influemze PS cell lines. The IgM proteins (LAY, POM, RIV, BOR, KAS and SIE, and IgG protein SFL, are circulating monoclonal antibodies from patients with lymphoproliferative syndromes. Huabl4-3 and Huab 2-3 are antipneumococcal capsular polysaccharide type 3 cell lines. The conventional antigen binding activity of $V_H3$ antibodies is listed under $Ag^+$. Relative reactivity with modified-SpA is depicted as $OD_{405}$ 0.100–0.400+0.401–0.800++, 0.801–1.200+++. NT indicated that binding for a sequence was not tested.

TABLE 2A

Human V_H Regions and SpA Reactivity[1]

| Ix blanders[5] T0/2 | QLYx[2] V_x26 | Ag[3] | mod SpA[4] | CDR1 ... CDR2 ... CDR3 |
|---|---|---|---|---|
| | | | | E V Q L L E S G G G L V Q P G G S L R L S C A A S G F T F S S Y A M S * * W V R Q A P G K G L E W V S A I G G * * S G G S T T Y A D S V K G R F T I S R D N S K H T L Y L Q M H S L R A E D T A V Y T C T R G Q V L T T G S G S Y * * * * * R W F D P W G Q G T L V T V S S |
| KD8.4 | | DNA | IgN ++ | — — — — — — — — — — — — — — — — — — — — — — — — — — — — — — — — — — — — — — — — — — — — * * — — L - P — — — — — — — — — — — — — — — — — — — — — — — — — — — — — — — — — — — * * — R — — — — — — — — — — — — — — — — — — — — — — — — — — — — — — — — |
| HbPS | | HbPS | IgM +++ | — — — — — — — — — — — — — — — — — — — — — — — — — — — — — — — — — — — — — — — — — — — — — E — — — — — — — — — — — — V — — — — — — — — — — — — — — — — — — — — — — — — G Y G * * * * * * * * * * K D V W — — — |
| Nusb14-3 | | PS3 | IgM +++ | — — — — — — — — — — — — — — — — — V — — — — — — — — — — — — — — — — — — — — — — — — — — T - R - R * * — — — — — — — — — V — — — R - N S * * D - S — D — — — E — — — — |
| SFL | | RF | IgG ++ | — — — — — — — — — — — — — — — — — — — — — — — — — — — — — — — — — — — — — A — — — — — — — T K Y X — * * — — — — — — — — — F D S * * * * * * * * * * * * * * * * * * * |
| KIN_{4,G} | | DNA | IgM ++ | — — — — — — — — — — — — — — — — — V — — — — — — — — — — — — — — — — — — — — — — — — — — — G - H * * — — — — — — — — — A F I Y R * * — — I N R — — — — M — — — — — — |
| 1-9111 | | | | — — — — — — — — — — — — — — — — — Q — — — V — — — — R — — — — — — — — — — — — — — — — — — — — — — — — — — — — — — — X — — — X X X — — — — — — — — — L — — A - D A G - K V E R S V |
| RIV | | RF | IgN ++++ | — — — — — — — — — — — — — — — — — — — — — — V — — — — — — — — — — — — — — — — — — — — — — F — H * * — — — — — — — — — A - V R K Y — S — * * * — Y Y Y Y G M D V — — — T — — — — — |
| LAY | | RF | IgM +++ | — — — — — — — — — — — — — — — — A — — — — — — — — — — — — — — — — — A S — * * — — — — — — — A V M - Y * * — D N K — — V — — — — — |
| KIN | | RF | IgN | — — — — — — — — N D — — — — — — — — — — — — — Q — — S - I — — — A - L S T A A S - F T F D T Y G M D — * * — — — — T — — — — |
| PON | | RF | IgN ++++ | — — — — — — — — — — — — — — — — — — — — — — — — — — — — — — — Q — — S — I — — — A R D A G P - V S P T F * * * * * * * F A M — — — — — — |
| | | | | — — — — — — — — N D — — — — — — — — — S — * * — — — L — — Q — — — L — — A R D A G P - V S P T F * * * * * * * F A H Y — — — — — — |

TABLE 2A-continued

Human V_H Regions and SpA Reactivity[1]

| | | | | | | | | | | |
|---|---|---|---|---|---|---|---|---|---|---|
| Nusb2-3 | | IgM | ++++ | ----V--- | R-------- | -------- | --AS-VH**WV---S------ | --GR-RSKANSYA---A---A--- | -------- |
| SB5/D6 | | IgA1 | ++ | | | ----D----A------- | -------KT------GHPLTTVTTP******* | -------- |
| | | | | ----V---K | -------- | -------- | ----NAH-N**------P--- | --GR-KTKTD--T-D--AP------ | -------- |
| | | | | | | | ---ND----------- | -------KT-------TGGGV*************G | -------- |
| 4D4 | 9-1 | Sm | + | ----V---K | -------- | ----D--- | ----NAW-**-------- | --GR-KSKTD--T-D--AP------ | -------- |
| | | | | | | | ------KT---------- | --TDSLPPHRV**************- | -------- |

Fab bladers from SpA3 library[6]

| | | | | | | | | | |
|---|---|---|---|---|---|---|---|---|---|
| SpA3-08 | SpA | T | ++++ | -K----- | -------- | -------H-** | -------*-------L---ASSGAGNGLPSLDY********** | ----D---** | -------- |
| SpA3-02 | SpA | T | ++++ | -K----- | -------- | -------H-** | -------*-------L---ANSGAGWGLPSLDY********** | ----D---** | -------- |
| SpA3-37 | SpA | T | ++++ | -K----- | -------- | -------H-** | -------*-------R---ANSGAGWGLPSLDY********** | ----D---** | -------- |
| SpA3-13 | SpA | T | ++++ | -K----- | -------- | -------H-** | -------*-------R---ANSGAGWGLPSLDY********** | ----D---** | -------- |
| SpA3-15 | SpA | T | ++++ | -K----- | -------- | -------H-** | -------*-------L---ANSGAGWGLPSLDY*******L | ----D--- | -------- |
| SpA3-16 | SpA | T | ++++ | -K----- | -------- | -------H-** | -------*-------R---ANSGAGWGLPSLDY********** | ----D---** | -------- |
| | | | | | | | -------*-------L---ANSGAGWGLPSLDY********** | ----D---** | -------- |

TABLE 2A-continued

Human V_H Regions and SpA Reactivity[1]

| | | | | | | | | | |
|---|---|---|---|---|---|---|---|---|---|
| SpA3-18 | SpA | T | ++++ | KL-K--------- | -----V------- | --------*---- | ---*-H----*-- | R------L---ANSGAGWGLPSLDY********** | D---*-------- |
| SpA3-39 | SpA | T | ++++ | KL-K--------- | | | | R------L---ANSGAGWGLPSLDY********** | D---*-------- |
| SpA3-33 | SpA | T | ++++ | KL-K-------VP | -------K----P | -N-G----A--S- | ------------- | S---*-------- ARDAWDAFDI************* | -----M------- |
| SpA2-07 | SpA | T | ++++ | VKL-EQ------- | | | | R------L---ANSGAGWGLPSLDY********** | D---*-------- |
| SpA1-30 | SpA | T | ++++ | VKL-EQ------- | | | | R------L---ANSGAGWGLPSLDY********** | D---*-------- |

Is VH3 non-blnders[7]

| | | | | | | | | | |
|---|---|---|---|---|---|---|---|---|---|
| LSF3 | HIbPS | IgA1 | - | -----V------- | ------IK----T | ----I---NAW-H** | ------R-----GR-KKKTD--T-D--AP------ | | |
| CA4/PRP-13 | HIbPS | IgG2 | - | -----V------- | ---------T--- | -------TFNTY-HN- | V---D-QS-V---S----T------GTRDY********** | | |
| | | | | | | | ----S--R**-SDYI--P----- | | |
| | | | | | | | -----TP--PV----T--D-----A- | | |

Is non-blnders[8]

| | | | | | | | | | |
|---|---|---|---|---|---|---|---|---|---|
| BOR | V_H1 | IgM | - | #---VQ--AEVKK--S-VKVT-K---D----SAI--- | | ----------Q---MGG-IPIF-TPN--QRFQ--V- | | | |
| | | | | -TT-E-TS-A-MEVS---S----L---AREGRRHAI NP********-Y-------- | | | | | |
| KAS | V_H1 | IgM | - | #---VQ--AEVKK--S-VKVT-K---G------I--- | | ----------Q---MGG-IPIF-QAN--QRFQ--V- | | | |

TABLE 2A-continued

Human V_H Regions and SpA Reactivity[1]

| | | | | |
|---|---|---|---|---|
| SIE | V_H1 | RF | IgM | # - - - V Q - - A E V K K - - S - V - V T - K T - - Q - - - G - T F S * * - - - - - - - R - - - - - G S P A K * * N T D P F Q G V T I K W E - V - - - - - - - - - - - - - - - T A - E - T - - A - M E L R - - - S D - - - M - - - A - E G Y G D - - R P * * * * * * * * - - F - - - - - - - |
| CRSS | V_H2 | ? | IgM | V - L K P - F - Q A - M E L V N - F N - - G - - - - - A R E W K G Q V N V N P * * * * * * - - Y - - - - - V - - - - |
| LES | V_H4 | RF | IgM | Q - N - R - - P A - - K A T H T - T - T F - - L S V N T R G - - V S - I - - P - - A - - L A R - D * * * N D D D K - - G T - L E T - L - - - - K - T - - - Q V V - K V T N M D P A - - - T - - A R M - - T M V R K V M I T S N A F * - I - - - - - M - - - - |
| A224 | V_H5 | Poly | IgM | Q V Q - Q Q W - A - - L K - S - - T - S - T - - V I - G P - - G - Y N - * * - - - - P - - - - P - - I G E - N * * - H S - R - T - N P - L T S - V - - - - - - - - M - L - T - - - Q F S - K L T - V T - A - - - V - - L A R - P C Z A - C T D D A P Q A * Y F Q H - - - |
| L16 | V_H6 | Poly | IgM | - - - - - V Q - - A E V K K - - E - - K I - - K T - - T S - T N - W I G * * - - - - - N - - - - - M G L - Y P * * G D S G - R - S P - F - - Q V - - - - - - - - - - - - - A - K - I S - A - - - W S - - - - S - - - M - - - A R |
| | | | | Q - - - Q Q - - - P - - - K - S Q T - S - - T - - - I - - D S V - - N S A A H N - I - - S - S R - - - L G H Y Y Y R * - K H Y N D - - V - - - S - I - - - - - - - - - - - - - N F - T - - - Q F S - - L N - V T P - - - - V - - A R E L G D A F * * * * * * * * * * - - I - - - - - M - - - - |

[1] The amino acid sequences of monoclonal Fab and antibodies are displayed with their SpA reactivity. The single letter code for amino acid residues is used, and # represents a pyrrolidonecarboxylic acid residue, X is undetermined, * is a gap without a residue and − indicates the same amino acid as in the top sequence is used.
[2] If these V_H regions are directly encoded by V_H gene segments in their germline configuration, these genes are used.
[3] If the antibody was initially identified based on binding to a conventional bacterial or self antigen, it is indicated. RF, rheumatoid factor, DNA, anti-DNA binding, Hib PS, antibody activity to the capsular polysaccharide of HAemophilus influenzae type b. PS 3, antibody activity to the capsular polysaccharide of S. pneumoniae type 3. ?, no known binding activity. Poly, polyreactive.
[4] The relative binding activity to SpA that has been modified to remove Fc binding activity, but retains Fab binding activity is displayed. Relative reactivity with modified-SPA by direct binding ELISA is depicted under mod-SpA, as OD_405 0.100–0.400 +, 0.401–0.800 ++, 0.801–1.200 +++, > 1.200 ++++. NT, not tested.
[5] These are intact IgM and IgO antibodies with significant Mod SpA binding activity. The IgM 4B4, 18/2, and KIM4.6 are from B cell lines that use germline configuration V_H gene segments. The IgM proteins, LAY, POM, RIV, BOR, KAS AND SIE, AND IgO, SFL, are circulating monoclonal antibodies from patients lymphoproliferative syndromes.
[6] These monoclonal Fab were isolated from a combinatorial library based on SpA binding activity.
[7] These are monoclonal VH3 antibodies that are devoid of SpA binding activity.
[8] These are non-VH3 monoclonal antibodies that are devoid of SpA binding activity.

Table II.B depicts the DNA sequences of $V_H$ regions of SpA binders from combinatorial libraries (discussed further under Step 2, below). The amino acid sequences of Table II.A as well as the nucleotide sequences of Table II.B are set forth in the Sequence Listing herein as SEQ. ID. NO: 1 through SEQ. ID. NO: 48.

TABLE 2B

DNA sequences of V$_H$ regions of SpA binders from combinatorial libraries[1]

| | 20 | | | 40 | | | | 60 | | | | 80 | | | | 100 | | | | 120 |
|---|---|---|---|---|---|---|---|---|---|---|---|---|---|---|---|---|---|---|---|---|
| | CAGGT CAAAC TGCTC GAGTC TGGGG | GAGGA TTGGT ACAGC CTCCG GGGTC CCTGA GACTC TCCTG TGCAG CCTCT GGATT | | | | | | | | | | | CACCT TTAGC AGCCA | | | AGCCA TGAGC TGGGT CCGCC AGGCT | | | | |
| | | | | | | | | | | | | | | | CDR1 | | | | | |
| SpA2-02 | | | | | | | | | | | | | | | | | | | | |
| SpA3-08 | ........ ........ _____ ........ ........ | ........ ........ ........ ........ ........ ........ | | | | | | | | | | | ........ ........ ........ | | | ........ ........ ........ ........ | | | | |
| SpA3-13 | ........ ........ ........ _____ ........ | ........ ........ ........ ........ ........ ........ | | | | | | | | | | | ........ ........ ........ | | | ........ ........ ........ ........ | | | | |
| SpA3-15 | ........ ........ ........ _____ ........ | ........ ........ ........ ........ ........ ........ | | | | | | | | | | | ........ ........ ........ | | | ........ ........ ........ ........ | | | | |
| SpA3-16 | ........ ........ ........ _____ ........ | ........ ........ ........ ........ ........ ........ | | | | | | | | | | | ........ ........ ........ | | | ........ ........ ........ ........ | | | | |
| SpA3-18 | GTGAA ACTG. _CGAG_ ........ | ........ ........ ........ ........ ........ ........ | | | | | | | | | | | ........ ........ ........ | | | ........ ........ ........ ........ | | | | |
| SpA3-18 | GTGAA ACTG. _CGAG_ ........ | ........ ........ ........ ........ ........ ........ | | | | | | | | | | | ........ ........ ........ | | | ........ ........ ........ ........ | | | | |
| SpA3-37 | ........ ........ ........ ........ ........ | ........ ........ ........ ........ ........ ........ | | | | | | | | | | | ........ T. C. ........ | | | ........ ........ ........ ........ | | | | |
| SpA3-33 | GTGAA ACTG. _CGAG_ ........ | ........ ........ ........ C ........ ........ | | | | | | | | | | | ........ .C. T. A. T. | | | ..G. ....A. ........ ........ | | | | |
| SpA2-08 | ........ ........ ........ ........ ........ | ........ ACC ........ ........ G. ........ | | | | | | | | | | | ........ ........ ........ | | | ........ ..T. ........ ........ | | | | |

TABLE 2B-continued

DNA sequences of V$_H$ regions of SpA binders from combinatorial libraries[1]

```
                                                                                140
SpA1-30  GTGAA ACTG. .CGAG C....  ..... ..... ..... ..... ..... T. C.. ..... ..... ..... ..... ..... ..T. C. ..... ..A.. ..... .....
SpA3-29  ..... ..... ..... .....  ..... ..... ..... ..C.. ..... ..... ..... ..... ..... ..... ..... ..... C. .T. .A. T. ..... .....
SpA1-14  ..... ..... ..... .....  ..... ..... ..... ..... ..C. .A. .T. ..... ..... ..... ..... ..... ..... ..... ..C. .T .ATT. ..... .....
0-19     ..... ..... ..... .....  ..... ..... ..... ..C.. ..... ..... ..... ..... ..... ..... ..... ..... ..C. .T. .TT. CTGG. .CA.. ..... .....
VH26C    G.... ..C. G. ..T. .....  ..... ..... ..... ..C.. ..... ..... ..... ..... ..... ..... ..... ..... ..... ..... ..C. TT ..... .....

CDR2
                                  ────────────────────────────────────────────
                                                              160                            180                           200
         CCAGG GAAGC GCCTG GAGTG CGTCT CAGAT ATTAG TGCCA GTGGT GGTAG CACAT ATTAT GCAGA CTCCG TGAAG GGCCG
                                                                                              220
                                  GTTCA CCATC TCCAG AGACA ATTCC AAGAA CACGC TGTAT
                                                                              240
SpA3-02  ..... ..... ..... .....  ..... ..... ..... ..... ..... ..... ..... ..... ..... ..... ..... ..... ..... ..... ..... .....
SpA3-08  ..... ..... ..... .....  ..... ..... ..... ..... ..... ..... ..... ..... ..... ..... ..... ..... ..... ..... ..... .....
SpA3-13  ..... ..G.. ..... .....  ..... ..... ..... ..... ..... ..... ..... ..... ..... ..... ..... ..... ..... ..... ..... .....
SpA3-15  ...C. ..... ..... .....  ..... ..... ..... ..... ..... ..... ..... ..... ..... ..... ..... ..... ..... ..... ..... .....
SpA3-16  ...C. ..... ..... .....  ..... ..... ..... ..... ..... ..... ..... ..... ..... ..... ..... ..... ..... ..... ..... .....
SpA3-18  ...C. ..... ..... .....  ..... ..... ..... ..... ..... ..... ..... ..... ..... ..... ..... ..... ..... ..... ..... .....
SpA3-39  ...C. ..... ..... .....  ..... ..... ..... ..... ..... ..... ..... ..... ..... ..... ..... ..... ..... ..... ..... .....
```

TABLE 2B-continued

DNA sequences of V_H regions of SpA binders from combinatorial libraries[1]

| | | | | | | | | |
|---|---|---|---|---|---|---|---|---|
| | | | 260 | | | | | |
| SpA3-37 | . . . . . . | . C . . | . . . . . | . . . . . | . . . . . | . . . . . | . . . . . | . . . . . |
| SpA3-33 | . . . . . . | . G . . | . . . . . | . AG . . | . . . CA . | . . . . . A . . . T . | . . . . . C . . . C | . . . . . . . . . CG . | . . . . . . T . A . |
| SpA2-08 | . . . . . . | . C . . | . . . . . | . . . . . | . . . GT . | . . . . . . . . . . . A . . . . | . . . . . C . . C | . . . . . . . . . CG . | . . . . . . . . . |
| SpA1-30 | . . . . . . | . . G . | . . . . . | . . . . . | . . . . . | . . . . . | . . . . . | . . . . . | . . . . . |
| SpA3-29 | . . . . . . | . G . . | . . . . . | . . . . . | . . . . . | . . . . . A . C | . . . . . C . . C . . . G | . . . . . . . . . G . . . . . T | . . . . . . . . . |
| SpA3-14 | . . . . . . | . . . . | . . . . T . | . . . CG . | . . A CA TG A . . . G A . . . A . . . A G . . . C . . . G | . . . . . . . . . . . A . . . . | . . . . . . . . . | . . . . . . . . . CG . | . . . . . . C . . |
| 0-19 | . . . . . . | . C . . | . . . . . | . . G . . . T . G . AT . GTATG A . . . A AC . . C T . AG . | . C . . . . . . . . . . . | . . . . . C . . . . . G . . | . . . . . . T . . . . C . . G . . | . . . . . . . . . C . . . . | . . . . . . . . . |
| VR26C | . . . . . . | . G . . | . . . . . | . . . GT . | . . . . . C . . . | . . . . . C . . C . . . G . . | . . . . . . . . . . . T . . . | . . . . . . . . . | . . . . . . . C . . |

| | | 260 | | | | | 280 | | |
|---|---|---|---|---|---|---|---|---|---|
| SpA3-02 | TTGCA AATGA ACAGC CTGAG AGCCG AAGAC ACGGC CTTAT ATTAC TGTGC G | | | | | | | | | |
| | (M) D (N) | | | | | | | | |
| | TCCAACGGCGCGGGATGGGGGCTACCTTCCC | | | | | | | | |
| | TTG ACTAC TGGGG CCAGG GAACC CTGGT CACCG TCTCC | | | | | | | | |
| SpA3-08 | TCCAGCGGCGCGGGATGGGGGCTACCTTCCC | | | | | | | | |

TABLE 2B-continued

DNA sequences of $V_H$ regions of SpA binders from combinatorial libraries[1]

| | | | |
|---|---|---|---|
| SpA3-13 | . . . . . . . | . . . . . . . . . . . . . . . . . . . . . . . . . . | TCCAACGGCGCGGGATGGGGCTACCTTCCC |
| SpA3-15 | . . . . . . . | . . . . . . . . . . . . . . . . . . . . . . . . . . | TCCAACGGCGCGGGATGGGGCTACCTTCCC |
| SpA3-16 | . . . . . . . | . . . . . . . . . . . . . . . . . . . . . . . . . . | TCCAACGGCGCGGGATGGGGCTACCTTCCC |
| SpA3-18 | . . . . . . . | . . . . . . . . . . . . . . . . . . . . . . . . . . | TCCAACGGCGCGGGATGGGGCTACCTTCCC |
| SpA3-39 | . . . . . . . | . . . . . . . . . . . . . . . . . . . . . . . . . . | TCCAACGGCGCGGGATGGGGCTACCTTCCC |
| SpA3-37 | . . . . . . . | . . . . . . . . . . . . . . . . . . . . . . . . . . | TCCAACGGCGCGGGATGGGGCTACCTTCCC |
| SpA3-33 | C . . . . . . | . . . . . . TC. G. . . . . . . . . . . . . . .AGA | GATGCATGGGATGCATTTGATATC |
| SpA2-08 | C . . . GC. . . . . . T | . . . . . . .G. . . . . . . TG. G. . . . . . . . . . .AA | GACCCGAGTTAGGAGGACTGATGGTTATCG<br>. . . . . . . . . . . . .A. . C. |
| SpA1-30 | . . . . . . . | . . . . . . . . . . . . . . . . . . . . TA ACCCC CTCTG .G. | TCCAACGGCGCGGGATGGGCCTACCTTCCC |
| SpA1-29 | C . . . . . . | . . . . . . .G. . . . . . . TG. G. . . . . . . . . .G TA | GAGGATACAGCTACCCTGTCTGGGGGCGC |
| SpA1-14 | C . . . . . C. . . . . . T | . . . . . . .G. . . . . . . TG. G. . . . . . . . . .AAGA | GCCGAATTCCGACGCCCAATGGTTATG<br>. . . . . . . . . . .A. .G. . . . AC. |

TABLE 2B-continued

DNA sequences of V$_H$ regions of SpA binders from combinatorial libraries[1]

```
              CTAAC CCCCC TCC. . G. . . . . . . . . . . . . . . . . .

0-19  C. . . . . . . . . . . . . . . . . .T. . .G. . . . . . TG. C. . . . . . . . . . A      AAGGATACCAGTTG
                                                                                      . . . . . . . . . . . .
                                                                                T. . . . . . . . . . . . . . .

VII26C C. . . . . . . . . . . . . . . . . . . . . . .G. . . . . . . . . . . . . .G. . . . . . . . . . . AAA
```

[1] These DNA sequences of VH regions were obtained from monoclonal Fab with SpA binding activity. The germline gene VII26c is included for To further refine a model of a $V_H$FW defined SpA binding site, SpA binding activity may be correlated with single $V_H$ region mutations. In particular, FW sequences may be correlated sequences. Therefore, FW1 and/or FW3 components can be critical for binding of conventional antigens, and conserved FW motifs have also been shown to be critical for binding of a T cell superantigen. Significantly, amongst members of a $V_H$ family, the sequences in FW1 and FW3 have limited variability and the conservation of residues in FW3 within members of a family has been proposed to provide initial family associated constraints for affinity for specific epitopes.

On the H chain, the FW1 and FW3 regions represent a large surface that is highly solvent exposed, and which is not directly in contact with the L chain. Taken together, these data suggest that it is highly possible that FW residues form the contact region for the alternative binding site of SpA, but that constant-domain regions may still affect the interaction. For these reasons, mutagenesis experiments can be informative in the determination of whether FW3 (with or without FW1) directly contributes to the contact site of a B cell superantigen bearing in mind that amino acid changes in non-contact residues can cause remote conformational changes can affect binding affinity.

Step 2. Assessment of V region diversity on binding activity using a bacterial expression system.

i. Construction of a combinatorial library.

Optionally, the binding site on Ig for the candidate antigen can be localized and characterized. Useful to this end is the pCOMB3 phagemid vector constructed at Scripps Clinic, La Jolla, Calif. (laboratory of Drs. Dennis Burton and Richard Lemer). As depicted in FIG. 1, pCOMB3 will efficiently clone and express, separately or in combination, human IgH and L chains.

The vector is designed to create a fusion protein between the $V_H$ fragments and gill (the minor coat protein of the M13 phage), which can be arranged on the surface of M13 phage that contain the encoding V genes (disclosed in Barbas, et al. (1991) *Methods Enzymol.* Z:119–124, which is incorporated herein). The gene encoding the M13 portion of the fusion protein can also be excised with SpeI and NheI and, after re-ligation, the transfected bacteria secrete Fd fragments $V_H$-CH1 and $V_L$-CL1).

The pCOMB3 vector (and a related pCOMB8 vector) are not at this time being made available on an unrestricted basis. However, a comparable vector in a modified lambda gt11 phage is available commercially from Stratacyte of La Jolla, Calif. Other comparable vectors for the surface display of antibody Fab on a filamentous phage that grows in an *E.Coli* host are known may be available from William Huse, IXSYS, Inc. (San Diego, Calif.), Cary Queen, Palo Alto, Calif. (described in Chang, et al. (1991) *J. Immunol.* 10:3610–3614), and at the laboratory of Greg Winter, Cambridge University, England.

In FIG. 1, the pCOMB3 vector is shown in surface display and soluble Fab-producing forms. The XhoI and SpeI sites are provided for cloning PCR-amplified H chain Fd sequences. The SacI and XbaI sites are provided for cloning PCR amplified antibody L chains. The PelB leader sequences aid transcription and processing in the *E.Coli* host, with reading frames maintained. The parent sequence of the phagemid vector, pBluescript, which includes CoIE1 and F1 origins and a β-lactamase genes, has previously been reported. Digestion of pCOMB3 encoding a selected Fab with SpeI and NheI allows for the removal of the gill fragment, a M13 protein. Since SpeI and NheI produce compatible sticky ends, the digested vector may be re-ligated, yielding a phagemid that produces soluble Fab.

Figure 2:
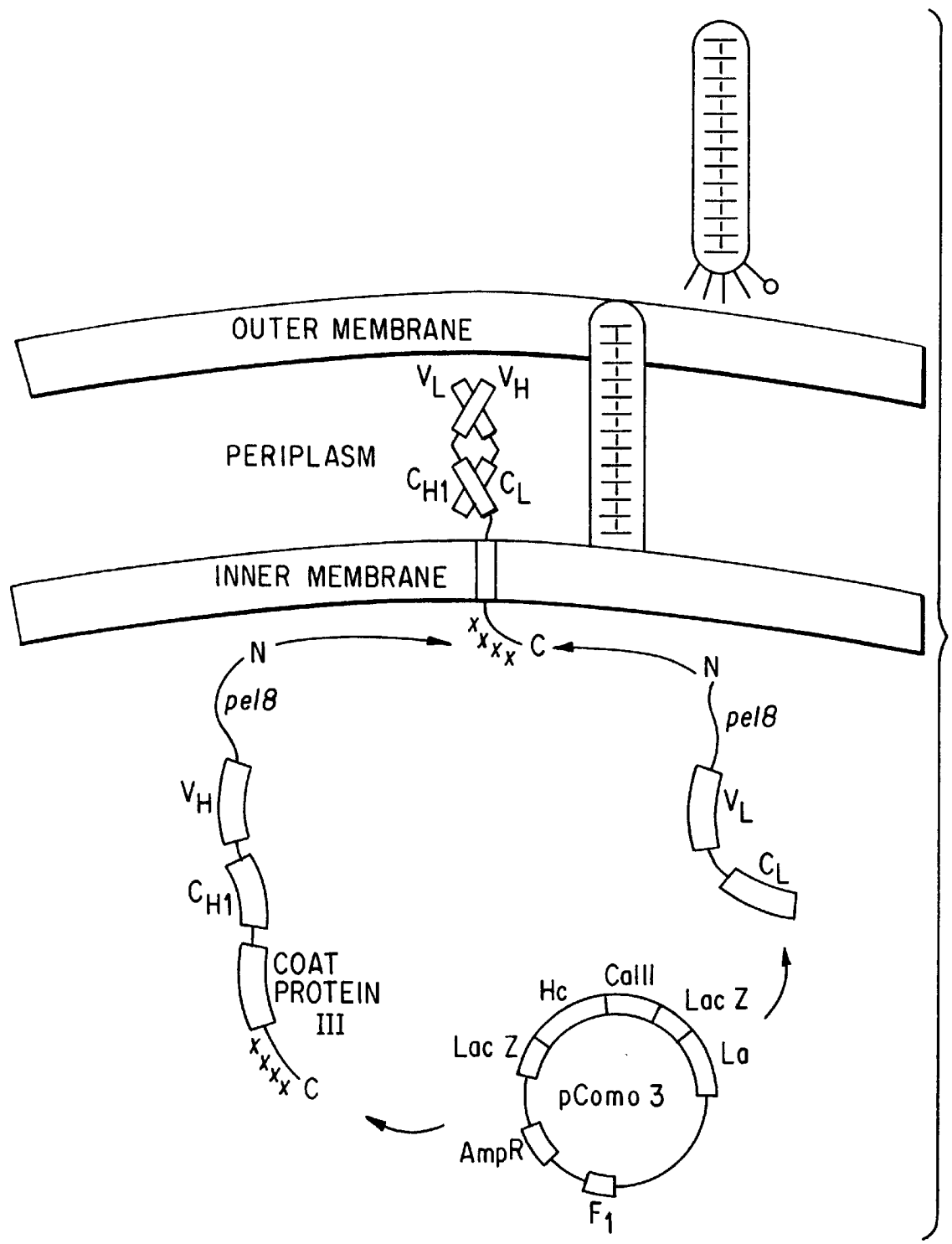
FIG. 2 diagrammatically illustrates the compositon of the pCOMB3 vector and the proposed pathway for Fab assembly and incorporation into the filamentous phage coat.

FIG. 2 illustrates the composition of the pCOMB3 vector and the proposed pathway for Fab assembly and incorporation into the phage coat. Expression of Fd/cpIII (H chain and M13 protein fusion product) and L chain is controlled by lac promoter/operator sequences. The chains are directed to the periplasmic space by pelB signal sequences which are subsequently cleaved. The H chain is anchored to the membrane by the gIII fusion, whereas the L chain is secreted into the piroplasm. The two chains are then assembled on the bacterial membrane. The Fab molecule is then incorporated into the M13 phage coat during exusion of the phage through the membrane via the cpiII segment (taken from the Barbas, et al. publication cited supra).

ii. Application to SpA.

As used with SpA, the vector was used to create a polyclonal combinatorial expression library from the peripheral cells of a healthy volunteer. Combinatorial libraries with gamma H chains were chosen for the determination of the basis of SpA binding for the following reasons: 1) This vector creates Fab without Fc regions so the screening methods are simplified; 2) with multiple V region primers and proven methods huge libraries (>$10^7$ H chains and >$10^7$ L chains) can be created to facilitate a highly rigorous examination of the effect of structural diversity on binding; 3) the vector facilitates the efficient creation of hybrid molecules with different H-L chain pairing, so the effects on binding can be determined; 4) the use of a gamma library allows the examination the effects of somatic replacement mutations on binding; and 5) these libraries offer an optimal source of cloned V genes for site specific mutagenesis experiments.

Antibody clones within the library that bind to SpA were selected and amplified using PCR according to means well known in the art. This process is the experimental equivalent of in vivo clonal competition for antigen, due to selection for the clones with the greatest binding affinity. Beginning from a library in which 0/30 random clones bound SpA, after three rounds of selection were performed wherein 27/30 random clones bound SpA strongly, as detected by incubation of bacterial lifts with $^{125}$I-SpA (see. FIG. 2), which detects only clones with high affinity for SpA.

Figure 3:
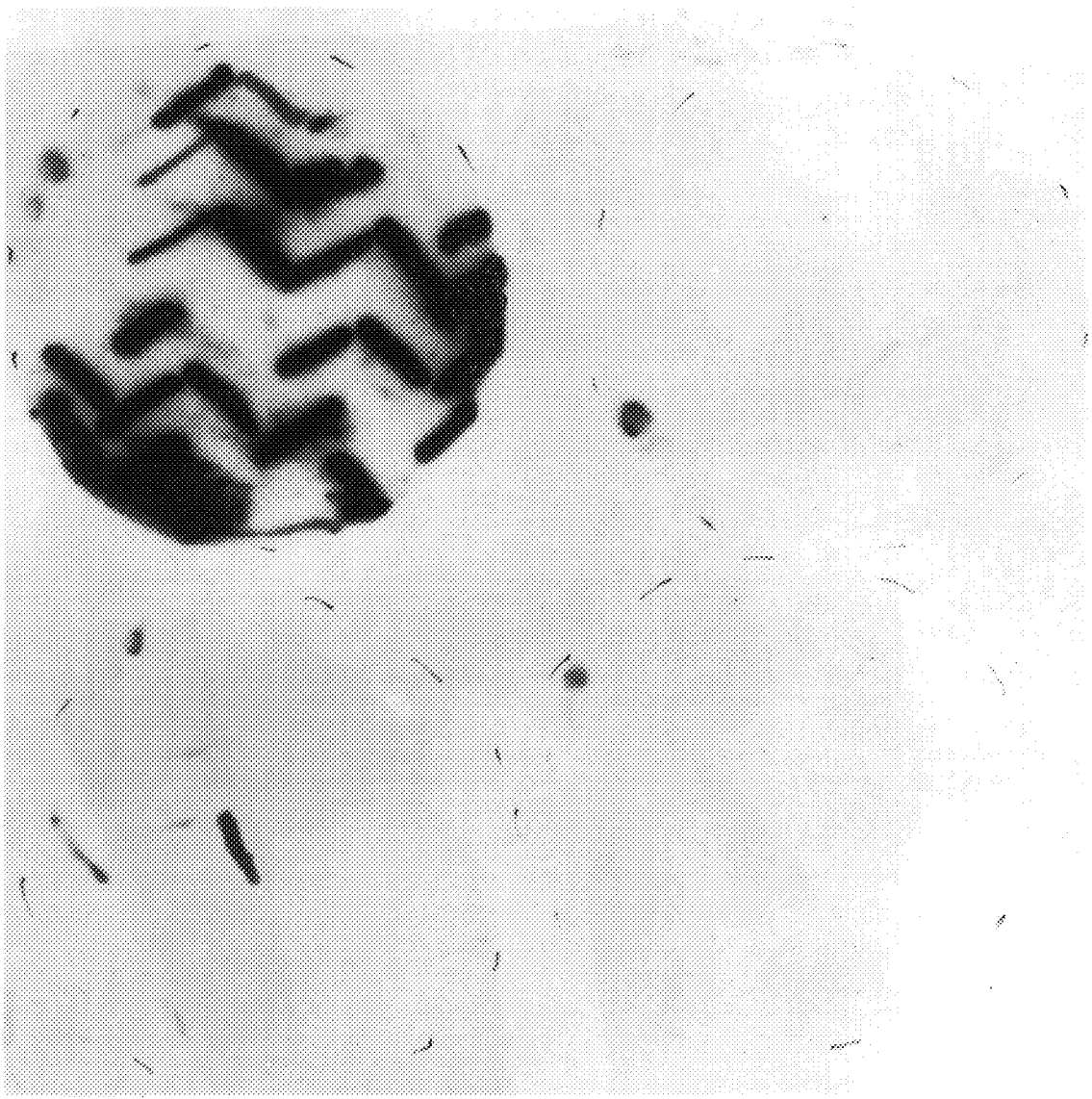
FIG. 3 is a reproduction of nitrocellulose fitters on which antigen-specific clones are identified by autoradiography after successive rounds of panning with hyperiodinated SpA.
Figure 8A:
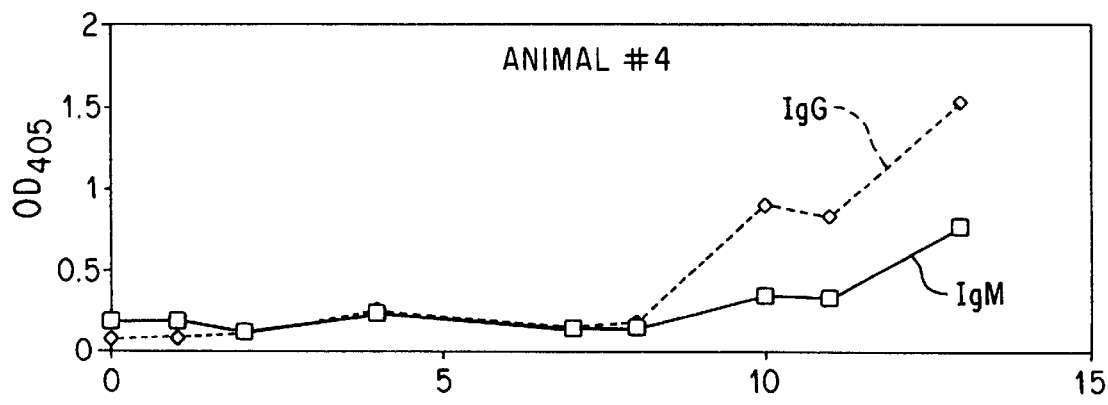
FIG. 8, A–C, depicts the results of an EUSA for the antibody response to mod-SpA immunization in Balb/c mice.
Figure 8B:
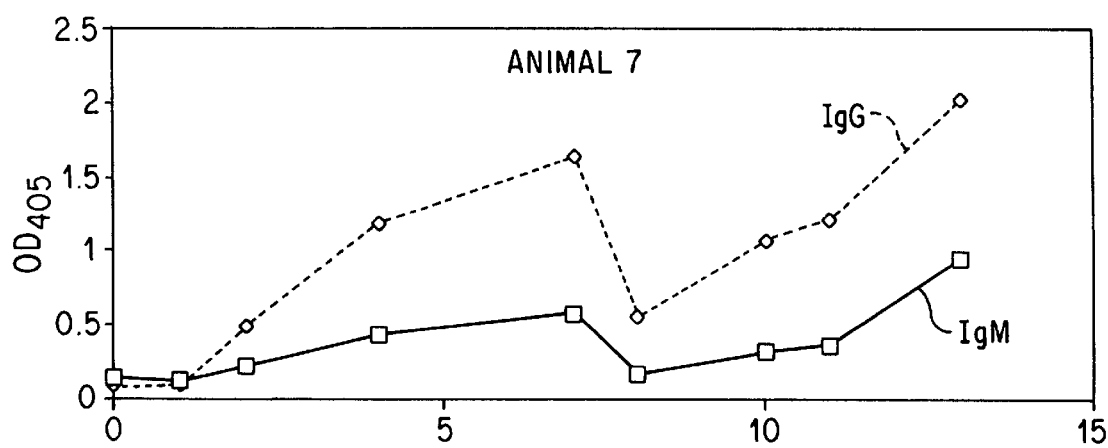
Figure 8C:
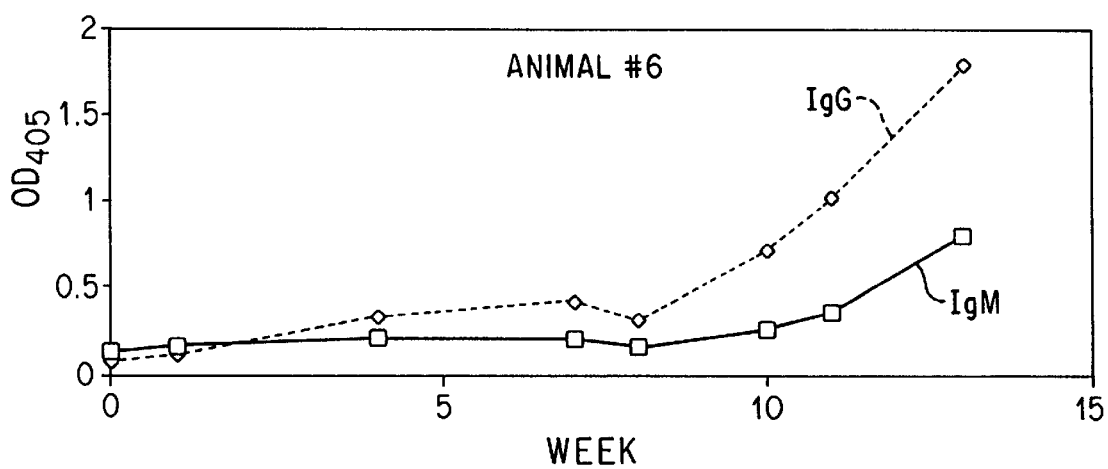
Figure 9:
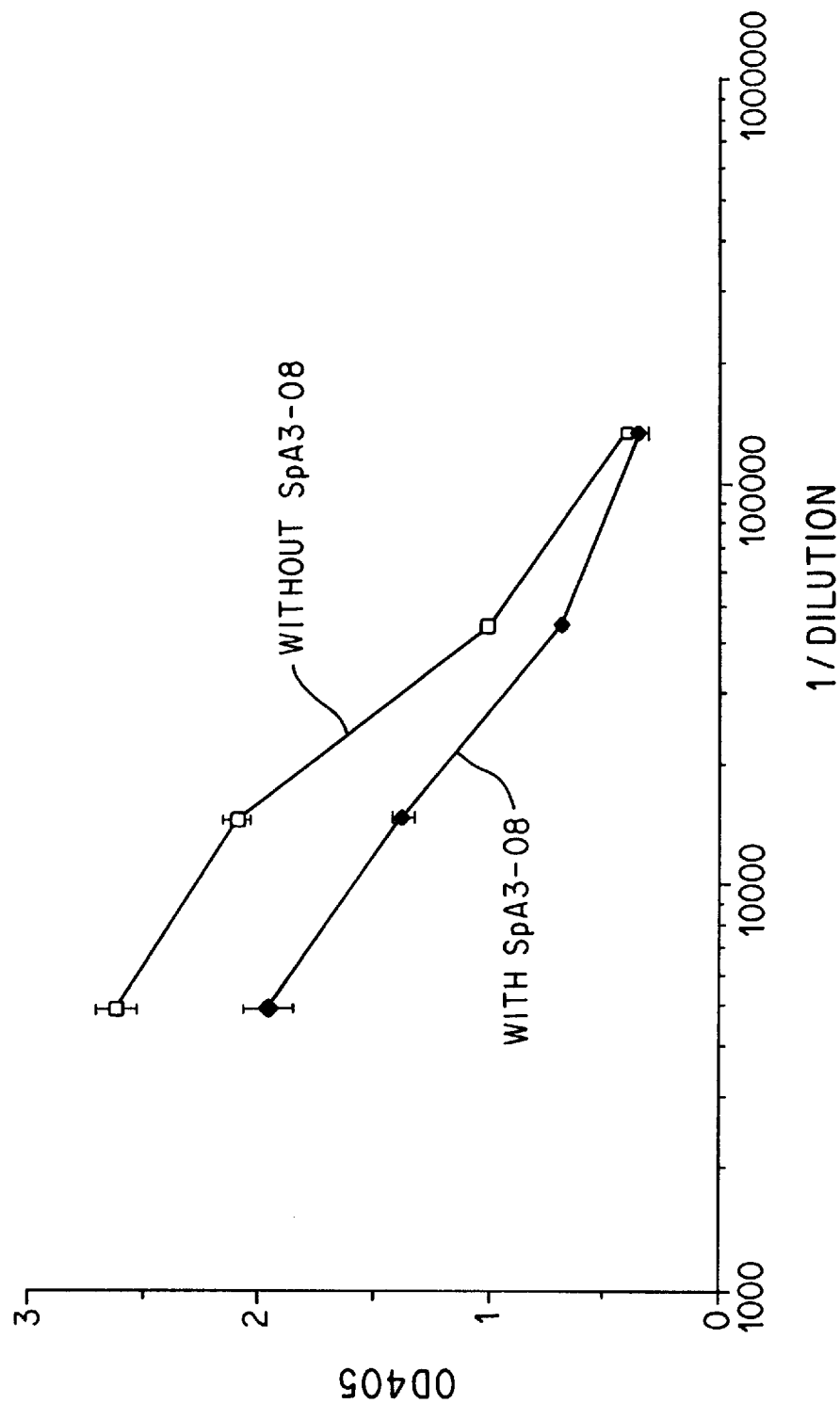
FIG. 9 depicts the results of an EUSA for inhibition of mouse Ig binding to mod-SpA by human V$_H$3 IgG Fab Sp A3-08.
Figure 10:
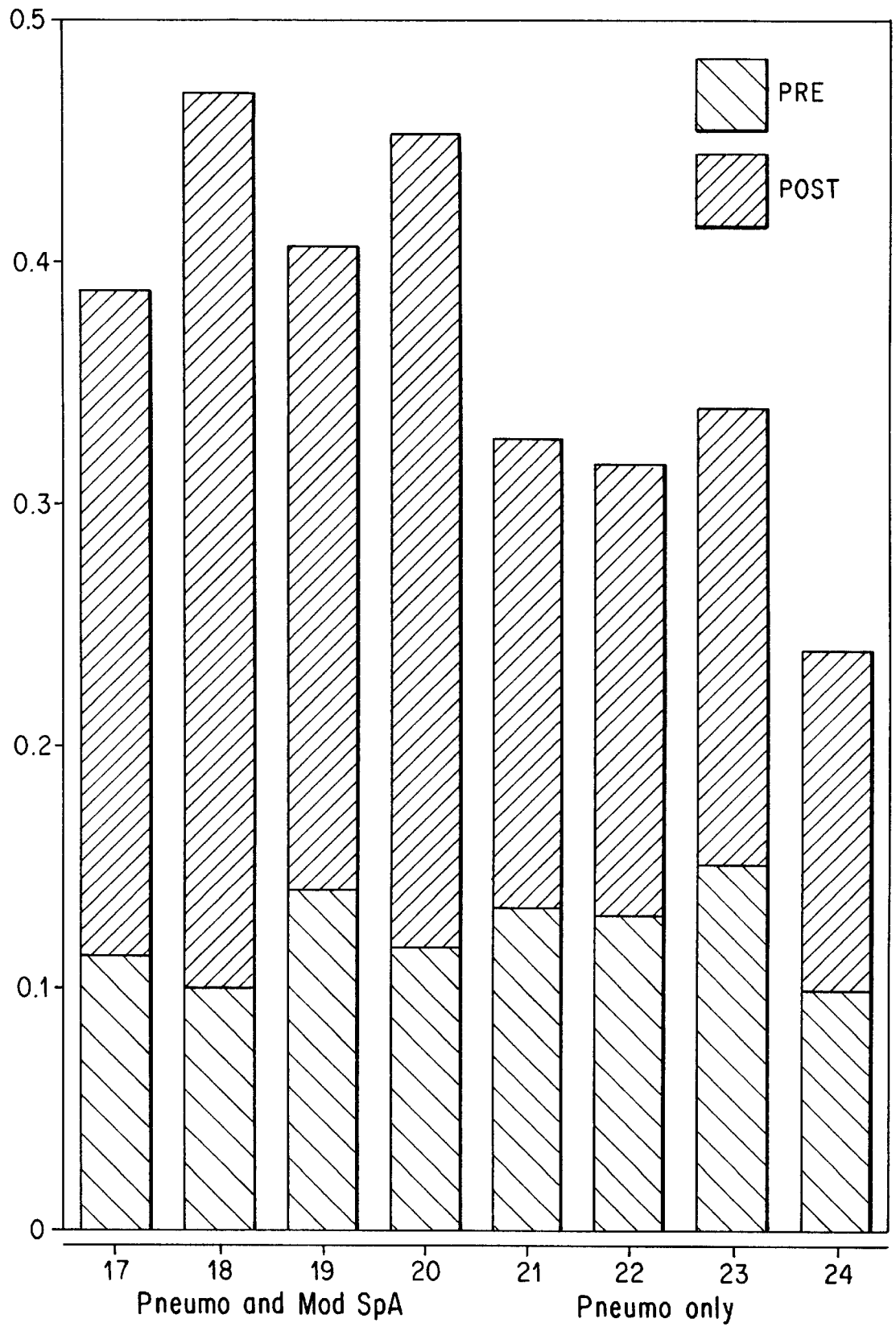
FIG. 10 depicts the results of EUSA's for the antibody responses to pneumococcal polysaccharide in mice immunized either with polysaccharide alone or polysaccharide and unconjugated mod-SpA. The terms Pre and Post in the FIGURE refer to antibody responses obtained before and after antigen priming.

Specifically, after induction with IPTG, colonies were lifted onto nitrocellulose filters, and positive clones were identified by using $^{125}$I-SpA (0.1 mc/ml; ICN Radiochemicals, Irvine, Calif.), using autoradiography. Positive colonies appear dark on FIG. 3. Randomly selected colonies from the original library are depicted at the upper left of the Figure. Colonies from the first round of panning are shown upper right Phage input was $2 \times 10^{11}$cfu, and $9.5 \times 10^5$cfu were eluted after the first panning (% yield=$4.75 \times 10^{-4}$). Colonies from the second round of panning are depicted at bottom right Phage input was $2 \times 10^{11}$cfu, with $5.3 \times 10^6$cfu eluted after the second panning (% yield=$2.65 \times 10^{-3}$). Colonies from the third round of panning are depicted at bottom left. Phage input was $2 \times 10^{11}$cfu, and after the third round of selection $9.5 \times 10^5$cfu were eluted (% yield=$4.75 \times 10^{-3}$).

It should be noted that the phagemid clones express only abbreviated gamma chains, which is devoid of the gamma second and third domains, so they do not express the Fc region identified by non-modified SpA. After prolonged exposure, in the original library none of the 30 dones bound $^{125}$I-SpA, while after one round of selection 1 weak binder of 30 clones was detected. After the second round of selection 7/30 clones had detectable SpA binding, and after the third round 27/30 clones bound SpA strongly.

Referring to Table III, it is shown that the composition of the original, unselected combinatorial library was compared to the libraries after three successive steps of selection with SpA and expansion. From 17 to 24 clones were randomly selected from each of the libraries after the gIII gene was excised. H chains and κ and λ L chain expression was detected by conventional sandwich ELISA. In addition, replicate slot blots with 200 ng of purified plasmid were probed with biotinylated oligonuceoties and a nonisotopic detection system (Tropix, Bedford, Mass.). For these studies control H chain genes of known sequence [7E ($V_H1$-gamma), 30P1 ($V_H4$-mu)] were used. To detect γ chain expression, the antisense sequence, GTCCTTGACCAG-GCAGCCCAGGG, designated gamma-CH1, from the first domain was used. Detection of $V_H$ families used sense oigonucleoaides from the third framework regions; of $V_H1$, 5'TACATGGAGCTGAGCAG(CG)CTGAGAT 3', designated $V_H1$-FW3, of $V_H3$,5'TATCT(TG)CAA(GA)T-GA(AG) CAG(TC)CTGA(ACG)A 3', designated $V_H3$-FW3, of $V_H4$, 5'TCCCTGAAGCTGAGCTCTGTGACCG 3', designated $V_H4$-FW3. Clones designated ?$V_H$ were identified by the gamma probe, but by none of the three $V_H$ family probes.

TABLE 3

|  | Original library (unselected) (N = 24) | SpA 1 (N = 20) | SpA 2 (N = 20) | SpA 3 (N = 13) |
|---|---|---|---|---|
| H-L pair | 15/24 (63%) | 11/20 (55%) | 14/20 (70%) | 13/17 (76%) |
| SpA Binders | 4/24 (17%) | 5/20 (25/%) | 14/20 (70%) | 13/17 (76%) |
| gamma | 19 | 19 | 20 | 13 |
| $V_H1$ | 5/19 (26%) | 1/19 (5%) | 0/20 (0%) | 0/13 (0%) |
| $V_H3$ | 5/19 (26%) | 11/19 (57%) | 19/20 (95%) | 13/13 (100%) |
| $V_H4$ | 5/19 (26%) | 6/19 (32%) | 1/20 (5%) | 0/13 (0%) |
| ?$V_H$ | 4/19 (21%) | 1/19 (5%) | 1/20 (0%) | 0/13 (0%) |

These data highlight that not all of the clones in the original library expressed both functional H and L chains, but this proportion increased by the third round of SpA selection. Data from the EUSA method of detection was more sensitive, and detected more SpA binders than the membrane lift method (displayed in FIG. 2). Significantty, we found that 17% of clones in the unselected library bound SpA, but with weak affinity (as measured by apparent $K_D$). After one round of selection this increased to 25% SpA binders. After the second and third round of selection this stablized at approximately 70%, and $K_D$ measurements demonstrated that there was an increase in average affinity amongst SpA binders with each round of selection. Of note, every SpA binder expressed both H and L chains, and used $V_H3$ encoded H chains, although both κ and λ L chains were used by different clones. This study rigorously confirmed the findings from the survey of isolated monoclonal Ig, which indicates that the "alternative binding site" of SpA is $V_H3$ restricted.

TABLE 4

Apparent affinities of isolated Ig and pCOME3 clones from SpA3 library.

|  | L CHAIN | $I_{0.5}$ ($10^{-3}$ M) | $K_D$ ($10^{-3}$ M)* |
|---|---|---|---|
| Purified Ig |  |  |  |
| Poly IgM | poly | 58.0 | 38.0 |
| Poly IgG Fab | poly | 13.0 | 16.0 |
| RIV (Mono IgM-$V_H3$) | $V_\chi$III | 140.0 | 45.0 |
| SpA3 Library |  |  |  |
| SpA3-18 | λ | 2.2 | 5.5 |
| SpA3-08 | λ | 4.4 | 12.0 |
| SpA3-37 | $V_\chi$III | 3.2 | 9.2 |
| SpA3-22 | χ | 8.7 | 6.6 |
| SpA3-40 | λ | 11.0 | 18.0 |
| SpA3-02 | $V_\chi$III | 13.0 | 28.0 |
| SpA3-39 | λ | 12.0 | 26.0 |
| SpA3-33 | $V_\chi$III | 22.0 | 46.0 |
| SpA3-13 | $V_\chi$III | 81.0 | 29.0 |
| SpA3-16 | $V_\chi$III | 24.0 | 32.0 |
| SpA2 Library |  |  |  |
| SpA2-13 | λ | 45.0 | 76.0 |
| SpA2-09 | χ | 6.7 | 3.7 |
| SPA2-14 | χ | 9.8 | 23.0 |
| SpA2-05 | χ | 7.0 | 12.0 |
| SpA2-18 | χ | 4.8 | 24.0 |
| SpA2-01 | χ | 20.0 | 16.0 |
| SpA2-07 | χ | 120.0 | 505.0 |
| SpA2-06 | χ | 11.0 | 14.0 |
| SpA2-17 | χ | 16.0 | 20.0 |
| SpA2-19 | χ | 1.3 | 6.7 |
| SpA2-02 | χ | ND | 48.0 |
| SpA2-04 | χ | 12.0 | 8.7 |
| SpA1 Library |  |  |  |
| SpA1-14 | χ | 17.0 | 11.0 |
| SpA1-19 | χ | 0.5 | 5.1 |
| SpA1-29 | λ | 19.0 | 49.0 |
| SpA1-30 | λ | 50.0 | 61.0 |

An inhibition ELISA was used to compare the apparent affnities of clones from the SpA3 library, with a monoclonal IgM $V_H3$ protein and a polyclonal IgM and IgG from adults; apparent affinity ($K_D$) was determined per the method disclosed in Friguet, et al. (1985) *J. Immunol. Methods* 77:305–319. These data (shown in Table IV) illustrate that the clones from the SpA3 library all have high affinity for the selecting antigen, SpA. Sequence comparison indicated that 5 of the 6$V_H$ sequences are likely clonaily derived, while the clone SpA3-33 represents an independent rearrangement, and likely derives from a different germline $V_H3$ gene (deduced amino acid sequences are included in Table II.A).

They are closest to the $V_H26c$ germline gene with less than or equal to 94% homology at a DNA level, which likely suggests that the true germline sources of these genes have not yet been reported. Data from Table III suggest that after three rounds of selection only clones with the strongest SpA binding affinity are represented, which explains why 5/6 $V_H$ clones are nearly identical. These clones use both κ and λ L chains. The binding affinity of these H chains for SpA when they use identical L chains may also be measured, so the effect of each amino acid substitution on SpA binding can be determined.

An additional source of non-diversified V gene segments may be developed from amplification and cloning of a genomic DNA library and >100 clones $V_H3$ genes from the same individual as the source of the previously described, peripheral lymphocyte library. To verify the integrity of this library, the sequences of four random clones are determined (here, W4, W8, W 11, and W12 included in Table II.A) representing new $V_H3$ germline genes. These V gene segments will have CDR3 and constant regions granted by overlap extension PCR, prior to insertion and expression in pCOMB3, for testing of SpA, or other candidate antigen binding.

The pCOMB3 vector was also used to clone the V genes expressed in a human B cell hybridoma line, designated CA4 (obtained from Dr. Alex Lucas, Oakland Children's Hospital). When these genes were cloned into the pCOMB3 vector, the resultant construct, termed PRP-12, was shown to have the same binding specificity for the capsular PS of *Haemophilus influenzae*, type b (Hib) as the parent cell line ($V_H$ sequence included in Table II). By inhibition ELISA according to means well known in the art, the parent IgG cell line, CA4, has an apparent $K_D$ for Hib PS of 2.4 $X1^{-9}M$, while PRP-12, the pCOMB3 clone that expresses these V genes, is $2.5 \times 10^{-8}M$. The lower affinity of PRP-12 for ligand, compared to the parent CA4 line, may be partly due to receptor valency. The V genes from this cell line were selected for further study for several reasons i) CA4 has binding activity for a conventional antigen, ii) this antibody uses a $V_H3$ H chain, iii) the parent cell line produced an antibody that is a $V_H3$ antibody of known sequence without SpA binding activity, and the bacterially expressed antibody also shares this property (as described above) and, iv) iii) the $V_H$ region contains a few highly unusual amino acid residue substitutions in the framework regions, which have not been previously described. Therefore the PRP-12/CA4 clone can be used to determine the effect of single point mutations on both a conventional and a superantigen binding capacity.

Step 3. Confirmation of the sAg activity of a candidate sAg in interactions with whole Ig bearing cells.

To confirm the sAg activity of a candidate antigen in interactions with Ig bearing whole cells, binding percentages can be determined using flow cytometric analysis. This method is described below in an example using lymphoid cells having IgM, IgG and/or IgD which are known to use a significant proportion of the $V_H3$ heavy chains (demonstrated in examples above to be the region which most prevalently binds the SpA sAg). it should be noted that this approach, and the resulting data, is also useful in determining whether particular sAg's can be used as lymphocyte phenotypic markers. Further, once the normal range of binding for a particular sAg is determined, the methods described below can be used to determine if variations from that binding pattern have occurred in a given B cell population.

For example, using the method below it has been determined that 14–50% of B lymphocytes in a healthy human individual will bind to the $V^H3$ restricted site on SpA. ft is known that a B cell malignancy (such as a lymphoma or leukemia) may be present if a large or dominant monoclonal V cell population is detected in the blood or in tissue samples taken from a patient. Therefore, in the presence of relevant diagnostic signs known to those skilled in the clinical arts, very low (e.g., 0–5% ) or very high (e.g., 80% or more) Fab-mediated binding of SpA by B lymphocytes from a human patient could indicate the onset or existence of a malignancy or the outgrowth of abnormal oligoclonal B cell populations in a patient who is suspected of having or being susceptible to developing a B cell malignancy.

As a representative example, the binding specificities of SpA, mod-SpA and Protein G (obtained commercially from Pharmacia LKB Biotechnology, Piscataway, N.J.) were compared. To perform the study, mod-SpA and Protein G were bictinylated according to means well known in the art and incubated with a suspension of human (mononuclear) tonsillar cells (MOAB's). Binding of mod-SpA and Protein G thereto was detected by flow cytometry; it will be appreciated that other means for detecting binding by a sAg or candidate sAg other than flow cytometry could be employed. It will also be appreciated by those skilled in the art that lymphocytes from peripheral blood and other lymphoid tissues, as well as lymphocytes from various species of interest could also be used in this analysis; for reference in this regard, analysis was also performed using umbilical cord blood (which is enriched in $V_H3$ B cells compared to adults).

As shown in FIG. 4, the results of this analysis for Protein G are shown in the left column, for SpA in the middle column, and for mod-SpA in the right column.

The percentages of cells reacting with bacterial antigen only (upper left quadrants), Moab only (lower right quadrants) or both bacterial antigen and Moab (upper right quadrants) are presented. The top row displays dual staining with a pan-T cell market (anti-CD3). None of the bacterial antigens bound to the CD3+ T cells. Instead, as shown in the second row, reactivity was restricted to the CD20+ B cell population. Subsets of IgM+ cells (third row), IgG+ cells (fourth row) and both kappa+ and lambda+ cells (fifth and sixth rows) were also observed to react with all three bacterial antigens. The quadrants were set using cells reacted with the isotype controls and the streptavidin-PE reagent. Non-specific binding was less than 1% (data not shown).

On a percentage basis, the values for binding with cells from either the CD20 B cell population or which bear IgM, IgD, IgG, kappa or lambda surface Ig are shown in Table V. These data were derived from dual staining studies to determine the proportion of CD20 staining cells which also stain a biotinylated bacterial antigen.

TABLE 5

| Inhibitor | Cord Binding | Cells % Inhibition | Tonsillar Binding | Cells % Inhibition | Protein G % Inhibition | SpA % Inhibition |
| --- | --- | --- | --- | --- | --- | --- |
| PBS | 31 | | 15 | | | |
| Human IgG Fab (polyclonal | 23 | 26% | 9 | 40% | 73% | 64% |
| Human IgM (Polyclonal) | 5 | 84% | 4 | 73% | 0% | 71% |
| Rabbit IgG (polyclonal) | 25 | 19% | 15 | 0% | 53% | 24% |
| SpA3-08 (monoclonal) | 7 | 77% | 4 | 73% | 0% | 0% |
| PRP-12 (monoclonal) | 26 | 16% | 0 | 0% | 0% | 0% |

TABLE 5-continued

| Tonsillar Cells Bearing: | Protein G Binding | SpA Binding |
|---|---|---|
| CD20 | 9% | 29% |
| IgM | 24% | 61% |
| IgG | 24% | 60% |
| K | 25% | 55% |
| λ | 33% | 59% |

TABLE 6

| $V_H$ Subset Expression after in vitro stimulatuion | | |
|---|---|---|
| | SRA | EBV |
| % B6-IgM | 30.0 +/− 8.4 | 10.6 +/− 4.0 |
| % G6-IgM | 1.4 +/− 0.6 | 5.5 +/− 2.1 |
| Ratio (%B 6-1 gM/% G6-1 gM) | 21.4 | 1.9 |

With respect to the MOAB's, these studies demonstrate that large subsets of both IgM and IgG bearing cells bind modified SpA (which is without Fc binding activity), likely due to the prevalence of $V_H3$ H chains on these lymphoid cells. SpA was bound by the largest proportion of B cells, with a lesser proportion of cells binding Protein G. Mod-SpA was bound by the smallest number of B cells. These differences in binding are consistent with the prediction that Protein G is only bound by cells with sIgG constant regions.

In contrast, SpA is bound to cells with the constant region of sIgG and/or certain $V_H3$ determinants, while mod-SpA is bound only to cells with certain $V_H3$ determinants. This model would, therefore, explain why SpA binds to a set of B cells that is roughly equal to the sum of the proportion of cells that bind to Protein G and mod-SpA separately.

In this particular study, triple staining studies were performed according to means well known in the art to determine the basis for binding of Protein G by 24% of IgM bearing tonsillar cells, because Protein G was believed to only bind to IgG. These studies demonstrated that all IgM bearing cells from tonsil identified by Protein G also coexpress IgG. Significantly, mod-SpA identified 33% of IgM cells, but only 20% of IgG bearing cells, which is in agreement with our binding data from isolated monoclonal IgG proteins. This observation confirms data from the evaluation of monoclonal Ig, by demonstration that a larger proportion of cells with sIgM than sIgG bind the alternative binding site of SpA. Therefore, not only are the structural correlates of binding of Fab to SpA unconventional, but the preferential association of SpA binding in IgM is also in conflict with the accepted paradigm of clonal maturation and expansion with isotype switch in response to a conventional antigen because after immunization with a conventional antigen, antibodies for the antigen are generally more common in the IgG pool than the IgM pool. In contrast, because without specific immunization, SpA binds to more IgM than IgG, it is an unconventional antigen.

To document the Fab and $V_H$ dependence of B cell staining with the bacterial antigens, the biotinylated antigens may be preincubated with different Ig preps prior to cell staining. The data for protein G and Mod-SpA binding to MOAB's are shown in Table V. These data illustrate that Protein G, which binds only to $F_{c\gamma}$, is inhibited by IgG but not polyclonal IgM. Binding of mod-SpA by tonsillar B cells is better inhibited by equal amounts (100 mcg/ml) of polyclonal IgM than polyclonal IgG, which is consistent with the impression that the average affinity of SpA binding in IgM is greater than IgG. Significantly, mod-SpA binding is not inhibited by preincubation with a monoclonal $V_H1$ IgG which is consistent with the notion that mod-SpA binding is not mediated via IgG constant regions, and that binding is mediated only via certain Fab that do not include the $V_H1$ family. In contrast, an Fab product of the PRP-12 clone, which expresses the CA4 anti-Hib PS antibody, did not inhibit. The demonstration that a monoclonal Fab that uses the appropriate $V_H3$ H chain SpA3-08 can significantly inhibit B cell binding, indicates that B cells bind to one or a very small number of components on the alternative binding site of SpA. The sequence encoding the SpA3-08 $V_H$ region is included in Table II.B.

To that end, mod-SpA is preincubated with phosphate buffered saline (PBS) or with polyclonal human IgM or IgG, polyclonal rabbit IgG or the affinity purified monoclonal Fab, SpA3-08 and PRP-12. in buffer for 1 hour at 4° C. at a final concentration of 100 mcg/ml. Referring to Table VI, the proportion of the total B cells bound by mod-SpA is displayed, and the percent inhibition (compared to without inhibitor) is in parentheses. B cells were identified by the CD19 marker. In these studies, the biotinylated mod-SpA reagent was titrated to the end of the plateau of the binding curve for human B cells. Then prior to cell staining, aliquots of mod-SpA were preincubated with either PBS (control), or potydonal human IgM or IgG, polyclonal rabbit IgG or the affinity purified monoclonal Fab, SpA3-08 and PRP-12 The SpA3-08 was isolated from a combinatorial library based on SpA binding (discussed above under Step 2) and the PRP-12 expresses the genes encoding the CA4 anti-*Haemophilus influenzae* type b antibody. The deduced $V_H$ regions of these antibodies are induded in Table II.A. The monoclonal $V_H3$ Fab, SpA3-08, inhibited >70% of binding to tonsillar and cord B cells, with greater inhibition of CD5-B cells than CD5+B cells. Only limited inhibition occurred with the $V_H3$ Fab, PRP-12.

Step 4. Confirmation of mitogenic activity of candidate sAg.

To confirm whether a candidate sAg can induce $V_H$ restricted lymphocyte mitogenesis, mononuclear cells from the species of interest are subjected to stimulation with the candidate and, for comparison, with a known mitogen (such as the Epstein-Barr virus).

Again, by example with respect to SpA, in vitro studies with umbilical cord mononuclear cells are performed. This source was chosen because it contains IgM bearing B cells and little or no IgG bearing B cells (so the influence of native SpA's reaction with IgG Fc would be minimized).

Aliquots of purified B cells are stimulated in vitro either with an extract of *Staphylococcus aureus*, Cowans strain I (SAC), that contains SpA, or with the T cell independent B cell mitogen, attenuated Epstein-Barr virus (EBV), B95-8, was used because the virus binds and stimulates B cells in proportion to their relative representation, and therefore V gene usage in EBV stimulated cells has been shown to be non-biased. The Ig composition of these supernatants are evaluated for the levels of two well characterized $V_H$ associated idiotypes, G6 and B6, which identify subsets of $V_H1$ and $V_H3$ products, respectively.

Mononuclear umbilical cord supernatants are harvested after 8 days of SpA/SAC stimulation and 28 days of EBV stimulation. The G6 and B6 idiotypes are measured by immunoassay using standard curves with the monoclonal IgM, Sie and Glo, respectively (sources are described in Silverman, et al. (1988) *J. Immunol Methods* 82: 469–475, and Crowley et al. (1990) *Mol. Immunol.* 27:87–94, which references are incorporated herein). All values are determined in mg/ml +/−SEM. Expression of the idiotypes on IgM after SAC/SpA and EBV stimulation are significantly different (P<0.05).

The results (shown in Table VI) demonstrate that, compared to EBV supernatant, SpA/SAC supernatant have a three fold enrichment in IgM that bear a $V_H3$ associated idiotype, and a four-fold depletion in IgM bearing a $V_H1$ associated idiotype ($\kappa^2$P<0.05). In contrast, L chain isotope usage after SpA/SAC or EBV stimulation does not differ significantly (data not shown). Therefore, the current data are consistent with SpA binding studies, and this preliminary data indicates that at a protein level the "polyclonal B cell activator", SAC, stimulates B cell populations with preferential $V_H3$ gene usage. In vitro activation with SpA appears to require co-stimulation from T cells and/or cytokines, a mechanism analogous to the superantigen-properties of staphylococcal T cell.

Step 5. Determination of the earliest point in development in which B cells bind Ig [using SpA example].

To best assess the possibility that SpA, or an equivalent superantigen, may be able to influence repertoire acquisition, the earliest stage of B cell differentiation that certain B cell subsets may interact with these agents, should be determined. Certain pre-B cells have both cytoplasmic H chains and low density surface expression of fully rearranged VDJ-mu chain in association with a surrogate L chain. The functional capaity of this complex is unknown, but molecular modelling studies suggest that the pocket made up of folded hypervariable regions may be obscured in these pre-B cell sig surrogates, while the region made up of the $V_H$ FW1 and FW3 is surface exposed. While the $V_H$ distribution of pre-B cells from healthy individuals is unknown, at least 50% of the rearrangements in fetal libraries from pre-B cells, and 40–60% human pre-B cell leukemias use $V_H3$ genes, therefore these genes are commonly expressed in physiologic and pathologic examples of early stages of B cell development. Moreover, these studies are important, because antigens with the ability to stimulate B cells at this eary proliferative phase would likely have much greater potential to skew the immune response.

To determine whether SpA can interact with cells at this stage, microfluorimetric studies of pre-B cell lines are performed. Several human pre-B cell lines are available from independent investigators for correlation of SpA binding and $V_H$ expression (See Tsubata, et al. (1990) *J. Exp. Med.* 172:973–976; Rolink, et al (1991) *Cell* 66:1081–1094; and Nishimoto, et al., (1991) *Proc. Natl. Acad. Science USA* 88:6284–6288). In addition, to isolate normal early lymphoid progenitors from bone marrow, microfluorimetry can be used to sort CD34+ cells, or a commercially available anti-CD34 column (CellPro Inc., Bothell Wash.) can be used. In bone marrow, CD34 enriched populations have two subpopulations-larger cells (i.e. increased SSC and FSC) that are CD10 that represent myeloid cells, and smaller cells that are CD10+ that represent lymphoid precursors. This latter populations of lymphoid cells contain the majority of terminal deoxynucleotidyl transferase cells and include pre-B cells. And, although these cells represent less than 1% of marrow cells, adequate numbers of purified cells should be available to test the hypothesis that certain pre-B cells bind mod-SpA by a surrogate Ig complex.

These samples are characterized for the expression of monocytic and myeloid markers, and CD20 (a marker for more mature B cells). Then, binding of biotinylated SpA, modSpA and Prot G are assessed in comparison to CD19 and Sig markers.

To corroborate these studies, $^{125}$I-surface labelling of cells is performed, followed by precipitation with superantigen, using published methods (see, Nishimoto, supra). Briefly, cells are labelling and then incubated with mod-SpA (or another microbial antigen), then washed and the cells are lysed in the presence of digitonin and protease inhibitors. The precipitants are then sedimented and washed. The precipitated materials are run on reducing and non-reducing PAGE gels, to demonstrate the characteristic MW of the precipitating surrogate Ig complex. The origin of the $V_H$ region is also determined, by immunoblotting of the precipitated complexes with the previously described anti-peptide antibodies to the mu constant region and V families. In addition, control precipitations may be performed using anti-mu antibodies (as a positive control), and anti-kappa or anti-gamma antibodies (as negative controls).

Step 6. Cofactor requirements for in vitro stimulation with SpA.

To determine the cellular requirements for activaion by sAg (in this example, recombinant SpA), a series of in vitro stimulation studies will be performed. In particular with respect to SpA, this is necessary because highly purified B cells are not stimulated by SAC, and similarly, B cells are not stimulated by recombinant SpA alone. Therefore, to determine the minimum requirements for cofactors to provide the second signal during in vitro stimulation, activation with recombinant SpA and control Ig binding proteins, in comparison with SAC and other T cell independent B cell mitogens should be assessed.

To investigate the capacity for SpA and SAC to cause the selective proliferation of B cells, certain recently reported methods may be adapted to this end (see, Whisler, et al. (1991) *Lymphokine Cytokine Res.* 10:1–6; and Boumpas, et al. (1990) 145:2701–2705). As described, mononuclear cells are first separated by a Ficoll gradient, then they are first depleted of monocytes and NK cells by incubation using 5 Mm L-leucine methyl ester HCL (Sigma) in serum free RPMI (tissue culture media). The cells are then washed and incubated twice with treated sheep red blood cells. To isolate B and T cell enriched fractions the non-rosetting and resetting fractions are separated by diatrizoate/Ficoll gradients, respectively. The sedimented rosette forming ceiling from the first centrifugation are treated with isotonic $NH_4Cl$ to lyse the SRBC, and the cells are then analyzed with OKT3 (T cell marker), CD19 (B cell marker) and CD16 (NK cells) to evaluate purity. Residual contaminating cells can be removed by treatment with the appropriate antibody and complement.

Proliferation studies are performed using formalinized SAC (Sigma) or *Staphylococcal aureus* Wood strain (that is devoid of SpA), the T cell independent mitogens; EBV and phorbol esters (PMA), anti-IgM on sepharose beads, which will be compared with recombinant Ig binding proteins, SpA (Calbiochem), mod-SpA or Protein G. Significantly, by themselves, recombinant SpA and Protein G alone are devoid of mitogenic activity, and earlier reports of mitogenic potential have subsequently been ascribed to contaminants. While there is conflicting data concerning the mitogenic potential of soluble anti-human IgM, there appears to be concordance that by proliferation criteria, as well as by biochemical evidence of action (e.g. phosphorylation of tyrosinated proteins and polymerization of cytoskeletal actin) that goat anti-human IgM crosslinked to acrylamide beads is a more potent stimulant.

Even in the absence of class II molecules, T cell superantigens bound to beads have been shown to be potent in vitro T cell stimulants, therefore, for a similar rationale, in vitro stimulation studies should be performed to assess activity with the Ig binding proteins coupled to beads. If mitogenic activity with a recombinant product is detected without the addition of cytokines, control studies should be performed to evaluate for possible endotoxin contamination.

Cultures will be performed without the use of T cells, as studies with equivalent methods have demonstrated that recombinant IL-2 (10–20 u/ml)(Cetus, Emeryville, Calif.) alone, or in combination with IL-4 (100 u/ml)(Genzyme, Boston Mass.) can provide the "second signal" B cell proliferation. Available data suggest that proliferation does not require other cytokine factors, but the results of initial experiments will determine the need for IL-1α, IL-6 and/or IL-7. Replicate cultures can be performed with 100 ul or 1 ml cultures of mononuclear cells at $10^6$ cells/ml incubated with filtered supernatants from attenuated, B95-8 marmoset lymphoblastoid cells in 48 well polystyrene culture trays (Costar, Cambridge, Mass.) diluted 1:2 with fresh supplemented medium. All studies should be performed in replicates, with noninfected wells as controls.

Proliferation will be assayed using methods known to those skilled in the art, by incubating the cells in medium supplemented with 1 uM [$^3$H]-thymidine, with harvest onto glass fiber paper, and [$^3$H]-TdR incorporation determined by liquid scintillation spectroscopy. The time course of proliferation will be determined. Taken together, these methods will determine whether the stimulation of B cells by recombinant SpA has different requirements, or induces a different level of activation, than stimulation with EBV, PMA or by cross-linking of antigen receptors by anti-Ig.

Step 7. Comparison of the repertoire induced by in vitro stimulation with SpA to other polyconal activators.

Whether the subset of B cells that responds to in vitro stimulation with a sAg (here SpA) are restricted by their surface expression of $V_H$ regions can also be evaluated, to determine if SpA causes a preferential stimulation of $V_H3$ B cells compared to unstimulated or mitogen stimulated controls. To determine whether various B cell mitogens induce subsets of B cells with different V gene usage, methods to assess V gene expression at both an RNA and protein level will be used. To assess the stimulation of different B cell subsets at an mRNA level, after stimulation, $10^7$ cells are pooled, washed and sedimented, and the RNA extracted by the alkaline lysis-guanidium isothiocyanate method. Northern blots are performed using either labelled-FW oligonucleotides or nick translated full length $V_H$ family specific probes. Alternatively, the method of quantitative PR C described by Braun and coworkers can be utilized.

Briefly, to determine the representation of $V_H$ families, the RNA is used to make cDNA by using an oligo-dT primer and reverse transcriptase. $V_H$ family specific FW1 primers and an anti-sense $^J$H consensus primer are utilized in application reactions, with quantitation by use of amplification with Taq polymerase and dNTP that include $^{32}$P-[α]-CTP. Samples are titrated so that the initial template represents >100 copies of from each $V_H$ family, with comparisons to cloned V gene standards in plasmids. Equivalent volumes from amplifications using each of the $V_H$ primers are then run on agarose gels, and stained with ethidium bromide, then quantitated by counting in a scintillation counter. As described in the preliminary results sections, a large panel of cloned cDNA rearrangements for different V regions are available as positive controls for these studies.

For small scale purifications, the Ig from the supernatants is purified by incubation with immunosorbent beads with anti-human Ig (Biorad, Richmond Calif.). In control studies, incubation of 10 ul of these clean washed beads with supernatant overnight at 4° C., binds greater than 15 mg of Ig. Then, the beads are washed with 0.05% Tween-20/PBS, then reducing buffer is added (2M and 8M urea), and the denatured Ig solution is loaded onto SDS-polyacrylamide gels, for immunoblot analysis of V region usage in H and L chains. Therefore, by comparison of supernatant from cells stimulated with different mitogens, this approach should effectively demonstrate the V region usage of responder populations.

Taken together, data from this method should demonstrate whether B cells stimulated by recombinant SpA, and SAC, express a different usage of V regions than stimulation with EBV, PMA or by cross-linking of antigen receptors by anti-Ig.

It will be appreciated by those skilled in the art that modifications of the above-described steps may be desirable depending on the intended end use of the sAg. For example, binding studies using B cells from different age populations (in particular neonatal, juvenile and elderly populations) will be desirable where the expected use for the sAg is as a carrier or adjuvant in a vaccine intended to enhance the immune response of individuals in these populations. In addition, experimental protocols known to those skilled in the art to be equivalent to those outlined above may be utilized to identify candidate sAg's having the characteristics described herein.

Further, toward constructing a specifically reactive vaccine, or to identify for other purposes which genes and amino acid residues correlate with the unconventional binding sites of the sAg, molecular cloning and expression of rearranged $V_H$ genes and oligonucleotide directed site-specific mutagenesis may be used to detect which genes and residues are critical for binding. To the same end, the cloning and expression method described above can be used to evaluate the effects on antigen binding of CDR regions of different size and composition.

C. IDENTIFICATION OF AN ANIMAL MODEL TO ASSESS WHETHER IN VIVO EXPOSURE TO B CELL sAg SKEWS THE REPRESENTATION OF IG VARIABLE REGION GENE FAMILIES.

Once a B cell sAg is identified, an animal model will be selected to demonstrate that the sAg increases the immunogenicity of bacterial and/or viral polysaccharides and/or glycoproteins in vivo.

By way of example, a murine model is appropriate for use in in vivo studies with SpA, in particular to predict the utility and function of SpA as a superantigen in an immunization protocol performed according to the method of the invention in humans for the following reasons. Murine $V_H$ families J606 and S107 are highly homologous to members of the human $V_H3$ family. Further, Fab of antibodies from these murine families bind SpA, while products of other families do not. Also, antibodies from these families have been shown to be preferentially used in formation of anti-polysaccharide antibodies on immunization with polysaccharide—containing pathogens. Specifically, the vast majority of hybridomas made in Balb/c mice against the capsular polysaccharide of the group C menigittidis use one of a small number of $V_H$ gene segments from the J606 family.

Moreover, as shown in more detail in Example II, immunization of adult Balb/c mice with recombinant, endotoxin-free mod-SpA causes an increase of circulating Ig that bind mod SpA, with recognition at or near the same binding site on SpA which is recognized by human $V_H3$ Fab. The immune response to SpA in mice can therefore be expected to be substantially analogous to, and predictive of, the response which would be achieved to immunization with the same antigen in humans. These data indicate that the mouse would be a good animal model for in vivo studies with the SpA sAg for use in a human and with the SpA conjugate vaccine in particular.

In contrast, data derived from binding studies using rabbit Ig and analysis for sequence homology with human $V_H$ regions of known rabbit $V_H$ genes indicate that rabbit antibodies do rot interact with SpA as strongly as human and murine antibodies. Consequently, it does not appear that the rabbit would serve as well as the mouse as an animal model for studies of this particular sAg. However, it will be apparent to those skilled in the art that application of the same analysis to gene sequence homologies of other species with $V_H$ regions in humans, combined with data concerning binding of other sAg, may indicate that other species would serve well as animal models for use in studies of sAg other than SpA identified according to the methods disclosed herein.

D. CONSTRUCTION OF A B CELL sAg CONJUGATE VACCINE OR COMPOSITION AND USE THEREOF IN IMMUNIZATION.

1. In vivo experimentation protocols.

Using an animal model (e.g., the murine model for use with SpA), preparations of the identified B cell sAg conjugated to a polysaccharide or glycoprotein derived from a bacterial or viral pathogen's capsule or cell wall are administered in vivo. First and generally, the sAg alone is administered and the Ig levels of the model subjects monitored to determine that they subsequenty retain intact B cell and T cell-mediated immune responses and are not immunosuppressed. Then, a series of studies which separately use conjugated and concomitant administrations of sAg and the polysaccharide or glycoprotein are performed using different sizes of the polysaccharide (i.e., different-sized oligomers) and glycoprotein, and different molar ratios of polysaccharide/glycoprotein to sAg to define the optimal composition for immunogenicity, which is established by measurement of serum antibody titer to sAg and polysaccharide or glycoprotein.

In addition, with particular reference to SpA, native, recombinant and modified forms (i.e., the latter with IgG Fc binding activity eliminated) are separately used (alone and with the pathogen polysaccharide or glycoprotein as described above) to determine which forms are best used as the carrier or adjuvant in the inventive vaccine or composition (i.e., the composition for concomitant administration of SpA and the polysaccharide or glycoprotein components). It is expected that a modified, recombinant form of SpA will be the preferred form for this purpose.

Control animals should be immunized with conjugate vaccines using a conventional carrier protein, such as dipheria or tetanus toxoid. Efficacy of the SpA conjugate and control vaccines should be determined in juvenile and elderly mice, which are analogous to the human populations most likely to receive the vaccine.

Preferably, the animal model study would be designed so there would (statistically) be a 95% chance of detecting a 50% increase in the representation of the predicted $V_H$ family restricted antibodies after stimulation by the sAg/component conjugate or composition. For example, where SpA is the sAg and it is used with the murine model, a 50% increase from the baseline representation (15%) of J606 and S107 restricted antibodies would be the target for the study.

Assuming a standard deviation of 30% of mean, or unstimulated baseline of $15^+/-4.5\%$, at least 11 animals present in the control and test groups would be required to detect the target increase (at 95% probability) would be chosen to achieve a statistical valve of $15^+/-4.5\%$ to 22.5%, with a $P<0.05$. The preferred method for determination of $V_H$ distribution and Ig binding specificity is to use a colony hybridiaation technique with removed splenocytes reported in Kelsoe, et al. (1987), *Methods in Enzymology*. "Cloning of mitogen—and antigen-reactive B lymphocytes on filter paper disks: phenotypic and genotypic analysis of B cell colonies", pp. 287–304, and Schulze, et al. (1987) *J. Exp. Med.* 166: 163–172, the disclosures of which are incorporated herein by this reference. In particular with respect to the use of a murine model, it will be appreciated that baseline data on the normal distribution of $V_H$ families of BALB/c mice at different ages have been reported and are known in the art.

Specifically preferred protocols for (1) determining the extent of enhancement of the immune response by SpA and mod-SpA in BALB/c mice, and (2) the immunogenicity of different conjugate or preparations (or compositions for concomitant administration) in Balb/c mice proposed for use are:

For the first determination, using SpA, mod-SpA and a saline control, 3 groups of adult 96 week old female BALB/c mice (with 12 animals in each group) will be immunized so 12 mice receive SpA, 12 receive mod-SpA and 12 receive saline subdermal injections. Prior to immunization, eye bleeds of 250 ul will be obtained from each animal. Then each animal will be immunized subdermally with 0.5 ml of saline, or saline with 100 mcg of SpA or saline with 50 mcg of mod-SpA. Thereafter, on weekly intervals, eyebleeds will be obtained. The study will be continued for at least 6 weeks, or until values return to baseline.

To demonstrate the result of immunization, the blood cells can be separated from the plasma, and analyzed separately. The blood cells will be analyzed by flow cytometry for binding to SpA-biotin and mod-SpA coordinately with analyses for a pan T cell marker, CD3-$_\epsilon$ (Clone 145-2c11, Pharmingen, San Diego, Calif.), or a pan B cell marker, Ly5-T (clone RA3-6B2, Pharmingen), and a B cell actlaor. These studies will determine whether SpA and a mod-SpA binding increases after immunization, and whether these cells then display the phenotype of activation. It will also demonstrate the kinetics of the cellular response.

The plasma from these bleeds will be tested by ELISA for binding to mod-SpA. In these tests the mod-SpA at 10 mcg/ml in phosphatase buffered saline (PBS) will be incubated on the precoat of EIA microtiter plates (COSTAR. Boston, Mass.) overnight at 4° C., then blocked for 1 hr with 1% bovine serum albumin in PBS. Serial dilutions of the plasma are added which are diluted in PBS for 2 hours at 15°–37° C., then washed 4 times with 0.05% (v/v) Tween20 in PBS, then incubated with alkaline phosphatase labeled anti-mouse IgM or alkaline phosphatase labeled anti-mouse IgG for 1 hour at 37° C., then washed 4 times, and developed with substrate. Parallel assays will use precoats of affinity purified goat anti-mouse IgM or affinity purified goat anti-mouse IgG so enrichment or depletion of the proportion of IgM of IgG Fab reactive with mod-SpA can be detected.

Alternatively, adult female Balb/c mice may be immunized either with 50 mcg of recombinant SpA, or with 50 mcg of modified (non-IgG Fc binding) recombinant SpA, and a control non-immunized group. From days to weeks subsequently, the spleens will be harvested, and single cell suspensions cultured in supplemented RPMI-1640. Cultures of 200–20,000 splenocytes in 5 ml of media, with feeder cells of thymocytes depleted of B cells at $1-5 \times 10^7$ cells/ml are overplayed on Whatman 54 filter discs (8.26 cm diameter). Colonies are grown for 5 days, and then treated with LPS, which causes a non-selective induction of RNA expression.

To detect colonies with high cytoplasmic mRNA, light microscopic evaluation of the formalin-fixed colonies after methyl-green pyronine staining with Wright/Giemsa counterstain will be used. The colony containing filter is sequentially overplayed with replicate filters, which are used either for V gene, $C\mu$ or $C\gamma$ probe hybridization, or alternatively, the filters can be immunochemically evaluated with anti-Ig, anti-idiotypic antibody or with biotinylated SpA. Serial hybridizations of each lift with three different nick-translated probes can be performed, without substantial loss of signal. Animals may also immunized with bacterial proteins without using LPS in vitro with the cultured splenocytes. Therefore, as a complement to the previously described method which determines the total $V_H$ distribution of B cells present in the spleen, by omission of LPS the distribution of $V_H$ region expressed by in vivo activated B cells can be determined.

For the second determination, mod-SpA is conjugated to the purified pneumococcal capsular polysaccharide, Type 14, (American Tissue Type Collection), using the conjugation method described by Peters, et al. using native, undigested polysaccharide. The conjugate is fractionated by size and the ratio of protein to polysaccharide is determined, as described previously herein.

As a starting point, the immunogenicity of preparations with 1:1 molar ratios of protein to polysaccharide are tested. Thereafter, the purified conjugate vaccines will be administered to groups of mice as described above, with the groups immunized with amounts of vaccine containing 50 mcg of protein equivalent. The groups will be immunized with control (saline), SpA-conjugate, mod-SpA, and purified polysaccharide alone. Although at present there is no FDA approved protein conjugate vaccine pneumococcal vaccine, experimental conjugate vaccines from commercial sources may also be compared.

Response will be measured by ELISA according to means known in the art for anti-polysaccharide antibodies using a precoat of purified polysaccharide, and the proportion of anti-polysaccharide antibodies reactive with mod-SpA will be detected using a precoat of polysaccharide and detecting with biotinylated mod-SpA then developing with streptavidih-alkaline phosphatase, to determine what proportion is dually reactive. Antibody levels will also be measured by standard RIA.

Subsequently, the protocol is repeated with a new set of mice to determine the effect of using polysaccharide of different oligomer sizes, changing the protein to polysaccharide ratio, and changing the dose a the immunogen. We will also test the effect of using combinations of superaridgen and polysaccharide that are not chemically coupled.

Following all protocols, splenic colony hybridization assays will be performed to document that B cell expressing S107 and J606 VH families, the murine equivalent of the human VH3 family, are the B cell subsets that are modulated in size by immunizaion. This approach may also be taken to develop vaccines for other polysaccharides and glycoproteins.

For a specific comparison of the in vivo response in adult mice to pneumococcal polysaccharide with and without the presence of recombinant, endotoxin-free mod-SpA, see Example III. As shown in the example, the mice produced higher titers of Ig reactive with the pneumococcal polysaccharide when immunized with both the polysaccharide and modSpA than were produced on immunization with the polysaccharide alone. These data indicate that co-administration of mod-SpA and a polysaccharide can influence the resultant response to the polysaccharide, even without chemical conjugation of the sAg to the polysaccharide immunogen.

2. Construction of sAg vaccine or composition

The inventive method utilizes a vaccine is a chemical conjugate between a polysaccharide or glycoprotein from a bacterial or viral source and the sAg. Alternatively, these components may be administered concomitantly in a composition where in the components are not coupled. (see e.g., the comparative data produced using a pathogenic immunogen alone versus that immunogen administered concomitantly with unconjugated mod-SpA in Example III).

Table VII lists infectious agents with pathogenicity for man which contain components for use in the inventive vaccine. It will be appreciated by those skilled in the art that this list is not exclusive; other human pathogens and infectious agents with pathogenicity for other species may also be appropriate for inclusion in the vaccine of composition preparation if they are identified as having polysaccharide or glycoprotein components which are suitable immunodominant targets.

TABLE 7

| | Diseases |
|---|---|
| | Bacteria |
| Bacillus anthracis | anthrax |
| Bordetella pertussis | whooping cough |
| Borrelia | a family of disease, including Lyme disease and relapsing fever |
| Campylobacter ieiuni | gastroenteritis |
| Clostridium botulinum | botulism |
| Corynebacterium diphtheria | diphtheria |
| Escherichia coli | many strains that produoe varied diseased, including diarrhea and urinary tract infections; some strains are not virulent |
| Haemphilus influenzae | meningitis, epiglottitis, sinusitis, pneumonia, middle ear infections |
| Helicobacter pylori | gastritis, duodenal ulcer diseases |
| Legionella pnemophila | Legionnaires' disease |
| listeria monocytogenes | meningitis, sepsis |
| Mycobacterium lepraie | leprosy |
| Mycobacterium tuberculosis | tuberculosis |
| Neisseria gonnorrhoeae | gonorrhea |
| Neissena meningitidis | sepsis, meningitis |
| Norcadia ateroides | lesions of the respiratory tract |
| Pseudomonas aeruginosa | infections of compromised hosts, nonsocomial infections |
| Rickettsia | Rocky Mountain spotted fever, typhus (rare) |
| Salmonella | typhoid fever, enteric fever, gastroenteritis |
| Shigella | dysentery |

TABLE 7-continued

| Diseases | |
|---|---|
| Staphylococcus aureus | impetigo, boils, soft tissue and systemic infection, osteomyelitis, toxic shock syndrome |
| Streptococcus pyogenes | pneumonia, sinusitis, meningitis, otitis media |
| Streptococcus pyogenes | rheumatic fever, soft tissue infection, pharyngitis |
| Treponema pallidum | syphilis |
| Vibrio cholerae | cholera |
| Yersinia pestis | bubonic plague |
| Yersinia enterocolitica and pseudotuberculosis | mesenteric lymphadenitis |
| Viruses | |
| cytomegalovirus | mononucleosis |
| dengue virus | dengue fever |
| Epstein-Barr virus | mononucleosis, Burkitts lymphoma |
| hepatitis B virus | hepatitis |
| herpes simplex type 1 | encephaitis, stomatitis |
| herpes simplex type 2 | genital lesions |
| HIV | acquired immunodeficiency syndrome |
| HTLV-1 | T cell leukemia |
| influenza virus | upper respiratory tract infection, pneumonia |
| measles virus | measles |
| papillomavirus | warts, associated with later-developing cervical cancer |
| pneumovirus | respiratory infection |
| polyomavirus | malignant tumors in animals |
| reoviridae | diarrhea, Colorado tick fever |
| rhabdoviruses | rabies |
| rhinovirus | common cold |
| ribvirus | rubella |
| varicella-zoster | chickenpox, herpes zoster (shingles) |

In particular, microbial products which stimulate the same $V_H$ family restricted antibodies which are preferentially stimulated by the sAg are expected to be efficaciously treated with a vaccine or composition utilizing the sAg as a carrier or adjuvant. With respect to SpA, microorganisms with components which stimulate $V_H3$ restricted antibodies are now known to include the encapsulated bacteria *Haemophilus influenzae* Type b (Hib) (see, Silverman and Lucas (1991) *J. Clin. Invest*. 88:911–920 [the disclosure of which regarding the experimental protocols used to identify Hib as stimulating $V_H3$ restricted antibodies is incorporated herein]) and *Streptococcus pneumoniae.*

With respect to the latter, pneumococcal polysaccharides also stimulate production of $V_H3$ restricted antibodies as shown in the experiment described below.

As shown by the data in FIGS. 5–7, 20 healthy human adults were immunized with the polyvalent PNEUMOVAX vaccine (Merck Sharpe and Dohme) and pre- and post-immunization levels to antibodies to each of the 24 different purified polysaccharides in the vaccine were measured. Responders were then selected, who had over three fold increase in post-immunization IgG antibody responses, and antibodies to a particular capsular type were purified by direct precipitation, following exactly the method described in Silverman and Lucas (*J. Clin Invest* (1991) 88:911–920).

Following this protocol, the purified antibody antigen complexes were separated by PAGE electrophoresis under reducing conditions, and the variable region composition of the antibodies was assessed by subjecting replicate immunoblots to analysis with a series of serologic reagents that are each specific for particular human immunoglobulin variable region families. Thereby, it was established that several antibody responses examined in detail, C-polysaccharide, Type 14, and Type 19, exclusivety used or were highly biased toward the usage of the $V_H3$ family, while many $V_L$ families were used within a particular response in an individual.

Referring to Tables VIII–X, a particular subject is listed at left, then the strength of reactivity of his polysaccharide specific antibodies with each of the serologic reagents is listed beneath the name of the reagent. $V_H1$, $V_H4$ and $V_H3$ represent reagents that identify most or all members of their respective families. Subsets within the $V_H3$ family are identified by the $V_H3$-$V_H2$a and $V_H3$-FR3a antibodies that identify different component on one type of $V_H3$ H chain, and $V_H3$-HV2b which identifies another distinct, separate small subset of $V_H3$ H chains. These reagents and their specificity are described in the *J. Clin Invest* paper, but the significant finding is that similar H chains are used in anti-Hib PS (polysaccharide) and anti-pneumococcal responses. Antibodies that contain H chains from these $V_H3$ subsets are shown to react with the alternative binding of SpA. In contrast, there is little or no restriction of $V_L$ usage by anti-pneumococcal antibodies.

It is expected based on success with conventional vaccines that the inventive vaccine will also be particularly useful in enhancing immune response to *Neiserria meningitidis.*

Once an optimal size for the pathogen component as well as the best molar ratio of component to sAg, has been determined according to the above-described methods, construction of a conjugate vaccine will generally be performed according to method reported for preparation of conventional polysaccharide vaccines by Peters, et al. (1991) 30:267–274 (discussion at anti-Hib, anti-meningitidis and anti-pneumococcal conjugate vaccines). Other references of interest in this regard are Tsai, et al. (1989) *J. Biol. Stand.* 17:249–258; Verhuel, et al. (1989) *Infection and Immunity* 57:1078–1083, and Allison, et al. (1991) *Molec. Immun.* 28:279–284 (all of these references are incorporated herein).

In particular with respect to SpA, the preferred form of SpA is expected to be a highly purified recombinant form available commercially from Calbiochem, which is sold under the trade name ULTRAPURE (rSpA). It is expected that the most efficacious form of SpA for use in the vaccine will be one which has been hyperiodinated to eliminate Fc binding activity (i.e., mod-SpA). Hyperiodnation is performed as follows: 1 mg of SpA is dissolved in 350 ul of 5× borate buffered saline (BBS; ph 8.2). Under a fume hood, on ice, 600 ul of 0.02M iodine monochloride is added dropwise with agitation. This solution is incubated for 30 minutes at 4° C., then the mixture is dialyzed against 1× BBS or PBS, with three changes of buffer over 48 hours at 4° C.

Other forms of SpA which may be used are the purified native form or purified, modified (hyperiodinated) form. The recombinant form is preferred because it is expressed in a *E.coli* strain which contains the Protein A gene from a *S. aureus* Cowan I strain (SAC). As a result, rSpA (in particular the ULTRAPURE SpA product) is free of staphylococcal enterotoxins and hemolysins. rSpA has also been shown to achieve a higher purity level than the purified, native *S. aureus* produced Protein A. rSpA from *E. coli* also has higher solubility and expression of protein levels than *S. aureus* derived Protein A; their binding activity is comparable to IgG.

Further, it should be noted with respect to SpA that it contains four IgG $F_c$ binding activity (regions D,A, B and C). ft is known that SpA has at least two Fab binding sites, but they have not as yet been localized. However, due to the need to cross-link Fab for superantigen B cell stimulation, at least two Fab binding sites on the vaccine sAg are expected to be required and may be present in each region, thus allowing for use of a D, A, B or C fragment in the vaccine rather than whole SpA.

Several variables come into play in preparing the conjugate vaccine (which to some extent are considerations for the unconjugated vaccine as well), including polysaccharide/sAg protein or glycoprotein/sAg protein ratio, solubility use of spacers, monosaccharide composition and, in certain uses the degree cross-linking in presence of an additional adjuvant. Generally, preparation of test vaccines which vary as against a control in these factors (including the use of oligo-saccharides in lieu of polysaccharides) and immunization of different test and control groups win, without undue experimentation, yield sufficient information to determine an optimal structure for the vaccine.

Suitable experimental protocols are reported in Verhuel, et al. supra, and Peters, et al. suora (regarding polysaccharide/protein ratios, see, in particular, Verhuel et al. at Table I therein for reference). It is expected that the sAg/component vaccines produced and used according to this invention which incorporate poly- or oligosaccharide components will use the soluble carbodiimide conjugation method, preceded by periodate oxidation (and, for modSpA, hyperiodination) of the polysaccharide prior to linkage with a 6-aminohexanoic acid spacer by cyanogen bromide (see Peters, supra; and, Chu, et al. (1983) Infect. Immunol. 40:245–256 [incorporated herein by this reference]). Alternatively, the polysaccharide can be activated with cyanogen bromide then reacted with adipic dihydrazide to make a polysaccharide hydrazide derivative prior to carbodiimide conjugation. Other spacers have also been described by Marburg, et al. (1986) J. Am. Chem. Soc. 108:5282–5287.

Generally, it can be expected that oligosaccharides will be more immunogenic than polysaccharides (although Peters, et al. reported that the opposite was true in a type 4 S.pnuemoniae conjugate vaccine). Further, the use of spacer molecules is expected to be preferred. However, based on the expected enhancement of the immune response by the sAg, use of an additional adjuvant (such as the polysacoharide to titerpenoid quillaic acid conjugate) should not be necessary or desirable.

It is not entirely clear based on work to date that conjugation of the sAg and component will be required to stimulate the desired immune response. These may, therefore, be tested and administered in an unconjugated composition of purified sAg/component supematants. In this respect, it is expected that it may be desirable to maintain the percentage of unconjugated component in the composition to less than 10% to avoid inducing immunosuppression. Alternatively, the immune response may be enhanced by administration of equally low dosages of unconjugated component prior to administration of the conjugated vaccine.

Administration may be subcutaneous, intramuscular, subdermal, intravenous, intraperitoneal or intradermal; the former is preferred. Resulting circulating antibody levels will be verified by immunoassay means well-known in the art; i.e., modified radioimmunoassay or competition ELISA (see e.g., method reported for use with conventional pneumococcal vaccines in Peters, et al. 1991, J. Immunol. 146:4308–4314; see also, the ELISA protocols described in Example II and III below).

For construction of conjugates having a glycoprotein component, different chemical conjugation means are used in methods similar to those described above. Carboniimide, glutaraldehyde, bis-diazotized benzidine or m-maleimidobenzoyl-N-hydroxysuccinimide ester may be used as cross-linkers to perform the conjugation. Specific suitable coupling methods for conjugation of peptides (including glycoproteins) to carrier proteins are described in Harlow et al. "Antibodies: a laboratory manual", Cold Spring Harbor Laboratory (1988), Ch. 5, 78–87.

It should be noted that not all of the above methods have been approved for use in vaccines intended for administration to humans. As a result, while all are suitable for use in testing as described above, the final production conjugation method may have to be modified to adapt to then-currently approved methods for use in humans.

The invention having been fully described, examples illustrating its practice are provided below. However, it will be understood that the invention, defined by the appended claims, is not limited by the examples and that modifications may be made to the invention as described therein and in the specification without departing from its spirit or scope.

EXAMPLE I

IDENTIFICATION OF THE $V_H3$ RESTRICTED IG (Fab) BINDING SITE ON SpA

To determine whether the D domain of SpA will bind Ig Fab (of, in particular, $V_H3$ restricted Ig), the D domain has been cloned and expressed in vitro. This was performed by use of the polymerase chain reaction, using two oligonucleotide primers that flank the D domain.

1. Primer Construction.

The upstream primer, DomD 5' (SEQ.ID.No. 49), includes the DNA sequence of a three codon insertion unique to SpA domain D (and E) so that the D domain would be selectively amplified. The other primer, DomDAS 3' (SEQ.ID.No. 50), includes an antisense sequence that is about 232 nucleotides away from the first primer. Together, in the conditions indicated below, these primers amplified an about 232 base pair fragment of DNA.

These primers also include some differences from the natural SpA sequence which create new potential DNA restriction sites. This band of DNA was then purified, and the DNA was digested at specific sites with the restriction enzymes BamHI and BgIII, that had been engineered into the oligonucieotide primers. The DNA fragment was then purified again by agarose gel electrophoresis, and it was ligated into a property prepared cloning site into a modified pUC19 plasmid, which allowed directional cloning of the fragment into a position in which it was grafted at the 3' end of a ompA leader sequence. This gene is also under the control of an upstream Lac operon. The plasmid includes the ampicillin resistance gene that enables selection of plasmid containing bacteria by antibiotic selection. Therefore, after introduction into a compatible E. Coli strain, and selection with ampicillin or carbenicillin, expression of the D domain can be induced by the standard IPTG method.

For the PCR amplification, the plasmid, pSpA8, which contains the SpA genome was obtained from the American Type Culture Collection in Rockville, Md. and used as a template. The following reaction conditions were employed:

94° C. for 1 minute, 80° C. for 1 minute (and the Taq polymerase is added), then 30 cycles of:
93° C. for 1 min
46° C. for 2 min
72° C. for 2 min, then
72° C. for 10 minutes.

These reactions were performed in an "ERICOMP" thermocycler (San Diego, Calif.) in a 100 ul final volume, containing each primer in a final concentration of 0.01 pM/ul, MgCl2 at 1.0 mM, 20Q microM of each of the dNTP, 1 ng of the template DNA and a total of 5 units of Taq polymerase. As controls, identical tubes that lacked one of the primers, and a tube that lacked only the template DNA were treated under identical conditions. These control tubes failed to produce DNA of the predicted size, as predicted.

To analyze Ig binding capacity the bacterial extracts that include the Domain D product were subjected to size separation of the component proteins under reducing conditions (1% 2-mercaptoethanol) on 15% polyacrylamide gel electrophoresis. For comparison, extracts of bacteria that did not contain the plasmid were prepared in the same manner (negative control), SpA from a commercial source (positive control), and MW markers were run on adjacent lanes to the Domain D containing extract They were then electrotransferred onto a "IMMOBILON" pR membrane (Millipore, Bedford, Mass.). The membranes were then subjected to immunoblotting with different Ig preparations. These studies demonstrated that Domain D binds to a component of purified polydonal IgM from adult donors, and also that it binds to monoclonal VH3 IgM.

The predicted protein sequence for the portion of the D domain of SpA that binds Fab is the following 61 amino acids (SEQ.ID.No. 51):
ADAQQNNFNKDQQSAFYEILNMPL-NEAQRNGEFIOSTKDDPSOSTNV-LGEAKKLNESQAPK

EXAMPLE II

RESPONSE TO SpA IMMUNIZATION IN A MURINE MODEL AND UTILITY OF THE MODEL FOR PREDICTION OF THE RESPONSE TO SpA IN HUMANS

A. In vivo Production of Murine Ig Against Mod-SpA

A sample of recombinant SpA free of *E.coli* endotoxins was purchased from a commercial source (Repligen, Cambridge, Mass.) and the SpA was modified by hyperiodination to remove Fc binding as described elsewhere above. Balb/c mice (in groups of three), were immunized subcutaneously on their backs with 100 mcg of the mod-SpA in an alum emulsion in 0.5 ml of normal saline at day 0, and 50 mcg.ml at week 8. A control group received sham (i.e., saline only) injections. Blood samples were taken periodically and enzyme-linked immunoabsorbent assays (ELISA's) performed on the samples as follows.

Experimentally naive adult female Balb/c mice were immunized with 100 mcg of endotoxin-free mod-SpA at day 0, and with 50 mcg/ml at week 8. Blood samples were obtained periodically, and immune assay performed as follows. Duplicate microtiter wells were precoated with mod-SpA at 5 mcg/ml in phosphate buffered saline, pH 7.4 (PBS) overnight at 4° C. Plates were then blocked with 1% bovine serum albumin (BSA) in PBS for 1 hr at RT. In duplicate, samples diluted 1:5000 in BSA-PBS were incubated on plates for 2 hr at 37° C. Plates were then washed and then incubated with either affinity purified goat anti-mouse IgG-horse radish peroxidase, or affinity purified goat anti-mouse IgM-horse radish peroxidase, for 1 hour at room temperature. Plates were then washed, then developed with substrate and optical density was read at 405 A with optical density of 490 A subtracted. The background reading of wells without mouse serum samples was 0.050.

Fc binding activity was undetectable in an ELISA that was sensitive enough to detect less than 3% of the original activity, but Ig Fab binding capacity was preserved. Also, as determined by flow cytometry the total number of B cells in these mice at least doubled, but the proportion of B lymphocytes that bound the mod-SpA did not change.

However, assays of Ig binding of mod-SpA indicated that the animals developed an immune response to immunization, which was boosted after secondary immunization with mod-SpA These mice were shown to have an increase in the titers of mod-SpA binding Ig within 24 weeks after primary immunization (FIG. 5). Ig binding levels increased 1.5 to about 4 fold with peaks between 4 and 7 weeks and then declined. Secondary immunization with 50 mcg of mod-SpA administered by the same route induced more rapid and greater increases with greater increases in the IgG than the IgM binding of mod-SpA. Overall, most of the response was IgG. with lesser increases in IgM mod-SpA binding.

Because the mice immunized with mod-SpA continue to have increased levels of Ig that bind mod-SpA for 14 weeks after secondary immunization, it can be concluded that, unlike the effect of exposure of certain T cell superantigens to T lymphocytes, immunization with mod-SpA does not result in subsequent B cell unresponsiveness to secondary exposure to mod-SpA B. Inhibition of SpA Binding of Anti-SpA Murine Ig by a Human Monoclonal Antibody.

Inhibition studies documented that immunization caused an increase in the binding of murine Ig against a SpA site that is also bound by monoclonal human $V_H3$ IgM (FIG. 6).

The experiment was performed as indicated above, except that after blocking of each plate, one half of each plate was preincubated with affinity purified SpA3-08 Fab at 5 mcg/ml in BSA-PBS while the other part of each plate had only 1% BSA-PBS, for 2 hr at 37° C. Serial dilution of a post-immunization mouse sera, in triplicate, were then added to both sides of the plate and incubated for 2 hr at 37° C. Plates were then washed and developed as above, except using affinity purified goat anti-mouse IgG and IgM-horse radish peroxidase. Preincubation of the mod-SpA with the SpA3-08 Fab, caused about a ⅔ reduction of the murine Ig binding to mod-SpA in the post-immunization sample.

In one mouse examined, an inhibition study established that ⅔ of the mod-SpA binding in the secondary response to mod-SpA could be blocked by preincubation of the mod-SpA with a human monoclonal IgG Fab, termed SpA3-08. This confirms that SpA immunization of adult Balb/c mice causes an increase of circulating $V_H3$ restricted Ig that bind mod-SpA, which response is predominately directed at (or near) the human VH3 Fab binding site on SpA.

EXAMPLE III

CO-IMMUNIZATION OF PNEUMOCOCCAL POLYSACCHARIDE AND mod-SpA INFLUENCES THE RESPONSE TO PNEUMOCOCCAL POLYSACCHARIDE Groups of four experimentally naive adult female mice were subcutaneously immunized with 0.5 ml of normal saline emulsified in alum which contained either a 1:50 dilution of "PNEUMOVAX" pneumococcal vaccine (Merck Sharpe and Dohme, West Point, Pa.) or 1:50 dilution of "PNEUMOVAX" with 50 mcg of mod-SpA (endotoxin-free). Pre-immunization responses were then compared with 6 weeks postimmunizaton samples.

To this end, ELISA's were performed as described in Example II except that precoats utilized purified polysaccharide 14 (Merck, Shaerpe and Dohme) at 20 mcg/ml in phosphate buffered saline (PBS) overnight at 4° C. Sera were diluted 1:100 in BSA-PBS and preincubated for 2 hours at 37° C. with pneumococcal cell wall, then incubated on the plates for 2 hours at 37° C. Plates were then washed, then incubated with mod-SpA-biotin for 1 hour at room temperature, then washed and developed with avidin-horseradish peroxidase.

All animals had increased titers to type specific capsular pneumococcal polysaccharide 14. The levels were not significantly different in immunoassays of sera using a precoat of polysaccharide 14 and a detecting agent of affinity purified goat anti-mouse IgG and IgM horseradish peroxidase (data not shown). However, when the studies were repeated substituting labelled mod-SpA as the detecting agent, the level of mouse Ig reactive with both mod-SpA and polysaccharide 14 was different between the groups (FIG. 7). A higher level of dually reactive mouse Ig was present in each mouse that received both mod-SpA and "PNEUMOVAX" compared to every mouse that received "PNEUMOVAX" alone. These data indicate that co-administration of mod-SpA and a polysaccharide, even without chemical conjugation, can influence the resultant response to the polysaccharide.

SUMMARY OF SEQUENCES

SEQUENCE ID NO's: 1–11 are the amino acid sequences for intact IgM and IgG antibodies with significant mod-SpA binding activity which are shown in Table II.A.

SEQUENCE ID NO's: 12–18 are amino acid sequences for monoclonal antibodies (non-VH3 origin) which are devoid of SpA binding activity and which are shown in Table II.A.

SEQUENCE ID NO's: 20, 22, 24, 26, 28, 30, 32, 34, 36, 38 and 40 are amino acid sequences for monoclonal Fab which were isolated from a combinatorial library based on SpA binding capacity and which are shown in Table II.A.

SEQUENCE ID NO's: 19, 21, 23, 25, 27, 29, 31, 33, 35, 37, 39, 41, 42, 43, 44, 45, 46, 47 and 48 are nucleotide sequences and corresponding amino acid sequences for the variable heavy in regions of SpA binders from combinatorial libraries which are depicted in Table II.B. SEQUENCE ID NO: 42, 44, 46 and 48 correspond to the nucleotides shown in SEQUENCE ID NO: 41, 43, 45 and 47.

SEQUENCE ID NO's: 49–50 are amino acid sequences of primers used to amplify Domain D of SpA.

SEQUENCE ID NO: 51 is the amino acid sequence of Domain D of SpA.

I claim:

1. A composition comprising a peptide and a microbial polysaccharide antigen or glycoprotein antigen wherein the peptide is a B cell superantigen with Fab antibody binding specificity and the amino acid sequence of SEQ. ID. No. 51.

2. A composition according to claim 1 wherein the microbial polysaccharide antigen stimulates production in vertebrates of antibodies restricted to the $V_H3$ family.

3. A method for stimulating the production of variable (V) region family restricted antibodies against one or more microbial polysaccharide antigens or glycoprotein antigens in a vertebrate host, the method comprising:

administering a peptide wherein the peptide is a B cell superantigen with Fab antibody binding specificity and the amino acid sequence of SEQ. ID. No. 51 concomitantly with at least one of said microbial polysaccharide antigens or glycoprotein antigens to the host, wherein said administering stimulates B cell proliferation and production by the host of variable region restricted antibodies with binding specificity for the microbial polysaccharide antigens or glycoprotein antigens.

* * * * *

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 18/2

( i x ) FEATURE:
        ( A ) NAME/KEY: Peptide
        ( B ) LOCATION: 1..125

( x i ) SEQUENCE DESCRIPTION: SEQ ID NO:1:

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Lys Gly Gln Val Leu Tyr Tyr Gly Ser Gly Ser Tyr His Trp Phe
                100                 105                 110
Asp Pro Trp Gly Gln Gly Thr Leu Val Thr Val Ser Ser
            115                 120                 125
```

( 2 ) INFORMATION FOR SEQ ID NO:2:

( i ) SEQUENCE CHARACTERISTICS:
( A ) LENGTH: 116 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( B ) CLONE: ED8.4

( i x ) FEATURE:
( A ) NAME/KEY: Peptide
( B ) LOCATION: 1..116

( x i ) SEQUENCE DESCRIPTION: SEQ ID NO:2:

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Leu Gln Pro Pro Gly Lys Gly Leu Glu Trp Val
        35                  40                  45

Ser Ala Ile Ser Gly Ser Gly Gly Arg Thr Tyr Tyr Ala Asp Ser Val
        50                  55                  60

Lys Gly Arg Phe Thr Ile Ser Arg Glu Asn Ser Lys Asn Thr Leu Tyr
65                      70                  75                  80

Val Gln Met Asn Ser Leu Arg Val Glu Asp Thr Ala Val Tyr Tyr Cys
                85                  90                  95

Ala Lys Gly Tyr Gly Met Asp Val Trp Gly Gln Gly Thr Leu Val
                100             105                 110

Thr Val Ser Ser
        115
```

( 2 ) INFORMATION FOR SEQ ID NO:3:

( i ) SEQUENCE CHARACTERISTICS:
( A ) LENGTH: 109 amino acids
( B ) TYPE: amino acid
( C ) STRANDEDNESS: single
( D ) TOPOLOGY: linear ( i i ) MOLECULE TYPE:

( v i i ) IMMEDIATE SOURCE:
( B ) CLONE: Huab14-3

( i x ) FEATURE:
( A ) NAME/KEY: Peptide
( B ) LOCATION: 1..109

( x i ) SEQUENCE DESCRIPTION: SEQ ID NO:3:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Arg Met His Trp Val Arg Gln Ala Pro Gly Lys Gly Leu Val Trp Val
        35                  40                  45

Ser Arg Ile Asn Ser Asp Gly Ser Ser Thr Asp Tyr Ala Asp Ser Val
        50                  55                  60

Glu Gly Arg Phe Thr Ile Ser Arg Asp Asn Ala Lys Asn Thr Leu Tyr
65                      70                  75                  80

Leu Gln Met Asn Ser Leu Arg Ala Glu Asp Thr Ala Val Tyr Tyr Phe
                85                  90                  95
```

Asp Ser Trp Gly Gln Gly Thr Leu Val Thr Val Ser Ser
               100                     105

(2) INFORMATION FOR SEQ ID NO:4:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: SFL (ix) FEATURE:
        (A) NAME/KEY: Peptide
        (B) LOCATION: 1..108

(xi) SEQUENCE DESCRIPTION: SEQ ID NO:4:

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Thr Xaa Tyr
               20                  25                  30

Xaa Met Ser Trp Val Arg Gln Ala Pro Gly Lys Gly Leu Glu Trp Val
           35                  40                  45

Ala Phe Ile Tyr Arg Ser Gly Ile Asn Lys Tyr Tyr Ala Asp Ser Val
       50                  55                  60

Asn Gly Arg Phe Thr Ile Ser Arg Asp Asn Xaa Lys Asn Thr Leu Xaa
 65                  70                  75                  80

Xaa Xaa Met Asn Ser Leu Arg Ala Glu Asp Thr Ala Leu Tyr Tyr Cys
               85                  90                  95

Ala Lys Asp Ala Gly Leu Lys Val Glu Lys Ser Val
               100                 105

(2) INFORMATION FOR SEQ ID NO:5:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: KIM (ix) FEATURE:
        (A) NAME/KEY: Peptide
        (B) LOCATION: 1..125

(xi) SEQUENCE DESCRIPTION: SEQ ID NO:5:

Glu Val Gln Leu Val Glu Ser Gly Gly Gly Val Val Gln Pro Gly Ser
 1               5                  10                  15

Ser Leu Arg Leu Ser Cys Ala Ala Ser Gly Phe Thr Phe Ser Ser Phe
               20                  25                  30

Ala Met His Trp Val Arg Gln Ala Pro Gly Lys Gly Leu Glu Trp Val
           35                  40                  45

Ala Val Met Ser Tyr Ser Gly Asp Asn Lys Tyr Tyr Val Asp Ser Val
       50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys 85                            90                              95

Ala  Lys  Leu  Ser  Thr  Ala  Ala  Ser  Gly  Phe  Thr  Phe  Asp  Thr  Tyr  Gly
               100                           105                         110

Met  Asp  Trp  Gly  Gln  Thr  Thr  Leu  Val  Thr  Val  Ser  Ser
               115                      120                    125

( 2 ) INFORMATION FOR SEQ ID NO:6:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: RIV ( i x ) FEATURE:
        ( A ) NAME/KEY: Peptide
        ( B ) LOCATION: 1..125

( x i ) SEQUENCE DESCRIPTION: SEQ ID NO:6:

Glu  Val  Gln  Leu  Val  Glu  Ser  Gly  Gly  Val  Val  Gln  Pro  Gly  Ser
1                    5                    10                         15

Ser  Leu  Arg  Leu  Ser  Cys  Ala  Ala  Ser  Gly  Phe  Thr  Phe  Ser  Ser  Phe
               20                       25                       30

Ala  Met  His  Trp  Val  Arg  Gln  Ala  Pro  Gly  Lys  Gly  Leu  Glu  Trp  Val
               35                       40                       45

Ala  Val  Met  Ser  Tyr  Ser  Gly  Asp  Asn  Lys  Tyr  Tyr  Val  Asp  Ser  Val
          50                       55                       60

Lys  Gly  Arg  Phe  Thr  Ile  Ser  Arg  Asp  Asn  Ser  Lys  Asn  Thr  Leu  Tyr
65                       70                       75                       80

Leu  Gln  Met  Asn  Ser  Leu  Arg  Ala  Glu  Asp  Thr  Ala  Leu  Tyr  Tyr  Cys
                    85                       90                       95

Ala  Lys  Leu  Ser  Thr  Ala  Ala  Ser  Gly  Phe  Thr  Phe  Asp  Thr  Tyr  Gly
               100                           105                         110

Met  Asp  Trp  Gly  Gln  Thr  Thr  Leu  Val  Thr  Val  Ser  Ser
               115                      120                    125

( 2 ) INFORMATION FOR SEQ ID NO:7:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: LAY ( i x ) FEATURE:
        ( A ) NAME/KEY: Peptide
        ( B ) LOCATION: 1..120

( x i ) SEQUENCE DESCRIPTION: SEQ ID NO:7:

Ala  Val  Gln  Leu  Leu  Glu  Ser  Gly  Gly  Gly  Leu  Val  Gln  Pro  Gly  Gly
1                    5                    10                         15

Ser  Leu  Arg  Leu  Ser  Cys  Ala  Ala  Ser  Gly  Phe  Thr  Phe  Ser  Ala  Ser
               20                       25                       30

Ala  Met  Ser  Trp  Val  Arg  Gln  Ala  Pro  Gly  Lys  Gly  Leu  Glu  Trp  Val
               35                       40                       45

| Ala | Trp | Lys | Tyr | Glu | Asn | Gly | Asn | Asp | Lys | His | Tyr | Ala | Asp | Ser | Val |
|     | 50  |     |     |     |     | 55  |     |     |     |     | 60  |     |     |     |     |

| Asn | Gly | Arg | Phe | Thr | Ile | Ser | Arg | Asn | Asp | Ser | Lys | Asn | Thr | Leu | Tyr |
| 65  |     |     |     |     | 70  |     |     |     |     | 75  |     |     |     |     | 80  |

| Leu | Gln | Met | Asn | Gly | Leu | Gln | Ala | Glu | Val | Ser | Ala | Ile | Tyr | Tyr | Cys |
|     |     |     |     | 85  |     |     |     |     | 90  |     |     |     |     | 95  |     |

| Ala | Arg | Asp | Ala | Gly | Pro | Tyr | Val | Ser | Pro | Thr | Phe | Phe | Ala | His | Trp |
|     |     |     | 100 |     |     |     |     | 105 |     |     |     |     | 110 |     |     |

| Gly | Gln | Gly | Thr | Leu | Val | Thr | Val |
|     |     | 115 |     |     |     |     | 120 |

( 2 ) INFORMATION FOR SEQ ID NO:8:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: POM ( i x ) FEATURE:
        ( A ) NAME/KEY: Peptide
        ( B ) LOCATION: 1..122

( x i ) SEQUENCE DESCRIPTION: SEQ ID NO:8:

| Glu | Val | Gln | Leu | Leu | Glu | Ser | Gly | Gly | Leu | Val | Gln | Pro | Gly | Gly |
| 1   |     |     |     | 5   |     |     |     |     | 10  |     |     |     |     | 15  |

| Ser | Leu | Arg | Leu | Ser | Cys | Ala | Ala | Ser | Gly | Phe | Thr | Phe | Ser | Ser |
|     |     |     | 20  |     |     |     |     | 25  |     |     |     |     | 30  |     |

| Ala | Met | Ser | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |

| Ala | Trp | Lys | Tyr | Glu | Asn | Gly | Asn | Asp | Lys | His | Tyr | Ala | Asp | Ser | Val |
|     | 50  |     |     |     |     | 55  |     |     |     |     | 60  |     |     |     |     |

| Asn | Gly | Arg | Phe | Thr | Ile | Ser | Arg | Asn | Asp | Ser | Lys | Asn | Thr | Leu | Tyr |
| 65  |     |     |     |     | 70  |     |     |     |     | 75  |     |     |     |     | 80  |

| Leu | Leu | Met | Asn | Ser | Leu | Gln | Ala | Glu | Asp | Thr | Ala | Leu | Tyr | Tyr | Cys |
|     |     |     |     | 85  |     |     |     |     | 90  |     |     |     |     | 95  |     |

| Ala | Arg | Asp | Ala | Gly | Pro | Tyr | Val | Ser | Pro | Thr | Phe | Phe | Ala | His | Tyr |
|     |     |     | 100 |     |     |     |     | 105 |     |     |     |     | 110 |     |     |

| Gly | Gln | Gly | Thr | Leu | Val | Thr | Val | Ser | Ser |
|     |     | 115 |     |     |     |     | 120 |     |     |

( 2 ) INFORMATION FOR SEQ ID NO:9:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: Huab2-3

( i x ) FEATURE:
        ( A ) NAME/KEY: Peptide
        ( B ) LOCATION: 1..125

( x i ) SEQUENCE DESCRIPTION: SEQ ID NO:9:

| Glu<br>1 | Val | Gln | Leu | Val<br>5 | Glu | Ser | Gly | Gly | Gly<br>10 | Leu | Val | Gln | Pro | Gly<br>15 | Gly |
|---|---|---|---|---|---|---|---|---|---|---|---|---|---|---|---|
| Ser | Leu | Lys | Leu<br>20 | Ser | Cys | Ala | Ala | Ser<br>25 | Gly | Phe | Thr | Phe | Ser<br>30 | Ala | Ser |
| Ala | Val | His<br>35 | Trp | Val | Arg | Gln | Ala<br>40 | Pro | Gly | Lys | Gly | Leu<br>45 | Glu | Trp | Val |
| Gly | Arg<br>50 | Ile | Arg | Ser | Lys | Ala<br>55 | Asn | Ser | Tyr | Ala | Thr<br>60 | Ala | Tyr | Ala | Ala |
| Ser<br>65 | Val | Lys | Gly | Arg | Phe<br>70 | Thr | Ile | Ser | Arg | Asp<br>75 | Asn | Ser | Lys | Asn | Thr<br>80 |
| Ala | Tyr | Leu | Gln | Met<br>85 | Asn | Ser | Leu | Lys | Thr<br>90 | Glu | Asp | Thr | Ala | Val<br>95 | Tyr |
| Tyr | Cys | Thr | Gly<br>100 | His | Pro | Leu | Tyr | Tyr<br>105 | Val | Thr | Thr | Pro | His<br>110 | Trp | Phe |
| Asp | Pro | Trp<br>115 | Gly | Gln | Gly | Thr | Leu<br>120 | Val | Thr | Val | Ser | Ser<br>125 | | | |

( 2 ) INFORMATION FOR SEQ ID NO:10:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: SB5/D6

( i x ) FEATURE:
        ( A ) NAME/KEY: Peptide
        ( B ) LOCATION: 1..116

( x i ) SEQUENCE DESCRIPTION: SEQ ID NO:10:

| Glu<br>1 | Val | Gln | Leu | Val<br>5 | Glu | Ser | Gly | Gly | Gly<br>10 | Leu | Val | Lys | Pro | Gly<br>15 | Gly |
|---|---|---|---|---|---|---|---|---|---|---|---|---|---|---|---|
| Ser | Leu | Arg | Leu<br>20 | Ser | Cys | Ala | Ala | Ser<br>25 | Gly | Phe | Thr | Phe | Ser<br>30 | Asn | Ala |
| Trp | Met | Asn<br>35 | Trp | Val | Arg | Gln | Ala<br>40 | Pro | Gly | Lys | Gly | Leu<br>45 | Glu | Trp | Val |
| Gly | Arg<br>50 | Ile | Lys | Thr | Lys | Thr<br>55 | Asp | Gly | Gly | Thr | Thr<br>60 | Asp | Tyr | Ala | Ala |
| Pro<br>65 | Val | Lys | Gly | Arg | Phe<br>70 | Thr | Ile | Ser | Arg | Asn<br>75 | Asp | Ser | Lys | Asn | Thr<br>80 |
| Leu | Tyr | Leu | Gln | Met<br>85 | Asn | Ser | Leu | Lys | Thr<br>90 | Glu | Asp | Thr | Ala | Val<br>95 | Tyr |
| Tyr | Cys | Thr | Thr<br>100 | Gly | Gly | Gly | Val | Gly<br>105 | Trp | Gly | Gln | Gly | Thr<br>110 | Leu | Val |
| Thr | Val | Ser | Ser<br>115 | | | | | | | | | | | | |

( 2 ) INFORMATION FOR SEQ ID NO:11:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:

( B ) CLONE: 4B4

( i x ) FEATURE:
    ( A ) NAME/KEY: Peptide
    ( B ) LOCATION: 1..119

( x i ) SEQUENCE DESCRIPTION: SEQ ID NO:11:

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asn | Ala |
| | | | 20 | | | | | 25 | | | | | 30 | | |
| Trp | Met | Ser | Trp | Val | Arg | Gln | Ala | Pro | Gly | Lys | Gly | Leu | Glu | Trp | Val |
| | | 35 | | | | | 40 | | | | | 45 | | | |
| Gly | Arg | Ile | Lys | Ser | Lys | Thr | Asp | Gly | Gly | Thr | Thr | Asp | Tyr | Ala | Ala |
| | 50 | | | | | 55 | | | | | 60 | | | | |
| Pro | Val | Lys | Gly | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Lys | Thr | Glu | Asp | Thr | Ala | Val | Tyr |
| | | | | 85 | | | | | 90 | | | | | 95 | |
| Tyr | Cys | Thr | Thr | Asp | Ser | Leu | Pro | Pro | His | Arg | Val | Trp | Gly | Gln | Gly |
| | | | 100 | | | | | 105 | | | | | 110 | | |
| Thr | Leu | Val | Thr | Val | Ser | Ser | | | | | | | | | |
| | | 115 | | | | | | | | | | | | | |

( 2 ) INFORMATION FOR SEQ ID NO:12:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: BOR ( i x ) FEATURE:
        ( A ) NAME/KEY: Peptide
        ( B ) LOCATION: 1..120

( x i ) SEQUENCE DESCRIPTION: SEQ ID NO:12:

| Val | Gln | Leu | Val | Gln | Ser | Gly | Ala | Glu | Val | Lys | Lys | Pro | Gly | Ser | Ser |
|---|---|---|---|---|---|---|---|---|---|---|---|---|---|---|---|
| 1 | | | | 5 | | | | | 10 | | | | | 15 | |
| Val | Lys | Val | Thr | Cys | Lys | Ala | Ser | Gly | Asp | Thr | Phe | Ser | Ser | Ser | Ala |
| | | | 20 | | | | | 25 | | | | | 30 | | |
| Ile | Ser | Trp | Val | Arg | Gln | Ala | Pro | Gly | Gln | Gly | Leu | Glu | Trp | Met | Gly |
| | | 35 | | | | | 40 | | | | | 45 | | | |
| Gly | Ile | Ile | Pro | Ile | Phe | Gly | Thr | Pro | Asn | Tyr | Ala | Gln | Lys | Phe | Gln |
| | 50 | | | | | 55 | | | | | 60 | | | | |
| Gly | Arg | Val | Thr | Ile | Thr | Thr | Asp | Glu | Ser | Thr | Ser | Thr | Ala | Tyr | Met |
| 65 | | | | | 70 | | | | | 75 | | | | | 80 |
| Glu | Val | Ser | Ser | Leu | Arg | Ser | Glu | Asp | Thr | Ala | Leu | Tyr | Tyr | Cys | Ala |
| | | | | 85 | | | | | 90 | | | | | 95 | |
| Arg | Glu | Gly | Arg | Arg | Met | Ala | Ile | Asn | Pro | Phe | Asp | Tyr | Trp | Gly | Gln |
| | | | 100 | | | | | 105 | | | | | 110 | | |
| Gly | Thr | Leu | Val | Thr | Val | Ser | Ser | | | | | | | | |
| | | | 115 | | | | 120 | | | | | | | | |

( 2 ) INFORMATION FOR SEQ ID NO:13:

( i ) SEQUENCE CHARACTERISTICS:

(A) LENGTH: 120 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: KAS (ix) FEATURE:
(A) NAME/KEY: Peptide
(B) LOCATION: 1..120

(xi) SEQUENCE DESCRIPTION: SEQ ID NO:13:

| Val | His | Leu | Val | Gln | Ser | Gly | Ala | Glu | Val | Lys | Lys | Pro | Gly | Ser | Ser |
|---|---|---|---|---|---|---|---|---|---|---|---|---|---|---|---|
| 1 | | | | 5 | | | | | 10 | | | | | 15 | |

| Val | Lys | Val | Ser | Cys | Lys | Ala | Ser | Gly | Gly | Thr | Phe | Ser | Ser | Tyr | Ala |
|---|---|---|---|---|---|---|---|---|---|---|---|---|---|---|---|
| | | | 20 | | | | | 25 | | | | | 30 | | |

| Ile | Ser | Trp | Val | Arg | Gln | Ala | Pro | Gly | Gln | Gly | Leu | Glu | Trp | Met | Gly |
|---|---|---|---|---|---|---|---|---|---|---|---|---|---|---|---|
| | | 35 | | | | | 40 | | | | | 45 | | | |

| Gly | Ile | Ile | Pro | Ile | Phe | Gly | Gln | Ala | Asn | Tyr | Ala | Gln | Lys | Phe | Gln |
|---|---|---|---|---|---|---|---|---|---|---|---|---|---|---|---|
| | 50 | | | | | 55 | | | | | 60 | | | | |

| Gly | Arg | Val | Thr | Ile | Thr | Ala | Asp | Glu | Ser | Thr | Asn | Thr | Ala | Tyr | Met |
|---|---|---|---|---|---|---|---|---|---|---|---|---|---|---|---|
| 65 | | | | | 70 | | | | | 75 | | | | | 80 |

| Glu | Leu | Arg | Ser | Leu | Arg | Ser | Asp | Asp | Thr | Ala | Met | Tyr | Tyr | Cys | Ala |
|---|---|---|---|---|---|---|---|---|---|---|---|---|---|---|---|
| | | | | 85 | | | | | 90 | | | | | 95 | |

| Lys | Glu | Gly | Tyr | Gly | Asp | Tyr | Gly | Arg | Pro | Phe | Asp | Phe | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser |
|---|---|---|---|---|---|---|---|
| | | 115 | | | | | 120 |

(2) INFORMATION FOR SEQ ID NO:14:

(i) SEQUENCE CHARACTERISTICS:
(A) LENGTH: 121 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: SIE (ix) FEATURE:
(A) NAME/KEY: Peptide
(B) LOCATION: 1..121

(ix) FEATURE:
(A) NAME/KEY: Peptide
(B) LOCATION: 1..121

(xi) SEQUENCE DESCRIPTION: SEQ ID NO:14:

| Val | Gln | Leu | Val | Gln | Ser | Gly | Ala | Glu | Val | Lys | Lys | Pro | Gly | Ser | Ser |
|---|---|---|---|---|---|---|---|---|---|---|---|---|---|---|---|
| 1 | | | | 5 | | | | | 10 | | | | | 15 | |

| Val | Arg | Val | Thr | Cys | Lys | Thr | Ser | Gly | Gly | Thr | Phe | Ser | Gly | Tyr | Thr |
|---|---|---|---|---|---|---|---|---|---|---|---|---|---|---|---|
| | | | 20 | | | | | 25 | | | | | 30 | | |

| Ile | Ser | Trp | Val | Arg | Gln | Ala | Pro | Gly | Arg | Gly | Leu | Glu | Trp | Val | Gly |
|---|---|---|---|---|---|---|---|---|---|---|---|---|---|---|---|
| | | 35 | | | | | 40 | | | | | 45 | | | |

| Ser | Pro | Ala | Lys | Trp | Thr | Asp | Pro | Phe | Gln | Gly | Val | Tyr | Ile | Lys | Trp |
|---|---|---|---|---|---|---|---|---|---|---|---|---|---|---|---|
| | 50 | | | | | 55 | | | | | 60 | | | | |

| Glu | Arg | Val | Thr | Val | Ser | Leu | Lys | Pro | Ser | Phe | Asn | Gln | Ala | Tyr | Met |
|---|---|---|---|---|---|---|---|---|---|---|---|---|---|---|---|
| 65 | | | | | 70 | | | | | 75 | | | | | 80 |

| Glu | Leu | Val | Asn | Leu | Phe | Asn | Glu | Asp | Gly | Ala | Val | Tyr | Tyr | Cys | Ala |
|---|---|---|---|---|---|---|---|---|---|---|---|---|---|---|---|

|  | | | | | 85 | | | | | 90 | | | | | 95 | |
|---|---|---|---|---|---|---|---|---|---|---|---|---|---|---|---|---|

Arg Glu Trp Lys Gly Gln Val Asn Val Asn Pro Phe Asp Tyr Trp Gly
            100                     105                     110

Gln Gly Val Leu Val Thr Val Ser Ser
            115                 120

(2) INFORMATION FOR SEQ ID NO:15:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: CESS (ix) FEATURE:
        (A) NAME/KEY: Peptide
        (B) LOCATION: 1..128

(xi) SEQUENCE DESCRIPTION: SEQ ID NO:15:

Gln Val Asn Leu Arg Glu Ser Gly Pro Ala Leu Val Lys Ala Thr His
1               5                   10                  15

Thr Leu Thr Leu Thr Cys Thr Phe Ser Gly Leu Ser Val Asn Thr Arg
            20                  25                  30

Gly Met Ser Val Ser Trp Ile Arg Gln Pro Pro Gly Lys Ala Leu Glu
            35                  40                  45

Trp Leu Ala Arg Ile Asp Trp Asp Asp Asp Lys Tyr Tyr Gly Thr Ser
            50                  55                  60

Leu Glu Thr Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
            85                  90                  95

Cys Ala Arg Met Gln Val Thr Met Val Arg Glu Val Met Ile Thr Ser
            100                 105                 110

Asn Ala Phe Asp Ile Trp Gly Gln Gly Thr Met Val Thr Val Ser Ser
            115                 120                 125

(2) INFORMATION FOR SEQ ID NO:16:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: LES (ix) FEATURE:
        (A) NAME/KEY: Peptide
        (B) LOCATION: 1..119

(xi) SEQUENCE DESCRIPTION: SEQ ID NO:16:

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Pro Phe Ser Gly Tyr
            20                  25                  30

Tyr Trp Ser Trp Val Arg Gln Pro Pro Gly Lys Gly Pro Glu Trp Ile
            35                  40                  45

| Gly | Glu | Ile | Asn | His | Ser | Gly | Arg | Thr | Thr | Tyr | Asn | Pro | Ser | Leu | Thr |
|---|---|---|---|---|---|---|---|---|---|---|---|---|---|---|---|
| | 50 | | | | 55 | | | | | | 60 | | | | |

| Ser | Arg | Val | Thr | Met | Ser | Leu | Asp | Thr | Ser | Lys | Asn | Gln | Phe | Ser | Leu |
|---|---|---|---|---|---|---|---|---|---|---|---|---|---|---|---|
| 65 | | | | | 70 | | | | 75 | | | | | | 80 |

| Lys | Leu | Thr | Ser | Val | Thr | Ala | Ala | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Gly | Pro | Cys | Glu | Ala | Tyr | Cys | Thr | Asp | Asp | Ala | Pro | Gln | Ala | Tyr |
|---|---|---|---|---|---|---|---|---|---|---|---|---|---|---|---|
| | | | 100 | | | | | 105 | | | | | 110 | | |

| Phe | Gln | His | Trp | Gly | Gln | Gly |
|---|---|---|---|---|---|---|
| | | | 115 | | | |

(2) INFORMATION FOR SEQ ID NO:17:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: A224

(ix) FEATURE:
        (A) NAME/KEY: Peptide
        (B) LOCATION: 1..98

(xi) SEQUENCE DESCRIPTION: SEQ ID NO:17:

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Thr | Ser | Gly | Tyr | Ser | Phe | Thr | Asn | Tyr |
|---|---|---|---|---|---|---|---|---|---|---|---|---|---|---|---|
| | | | 20 | | | | | 25 | | | | | 30 | | |

| Trp | Ile | Gly | Trp | Val | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Leu | Ile | Tyr | Pro | Gly | Asp | Ser | Gly | Thr | Arg | Tyr | Ser | Pro | Ser | Phe |
|---|---|---|---|---|---|---|---|---|---|---|---|---|---|---|---|
| | 50 | | | | | 55 | | | | | 60 | | | | |

| Lys | Gly | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | 75 | | | | | | 80 |

| Leu | Gln | Trp | Ser | Ser | Leu | Arg | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg |
|---|---|
| | |

(2) INFORMATION FOR SEQ ID NO:18:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: L16

(ix) FEATURE:
        (A) NAME/KEY: Peptide
        (B) LOCATION: 1..120

(xi) SEQUENCE DESCRIPTION: SEQ ID NO:18:

| Gln | Val | Gln | Leu | Gln | Gln | Ser | Gly | Pro | Gly | Leu | Val | Lys | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Ile | Ser | Gly | Asp | Ser | Val | Ser | Ser | Asn |
|---|---|---|---|---|---|---|---|---|---|---|---|---|---|---|---|

|  | 20 | 25 | 30 |
|---|---|---|---|

Ser Ala Ala Trp Asn Trp Ile Arg Gln Ser Pro Ser Arg Gly Leu Glu
          35                  40                  45

Trp Leu Gly Arg Thr Tyr Tyr Arg Ser Lys Trp Tyr Asn Asp Tyr Ala
 50                      55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
              85                  90                  95

Tyr Tyr Cys Ala Arg Glu Leu Gly Asp Ala Phe Asp Ile Trp Gly Gln
            100                 105                 110

Gly Thr Met Val Thr Val Ser Ser
          115             120

( 2 ) INFORMATION FOR SEQ ID NO:19:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SpA3-02

( i x ) FEATURE:
        ( A ) NAME/KEY: CDS
        ( B ) LOCATION: 1..360

( x i ) SEQUENCE DESCRIPTION: SEQ ID NO:19:

```
CAG GTG AAA CTG CTC GAG TCT GGG GGA GGA TTG GTA CAG CCT GGG GGG        48
Gln Val Lys Leu Leu Glu Ser Gly Gly Gly Leu Val Gln Pro Gly Gly
 1               5                  10                  15

TCC CTG AGA CTC TCC TGT GCA GCC TCT GGA TTC ACC TTT AGC AGC CAT        96
Ser Leu Arg Leu Ser Cys Ala Ala Ser Gly Phe Thr Phe Ser Ser His
             20                  25                  30

GCC ATG AGC TGG GTC CGC CAG GCT CCA GGG AAG GGC CTG GAG TGG GTC       144
Ala Met Ser Trp Val Arg Gln Ala Pro Gly Lys Gly Leu Glu Trp Val
         35                  40                  45

TCA GAT ATT AGT GCC AGT GGT GGT AGC ACA TAT TAT GCA GAC TCC GTG       192
Ser Asp Ile Ser Ala Ser Gly Gly Ser Thr Tyr Tyr Ala Asp Ser Val
     50                  55                  60

AAG GGC CGG TTC ACC ATC TCC AGA GAC AAT TCC AAG AAC ACG CTG TAT       240
Lys Gly Arg Phe Thr Ile Ser Arg Asp Asn Ser Lys Asn Thr Leu Tyr
 65                  70                  75                  80

TTG CAA ATG AAC AGC CTG AGA GCC GAA GAC ACG GCC TTA TAT TAC TGT       288
Leu Gln Met Asn Ser Leu Arg Ala Glu Asp Thr Ala Leu Tyr Tyr Cys
                 85                  90                  95

GCG TCC AAC GGC GCG GGA TGG GGG CTA CCT TCC CTT GAC TAC TGG GGC       336
Ala Ser Asn Gly Ala Gly Trp Gly Leu Pro Ser Leu Asp Tyr Trp Gly
            100                 105                 110

CAG GGA ACC CTG GTC ACC GTC TCC                                       360
Gln Gly Thr Leu Val Thr Val Ser
        115                 120
```

( 2 ) INFORMATION FOR SEQ ID NO:20:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| Gln | Val | Lys | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | His |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Asp | Ile | Ser | Ala | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Ser | Asn | Gly | Ala | Gly | Trp | Gly | Leu | Pro | Ser | Leu | Asp | Tyr | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser |
|---|---|---|---|---|---|---|---|
| | | 115 | | | | | 120 |

( 2 ) INFORMATION FOR SEQ ID NO:21:

( i ) SEQUENCE CHARACTERISTICS:
 ( A ) LENGTH: 360 base pairs
 ( B ) TYPE: nucleic acid
 ( C ) STRANDEDNESS: single
 ( D ) TOPOLOGY: linear ( i i ) MOLECULE TYPE: DNA (genomic)

( v i i ) IMMEDIATE SOURCE:
 ( B ) CLONE: SpA3-08

( i x ) FEATURE:
 ( A ) NAME/KEY: CDS
 ( B ) LOCATION: 1..360

( x i ) SEQUENCE DESCRIPTION: SEQ ID NO:21:

| CAG | GTG | AAA | CTG | CTC | GAG | TCT | GGG | GGA | GGA | TTG | GTA | CAG | CCT | GGG | GGG | 48 |
|---|---|---|---|---|---|---|---|---|---|---|---|---|---|---|---|---|
| Gln | Val | Lys | Leu | Leu | Glu | Ser | Gly | Gly | Gly | Leu | Val | Gln | Pro | Gly | Gly | |
| 1 | | | | 5 | | | | | 10 | | | | | 15 | | |

| TCC | CTG | AGA | CTC | TCC | TGT | GCA | GCC | TCT | GGA | TTC | ACC | TTT | AGC | AGC | CAT | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Ser | His | |
| | | | 20 | | | | | 25 | | | | | 30 | | | |

| GCC | ATG | AGC | TGG | GTC | CGC | CAG | GCT | CCA | GGG | AAG | GGC | CTG | GAG | TGG | GTC | 144 |
|---|---|---|---|---|---|---|---|---|---|---|---|---|---|---|---|---|
| Ala | Met | Ser | Trp | Val | Arg | Gln | Ala | Pro | Gly | Lys | Gly | Leu | Glu | Trp | Val | |
| | | 35 | | | | | 40 | | | | | 45 | | | | |

| TCA | GAT | ATT | AGT | GCC | AGT | GGT | GGT | AGC | ACA | TAT | TAT | GCA | GAC | TCC | GTG | 192 |
|---|---|---|---|---|---|---|---|---|---|---|---|---|---|---|---|---|
| Ser | Asp | Ile | Ser | Ala | Ser | Gly | Gly | Ser | Thr | Tyr | Tyr | Ala | Asp | Ser | Val | |
| | 50 | | | | | 55 | | | | | 60 | | | | | |

| AAG | GGC | CGG | TTC | ACC | ATC | TCC | AGA | GAC | AAT | TCC | AAG | AAC | ACG | CTG | TAT | 240 |
|---|---|---|---|---|---|---|---|---|---|---|---|---|---|---|---|---|
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |

| TTG | CAA | ATG | AAC | AGC | CTG | AGA | GCC | GAA | GAC | ACG | GCC | TTA | TAT | TAC | TGT | 288 |
|---|---|---|---|---|---|---|---|---|---|---|---|---|---|---|---|---|
| Leu | Gln | Met | Asn | Ser | Leu | Arg | Ala | Glu | Asp | Thr | Ala | Leu | Tyr | Tyr | Cys | |
| | | | | 85 | | | | | 90 | | | | | 95 | | |

| GCG | TCC | AGC | GGC | GCG | GGA | TGG | GGG | CTA | CCT | TCC | CTT | GAC | TAC | TGG | GGC | 336 |
|---|---|---|---|---|---|---|---|---|---|---|---|---|---|---|---|---|
| Ala | Ser | Ser | Gly | Ala | Gly | Trp | Gly | Leu | Pro | Ser | Leu | Asp | Tyr | Trp | Gly | |
| | | | 100 | | | | | 105 | | | | | 110 | | | |

| CAG | GGA | ACC | CTG | GTC | ACC | GTC | TCC | 360 |
|---|---|---|---|---|---|---|---|---|
| Gln | Gly | Thr | Leu | Val | Thr | Val | Ser | |
| | | 115 | | | | | 120 | |

( 2 ) INFORMATION FOR SEQ ID NO:22:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Gln Val Lys Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Asp Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Ser Ser Gly Ala Gly Trp Gly Leu Pro Ser Leu Asp Tyr Trp Gly
            100                 105                 110

Gln Gly Thr Leu Val Thr Val Ser
            115                 120
```

( 2 ) INFORMATION FOR SEQ ID NO:23:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SpA3-13

( i x ) FEATURE:
        ( A ) NAME/KEY: CDS
        ( B ) LOCATION: 1..360

( x i ) SEQUENCE DESCRIPTION: SEQ ID NO:23:

```
CAG GTG AAA CTG CTC GAG TCT GGG GGA GGA TTG GTA CAG CCT GGG GGG      48
Gln Val Lys Leu Leu Glu Ser Gly Gly Gly Leu Val Gln Pro Gly Gly
 1               5                  10                  15

TCC CTG AGA CTC TCC TGT GCA GCC TCT GGA TTC ACC TTT AGC AGC CAT      96
Ser Leu Arg Leu Ser Cys Ala Ala Ser Gly Phe Thr Phe Ser Ser His
            20                  25                  30

GCC ATG AGC TGG GTC CGC CAG GCT CCA GGG AGG GGC CTG GAG TGG GTC     144
Ala Met Ser Trp Val Arg Gln Ala Pro Gly Arg Gly Leu Glu Trp Val
        35                  40                  45

TCA GAT ATT AGT GCC AGT GGT GGT AGC ACA TAT TAT GCA GAC TCC GTG     192
Ser Asp Ile Ser Ala Ser Gly Gly Ser Thr Tyr Tyr Ala Asp Ser Val
    50                  55                  60

AAG GGC CGG TTC ACC ATC TCC AGA GAC AAT TCC AAG AAC ACG CTG TAT     240
Lys Gly Arg Phe Thr Ile Ser Arg Asp Asn Ser Lys Asn Thr Leu Tyr
65                  70                  75                  80

TTG CAA ATG AAC AGC CTG AGA GCC GAA GAC ACG GCC TTA TAT TAC TGT     288
Leu Gln Met Asn Ser Leu Arg Ala Glu Asp Thr Ala Leu Tyr Tyr Cys
                85                  90                  95
```

| GCG | TCC | AAC | GGC | GCG | GGA | TGG | GGG | CTA | CCT | TCC | CTT | GAC | TAC | TGG | GGC | 336 |
|-----|-----|-----|-----|-----|-----|-----|-----|-----|-----|-----|-----|-----|-----|-----|-----|-----|
| Ala | Ser | Asn | Gly | Ala | Gly | Trp | Gly | Leu | Pro | Ser | Leu | Asp | Tyr | Trp | Gly | |
| | | | 100 | | | | 105 | | | | | 110 | | | | |

| CAG | GGA | ACC | CTG | GTC | ACC | GTC | TCC | 360 |
|-----|-----|-----|-----|-----|-----|-----|-----|-----|
| Gln | Gly | Thr | Leu | Val | Thr | Val | Ser | |
| | | 115 | | | | | 120 | |

(2) INFORMATION FOR SEQ ID NO:24:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:24:

| Gln | Val | Lys | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | His |
|-----|-----|-----|-----|-----|-----|-----|-----|-----|-----|-----|-----|-----|-----|-----|-----|
| | | | 20 | | | | | 25 | | | | | 30 | | |

| Ala | Met | Ser | Trp | Val | Arg | Gln | Ala | Pro | Gly | Arg | Gly | Leu | Glu | Trp | Val |
|-----|-----|-----|-----|-----|-----|-----|-----|-----|-----|-----|-----|-----|-----|-----|-----|
| | | 35 | | | | | 40 | | | | | 45 | | | |

| Ser | Asp | Ile | Ser | Ala | Ser | Gly | Gly | Ser | Thr | Tyr | Tyr | Ala | Asp | Ser | Val |
|-----|-----|-----|-----|-----|-----|-----|-----|-----|-----|-----|-----|-----|-----|-----|-----|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|-----|-----|-----|-----|-----|-----|-----|-----|-----|-----|-----|-----|-----|-----|-----|-----|
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
|-----|-----|-----|-----|-----|-----|-----|-----|-----|-----|-----|-----|-----|-----|-----|-----|
| | | | | 85 | | | | | 90 | | | | | 95 | |

| Ala | Ser | Asn | Gly | Ala | Gly | Trp | Gly | Leu | Pro | Ser | Leu | Asp | Tyr | Trp | Gly |
|-----|-----|-----|-----|-----|-----|-----|-----|-----|-----|-----|-----|-----|-----|-----|-----|
| | | | 100 | | | | 105 | | | | | 110 | | | |

| Gln | Gly | Thr | Leu | Val | Thr | Val | Ser |
|-----|-----|-----|-----|-----|-----|-----|-----|
| | | 115 | | | | | 120 |

(2) INFORMATION FOR SEQ ID NO:25:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: SpA3-15

(ix) FEATURE:
        (A) NAME/KEY: CDS
        (B) LOCATION: 1..360

(xi) SEQUENCE DESCRIPTION: SEQ ID NO:25:

| CAG | GTG | AAA | CTG | CTC | GAG | TCT | GGG | GGA | GGA | TTG | GTA | CAG | CCT | GGG | GGG | 48 |
|-----|-----|-----|-----|-----|-----|-----|-----|-----|-----|-----|-----|-----|-----|-----|-----|-----|
| Gln | Val | Lys | Leu | Leu | Glu | Ser | Gly | Gly | Gly | Leu | Val | Gln | Pro | Gly | Gly | |
| 1 | | | | 5 | | | | | 10 | | | | | 15 | | |

| TCC | CTG | AGA | CTC | TCC | TGT | GCA | GCC | TCT | GGA | TTC | ACC | TTT | AGC | AGC | CAT | 96 |
|-----|-----|-----|-----|-----|-----|-----|-----|-----|-----|-----|-----|-----|-----|-----|-----|-----|
| Ser | Leu | Arg | Leu | Ser | Cys | Ala | Ala | Ser | Gly | Phe | Thr | Phe | Ser | Ser | His | |
| | | | 20 | | | | | 25 | | | | | 30 | | | |

| GCC | ATG | AGC | TGG | GTC | CGC | CAG | GCT | CCA | GGG | AGG | GGC | CTG | GAG | TGG | GTC | 144 |
|-----|-----|-----|-----|-----|-----|-----|-----|-----|-----|-----|-----|-----|-----|-----|-----|-----|
| Ala | Met | Ser | Trp | Val | Arg | Gln | Ala | Pro | Gly | Arg | Gly | Leu | Glu | Trp | Val | |
| | | 35 | | | | | 40 | | | | | 45 | | | | |

| TCA | GAT | ATT | AGT | GCC | AGT | GGT | GGT | AGC | ACA | TAT | TAT | GCA | GAC | TCC | GTG | 192 |
|-----|-----|-----|-----|-----|-----|-----|-----|-----|-----|-----|-----|-----|-----|-----|-----|-----|
| Ser | Asp | Ile | Ser | Ala | Ser | Gly | Gly | Ser | Thr | Tyr | Tyr | Ala | Asp | Ser | Val | |
| | 50 | | | | | 55 | | | | | 60 | | | | | |

-continued

| | | | | | | | | | | | | | | | |
|---|---|---|---|---|---|---|---|---|---|---|---|---|---|---|---|
| AAG | GGC | CGG | TTC | ACC | ATC | TCC | AGA | GAC | AAT | TCC | AAG | AAC | ACG | CTG | TAT | 240 |
| Lys | Gly | Arg | Phe | Thr | Ile | Ser | Arg | Asp | Asn | Ser | Lys | Asn | Thr | Leu | Tyr |
| 65 | | | | 70 | | | | | 75 | | | | | 80 |
| TTG | CAA | ATG | AAC | AGC | CTG | AGA | GCC | GAA | GAC | ACG | GCC | TTA | TAT | TAC | TGT | 288 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 |
| GCG | TCC | AAC | GGC | GCG | GGA | TGG | GGG | CTA | CCT | TCC | CTT | GAC | TAC | TGG | GGC | 336 |
| Ala | Ser | Asn | Gly | Ala | Gly | Trp | Gly | Leu | Pro | Ser | Leu | Asp | Tyr | Trp | Gly |
| | | | 100 | | | | | 105 | | | | | 110 |
| CAG | GGA | ACC | CTG | GTC | ACC | GTC | TCC | | | | | | | | | 360 |
| Gln | Gly | Thr | Leu | Val | Thr | Val | Ser |
| | | 115 | | | | | 120 |

(2) INFORMATION FOR SEQ ID NO:26:

(i) SEQUENCE CHARACTERISTICS:
  (A) LENGTH: 120 amino acids
  (B) TYPE: amino acid
  (D) TOPOLOGY: linear (ii) MOLECULE TYPE: protein (xi) SEQUENCE DESCRIPTION: SEQ ID NO:26:

| | | | | | | | | | | | | | | |
|---|---|---|---|---|---|---|---|---|---|---|---|---|---|---|
| Gln | Val | Lys | Leu | Leu | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | His |
| | | | 20 | | | | | 25 | | | | | 30 |
| Ala | Met | Ser | Trp | Val | Arg | Gln | Ala | Pro | Gly | Arg | Gly | Leu | Glu | Trp | Val |
| | | | 35 | | | | | 40 | | | | | 45 |
| Ser | Asp | Ile | Ser | Ala | Ser | Gly | Gly | Ser | Thr | Tyr | Tyr | Ala | Asp | Ser | Val |
| | | | 50 | | | | | 55 | | | | | 60 |
| Lys | Gly | Arg | Phe | Thr | Ile | Ser | Arg | Asp | Asn | Ser | Lys | Asn | Thr | Leu | Tyr |
| 65 | | | | 70 | | | | | 75 | | | | | 80 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 |
| Ala | Ser | Asn | Gly | Ala | Gly | Trp | Gly | Leu | Pro | Ser | Leu | Asp | Tyr | Trp | Gly |
| | | | 100 | | | | | 105 | | | | | 110 |
| Gln | Gly | Thr | Leu | Val | Thr | Val | Ser |
| | | 115 | | | | | 120 |

(2) INFORMATION FOR SEQ ID NO:27:

(i) SEQUENCE CHARACTERISTICS:
  (A) LENGTH: 360 base pairs
  (B) TYPE: nucleic acid
  (C) STRANDEDNESS: single
  (D) TOPOLOGY: linear (ii) MOLECULE TYPE: DNA (genomic)

(vii) IMMEDIATE SOURCE:
  (B) CLONE: SpA3-16

(ix) FEATURE:
  (A) NAME/KEY: CDS
  (B) LOCATION: 1..360

(xi) SEQUENCE DESCRIPTION: SEQ ID NO:27:

| | | | | | | | | | | | | | | | |
|---|---|---|---|---|---|---|---|---|---|---|---|---|---|---|---|
| CAG | GTG | AAA | CTG | CTC | GAG | TCT | GGG | GGA | GGA | TTG | GTA | CAG | CCT | GGG | GGG | 48 |
| Gln | Val | Lys | Leu | Leu | Glu | Ser | Gly | Gly | Gly | Leu | Val | Gln | Pro | Gly | Gly |
| 1 | | | | 5 | | | | | 10 | | | | | 15 |
| TCC | CTG | AGA | CTC | TCC | TGT | GCA | GCC | TCT | GGA | TTC | ACC | TTT | AGC | AGC | CAT | 96 |
| Ser | Leu | Arg | Leu | Ser | Cys | Ala | Ala | Ser | Gly | Phe | Thr | Phe | Ser | Ser | His |
| | | | 20 | | | | | 25 | | | | | 30 |

| GCC | ATG | AGC | TGG | GTC | CGC | CAG | GCT | CCA | GGG | AGG | GGC | CTG | GAG | TGG | GTC | 144 |
| Ala | Met | Ser | Trp | Val | Arg | Gln | Ala | Pro | Gly | Arg | Gly | Leu | Glu | Trp | Val | |
| | | 35 | | | | 40 | | | | | 45 | | | | | |

| TCA | GAT | ATT | AGT | GCC | AGT | GGT | GGT | AGC | ACA | TAT | TAT | GCA | GAC | TCC | GTG | 192 |
| Ser | Asp | Ile | Ser | Ala | Ser | Gly | Gly | Ser | Thr | Tyr | Tyr | Ala | Asp | Ser | Val | |
| | 50 | | | | | 55 | | | | | 60 | | | | | |

| AAG | GGC | CGG | TTC | ACC | ATC | TCC | AGA | GAC | AAT | TCC | AAG | AAC | ACG | CTG | TAT | 240 |
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |

| TTG | CAA | ATG | AAC | AGC | CTG | AGA | GCC | GAA | GAC | ACG | GCC | TTA | TAT | TAC | TGT | 288 |
| Leu | Gln | Met | Asn | Ser | Leu | Arg | Ala | Glu | Asp | Thr | Ala | Leu | Tyr | Tyr | Cys | |
| | | | | 85 | | | | | 90 | | | | | 95 | | |

| GCG | TCC | AAC | GGC | GCG | GGA | TGG | GGG | CTA | CCT | TCC | CTT | GAC | TAC | TGG | GGC | 336 |
| Ala | Ser | Asn | Gly | Ala | Gly | Trp | Gly | Leu | Pro | Ser | Leu | Asp | Tyr | Trp | Gly | |
| | | | 100 | | | | | 105 | | | | | 110 | | | |

| CAG | GGA | ACC | CTG | GTC | ACC | GTC | TCC | | | | | | | | | 360 |
| Gln | Gly | Thr | Leu | Val | Thr | Val | Ser | | | | | | | | | |
| | | 115 | | | | | 120 | | | | | | | | | |

( 2 ) INFORMATION FOR SEQ ID NO:28:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| Gln | Val | Lys | Leu | Leu | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | His |
| | | | 20 | | | | | 25 | | | | | 30 | | |

| Ala | Met | Ser | Trp | Val | Arg | Gln | Ala | Pro | Gly | Arg | Gly | Leu | Glu | Trp | Val |
| | | 35 | | | | 40 | | | | | 45 | | | | |

| Ser | Asp | Ile | Ser | Ala | Ser | Gly | Gly | Ser | Thr | Tyr | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |

| Ala | Ser | Asn | Gly | Ala | Gly | Trp | Gly | Leu | Pro | Ser | Leu | Asp | Tyr | Trp | Gly |
| | | | 100 | | | | | 105 | | | | | 110 | | |

| Gln | Gly | Thr | Leu | Val | Thr | Val | Ser |
| | | 115 | | | | | 120 |

( 2 ) INFORMATION FOR SEQ ID NO:29:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SpA3-18

( i x ) FEATURE:
        ( A ) NAME/KEY: CDS
        ( B ) LOCATION: 1..360

( x i ) SEQUENCE DESCRIPTION: SEQ ID NO:29:

| | | | | | | | | | | | | | | | | |
|---|---|---|---|---|---|---|---|---|---|---|---|---|---|---|---|---|
| GTG | AAA | CTG | CTC | GAG | GAG | TCT | GGG | GGA | GGA | TTG | GTA | CAG | CCT | GGG | GGG | 48 |
| Val | Lys | Leu | Leu | Glu | Glu | Ser | Gly | Gly | Gly | Leu | Val | Gln | Pro | Gly | Gly | |
| 1 | | | | 5 | | | | | 10 | | | | | 15 | | |
| TCC | CTG | AGA | CTC | TCC | TGT | GCA | GCC | TCT | GGA | TTC | ACC | TTT | AGC | AGC | CAT | 96 |
| Ser | Leu | Arg | Leu | Ser | Cys | Ala | Ala | Ser | Gly | Phe | Thr | Phe | Ser | Ser | His | |
| | | | 20 | | | | | 25 | | | | | 30 | | | |
| GCC | ATG | AGC | TGG | GTC | CGC | CAG | GCT | CCA | GGG | AGG | GGC | CTG | GAG | TGG | GTC | 144 |
| Ala | Met | Ser | Trp | Val | Arg | Gln | Ala | Pro | Gly | Arg | Gly | Leu | Glu | Trp | Val | |
| | | 35 | | | | | 40 | | | | | 45 | | | | |
| TCA | GAT | ATT | AGT | GCC | AGT | GGT | GGT | AGC | ACA | TAT | TAT | GCA | GAC | TCC | GTG | 192 |
| Ser | Asp | Ile | Ser | Ala | Ser | Gly | Gly | Ser | Thr | Tyr | Tyr | Ala | Asp | Ser | Val | |
| | 50 | | | | | 55 | | | | | 60 | | | | | |
| AAG | GGC | CGG | TTC | ACC | ATC | TCC | AGA | GAC | AAT | TCC | AAG | AAC | ACG | CTG | TAT | 240 |
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |
| TTG | CAA | ATG | AAC | AGC | CTG | AGA | GCC | GAA | GAC | ACG | GCC | TTA | TAT | TAC | TGT | 288 |
| Leu | Gln | Met | Asn | Ser | Leu | Arg | Ala | Glu | Asp | Thr | Ala | Leu | Tyr | Tyr | Cys | |
| | | | | 85 | | | | | 90 | | | | | 95 | | |
| GCG | TCC | AAC | GGC | GCG | GGA | TGG | GGG | CTA | CCT | TCC | CTT | GAC | TAC | TGG | GGC | 336 |
| Ala | Ser | Asn | Gly | Ala | Gly | Trp | Gly | Leu | Pro | Ser | Leu | Asp | Tyr | Trp | Gly | |
| | | | 100 | | | | | 105 | | | | | 110 | | | |
| CAG | GGA | ACC | CTG | GTC | ACC | GTC | TCC | | | | | | | | | 360 |
| Gln | Gly | Thr | Leu | Val | Thr | Val | Ser | | | | | | | | | |
| | | 115 | | | | | 120 | | | | | | | | | |

( 2 ) INFORMATION FOR SEQ ID NO:30:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | | |
|---|---|---|---|---|---|---|---|---|---|---|---|---|---|---|---|
| Val | Lys | Leu | Leu | Glu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | His |
| | | | 20 | | | | | 25 | | | | | 30 | | |
| Ala | Met | Ser | Trp | Val | Arg | Gln | Ala | Pro | Gly | Arg | Gly | Leu | Glu | Trp | Val |
| | | 35 | | | | | 40 | | | | | 45 | | | |
| Ser | Asp | Ile | Ser | Ala | Ser | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |
| Ala | Ser | Asn | Gly | Ala | Gly | Trp | Gly | Leu | Pro | Ser | Leu | Asp | Tyr | Trp | Gly |
| | | | 100 | | | | | 105 | | | | | 110 | | |
| Gln | Gly | Thr | Leu | Val | Thr | Val | Ser | | | | | | | | |
| | | 115 | | | | | 120 | | | | | | | | |

( 2 ) INFORMATION FOR SEQ ID NO:31:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:

(B) CLONE: SpA3-39

(ix) FEATURE:
    (A) NAME/KEY: CDS
    (B) LOCATION: 1..360

(xi) SEQUENCE DESCRIPTION: SEQ ID NO:31:

```
GTG AAA CTG CTC GAG GAG TCT GGG GGA GGA TTG GTA CAG CCT GGG GGG        48
Val Lys Leu Leu Glu Glu Ser Gly Gly Gly Leu Val Gln Pro Gly Gly
 1               5                  10                  15

TCC CTG AGA CTC TCC TGT GCA GCC TCT GGA TTC ACC TTT AGC AGC CAT        96
Ser Leu Arg Leu Ser Cys Ala Ala Ser Gly Phe Thr Phe Ser Ser His
             20                  25                  30

GCC ATG AGC TGG GTC CGC CAG GCT CCA GGG AGG GGC CTG GAG TGG GTC       144
Ala Met Ser Trp Val Arg Gln Ala Pro Gly Arg Gly Leu Glu Trp Val
         35                  40                  45

TCA GAT ATT AGT GCC AGT GGT GGT AGC ACA TAT TAT GCA GAC TCC GTG       192
Ser Asp Ile Ser Ala Ser Gly Gly Ser Thr Tyr Tyr Ala Asp Ser Val
     50                  55                  60

AAG GGC CGG TTC ACC ATC TCC AGA GAC AAT TCC AAG AAC ACG CTG TAT       240
Lys Gly Arg Phe Thr Ile Ser Arg Asp Asn Ser Lys Asn Thr Leu Tyr
 65                  70                  75                  80

TTG CAA ATG AAC AGC CTG AGA GCC GAA GAC ACG GCC TTA TAT TAC TGT       288
Leu Gln Met Asn Ser Leu Arg Ala Glu Asp Thr Ala Leu Tyr Tyr Cys
             85                  90                  95

GCG TCC AAC GGC GCG GGA TGG GGG CTA CCT TCC CTT GAC TAC TGG GGC       336
Ala Ser Asn Gly Ala Gly Trp Gly Leu Pro Ser Leu Asp Tyr Trp Gly
        100                 105                 110

CAG GGA ACC CTG GTC ACC GTC TCC                                       360
Gln Gly Thr Leu Val Thr Val Ser
        115                 120
```

(2) INFORMATION FOR SEQ ID NO:32:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:32:

```
Val Lys Leu Leu Glu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
             20                  25                  30

Ala Met Ser Trp Val Arg Gln Ala Pro Gly Arg Gly Leu Glu Trp Val
         35                  40                  45

Ser Asp Ile Ser Ala Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
             85                  90                  95

Ala Ser Asn Gly Ala Gly Trp Gly Leu Pro Ser Leu Asp Tyr Trp Gly
        100                 105                 110

Gln Gly Thr Leu Val Thr Val Ser
        115                 120
```

(2) INFORMATION FOR SEQ ID NO:33:

(i) SEQUENCE CHARACTERISTICS:

(A) LENGTH: 360 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: SpA3-37

(ix) FEATURE:
        (A) NAME/KEY: CDS
        (B) LOCATION: 1..360

(xi) SEQUENCE DESCRIPTION: SEQ ID NO:33:

```
CAG  GTG  AAA  CTG  CTC  GAG  TCT  GGG  GGA  GGA  TTG  GTA  CAG  CCT  GGG  GGG    48
Gln  Val  Lys  Leu  Leu  Glu  Ser  Gly  Gly  Gly  Leu  Val  Gln  Pro  Gly  Gly
 1                  5                       10                      15

TCC  CTG  AGA  CTC  TCC  TGT  GCA  GCC  TCT  GGA  TTC  ACC  TTT  AGC  AGC  CAT    96
Ser  Leu  Arg  Leu  Ser  Cys  Ala  Ala  Ser  Gly  Phe  Thr  Phe  Ser  Ser  His
                 20                      25                      30

GCC  ATG  AGC  TGG  GTC  CGC  CAG  GCT  CCA  GGG  AGG  GGC  CTG  GAG  TGG  GTC   144
Ala  Met  Ser  Trp  Val  Arg  Gln  Ala  Pro  Gly  Arg  Gly  Leu  Glu  Trp  Val
          35                      40                      45

TCA  GAT  ATT  AGT  GCC  AGT  GGT  GGT  AGC  ACA  TAT  TAT  GCA  GAC  TCC  GTG   192
Ser  Asp  Ile  Ser  Ala  Ser  Gly  Gly  Ser  Thr  Tyr  Tyr  Ala  Asp  Ser  Val
     50                      55                      60

AAG  GGC  CGG  TTC  ACC  ATC  TCC  AGA  GAC  AAT  TCC  AAG  AAC  ACG  CTG  TAT   240
Lys  Gly  Arg  Phe  Thr  Ile  Ser  Arg  Asp  Asn  Ser  Lys  Asn  Thr  Leu  Tyr
 65                      70                      75                      80

TTG  CAA  ATG  AAC  AGC  CTG  AGA  GCC  GAA  GAC  ACG  GCC  TTA  TAT  TAC  TGT   288
Leu  Gln  Met  Asn  Ser  Leu  Arg  Ala  Glu  Asp  Thr  Ala  Leu  Tyr  Tyr  Cys
                 85                      90                      95

GCG  TCC  AAC  GGC  GCG  GGA  TGG  GGG  CTA  CCT  TCC  CTT  GAC  TAC  TTG  GGC   336
Ala  Ser  Asn  Gly  Ala  Gly  Trp  Gly  Leu  Pro  Ser  Leu  Asp  Tyr  Leu  Gly
          100                     105                     110

GAG  GGA  ACC  CTG  GTC  ACC  GTC  TCC                                            360
Glu  Gly  Thr  Leu  Val  Thr  Val  Ser
          115                     120
```

(2) INFORMATION FOR SEQ ID NO:34:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:34:

```
Gln  Val  Lys  Leu  Leu  Glu  Ser  Gly  Gly  Gly  Leu  Val  Gln  Pro  Gly  Gly
 1                  5                       10                      15

Ser  Leu  Arg  Leu  Ser  Cys  Ala  Ala  Ser  Gly  Phe  Thr  Phe  Ser  Ser  His
                 20                      25                      30

Ala  Met  Ser  Trp  Val  Arg  Gln  Ala  Pro  Gly  Arg  Gly  Leu  Glu  Trp  Val
          35                      40                      45

Ser  Asp  Ile  Ser  Ala  Ser  Gly  Gly  Ser  Thr  Tyr  Tyr  Ala  Asp  Ser  Val
     50                      55                      60

Lys  Gly  Arg  Phe  Thr  Ile  Ser  Arg  Asp  Asn  Ser  Lys  Asn  Thr  Leu  Tyr
 65                      70                      75                      80

Leu  Gln  Met  Asn  Ser  Leu  Arg  Ala  Glu  Asp  Thr  Ala  Leu  Tyr  Tyr  Cys
                 85                      90                      95

Ala  Ser  Asn  Gly  Ala  Gly  Trp  Gly  Leu  Pro  Ser  Leu  Asp  Tyr  Leu  Gly
          100                     105                     110
```

Glu Gly Thr Leu Val Thr Val Ser
115                         120

(2) INFORMATION FOR SEQ ID NO:35:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: SpA3-33

(ix) FEATURE:
        (A) NAME/KEY: CDS
        (B) LOCATION: 1..351

(xi) SEQUENCE DESCRIPTION: SEQ ID NO:35:

| GTG | AAA | CTG | CTC | GAG | GAG | TCT | GGG | GGA | GGC | TTG | GTA | CAG | CCT | GGG | GTG | 48 |
| Val | Lys | Leu | Leu | Glu | Glu | Ser | Gly | Gly | Gly | Leu | Val | Gln | Pro | Gly | Val | |
| 1 | | | | 5 | | | | | 10 | | | | | 15 | | |

| CCC | CTG | AGA | CTC | TCC | TGT | GAA | GCC | TCT | GGA | TTC | CCC | TTC | AGT | AAC | TAT | 96 |
| Pro | Leu | Arg | Leu | Ser | Cys | Glu | Ala | Ser | Gly | Phe | Pro | Phe | Ser | Asn | Tyr | |
| | | | 20 | | | | | 25 | | | | | 30 | | | |

| GGC | ATG | AGC | TGG | GTC | CGC | CAG | GCT | CCA | GGG | AAG | GGG | CTG | GAG | TGG | GTC | 144 |
| Gly | Met | Ser | Trp | Val | Arg | Gln | Ala | Pro | Gly | Lys | Gly | Leu | Glu | Trp | Val | |
| | | 35 | | | | | 40 | | | | | 45 | | | | |

| TCA | AGT | ATT | AGT | GGA | AGT | GGT | GAT | AGT | ACA | TAC | TAC | GCC | GAC | TCC | GTG | 192 |
| Ser | Ser | Ile | Ser | Gly | Ser | Gly | Asp | Ser | Thr | Tyr | Tyr | Ala | Asp | Ser | Val | |
| | 50 | | | | | 55 | | | | | 60 | | | | | |

| AAG | GGC | CGG | TTC | ACC | ATC | TCC | AGA | GAC | AAC | GCC | AAG | AAC | TCA | CTG | TAT | 240 |
| Lys | Gly | Arg | Phe | Thr | Ile | Ser | Arg | Asp | Asn | Ala | Lys | Asn | Ser | Leu | Tyr | |
| 65 | | | | | 70 | | | | | 75 | | | | | 80 | |

| CTG | CAA | ATG | AAC | AGC | CTG | AGA | GCC | GAA | GAC | ACG | GCT | GTG | TAT | TAC | TGT | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| GCG | AGA | GAT | GCA | TGG | GAT | GCA | TTT | GAT | ATC | TGG | GGC | CAA | GGG | ACA | ATG | 336 |
| Ala | Arg | Asp | Ala | Trp | Asp | Ala | Phe | Asp | Ile | Trp | Gly | Gln | Gly | Thr | Met | |
| | | | 100 | | | | | 105 | | | | | 110 | | | |

| GTC | ACA | GTC | TCC | TCA | | | | | | | | | | | | 351 |
| Val | Thr | Val | Ser | Ser | | | | | | | | | | | | |
| | | 115 | | | | | | | | | | | | | | |

(2) INFORMATION FOR SEQ ID NO:36:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:36:

Val Lys Leu Leu Glu Glu Ser Gly Gly Gly Leu Val Gln Pro Gly Val
1               5                   10                  15

Pro Leu Arg Leu Ser Cys Glu Ala Ser Gly Phe Pro Phe Ser Asn Tyr
            20                  25                  30

Gly Met Ser Trp Val Arg Gln Ala Pro Gly Lys Gly Leu Glu Trp Val
        35                  40                  45

Ser Ser Ile Ser Gly Ser Gly Asp Ser Thr Tyr Tyr Ala Asp Ser Val
    50                  55                  60

| | | | | | | | | | | | | | | | |
|---|---|---|---|---|---|---|---|---|---|---|---|---|---|---|---|
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Asp | Ala | Trp | Asp | Ala | Phe | Asp | Ile | Trp | Gly | Gln | Gly | Thr | Met |
| | | | 100 | | | | | 105 | | | | | 110 | | |
| Val | Thr | Val | Ser | Ser | | | | | | | | | | | |
| | | 115 | | | | | | | | | | | | | |

( 2 ) INFORMATION FOR SEQ ID NO:37:

( i ) SEQUENCE CHARACTERISTICS:
    ( A ) LENGTH: 369 base pairs
    ( B ) TYPE: nucleic acid
    ( C ) STRANDEDNESS: single
    ( D ) TOPOLOGY: linear ( i i ) MOLECULE TYPE: DNA (genomic)

( v i i ) IMMEDIATE SOURCE:
    ( B ) CLONE: SpA2-08

( i x ) FEATURE:
    ( A ) NAME/KEY: CDS
    ( B ) LOCATION: 1..369

( x i ) SEQUENCE DESCRIPTION: SEQ ID NO:37:

| | | | | | | | | | | | | | | | | |
|---|---|---|---|---|---|---|---|---|---|---|---|---|---|---|---|---|
| CAG | GTG | AAA | CTG | CTC | GAG | TCT | GGG | GGA | ACC | TTG | GTA | CAG | CCG | GGG | GGG | 48 |
| Gln | Val | Lys | Leu | Leu | Glu | Ser | Gly | Gly | Thr | Leu | Val | Gln | Pro | Gly | Gly | |
| 1 | | | | 5 | | | | | 10 | | | | | 15 | | |
| TCC | CTG | AGA | CTC | TCC | TGT | GCA | GCC | TCT | GGA | TTC | ACC | TTT | AGC | AGC | TAT | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |
| GCC | ATG | AGC | TGG | GTC | CGC | CAG | GCT | CCA | GGG | AAG | GGG | CTG | GAG | TGG | GTC | 144 |
| Ala | Met | Ser | Trp | Val | Arg | Gln | Ala | Pro | Gly | Lys | Gly | Leu | Glu | Trp | Val | |
| | | 35 | | | | | 40 | | | | | 45 | | | | |
| TCA | GCT | ATT | AGT | GGT | AGT | GGT | GGT | AGC | ACA | TAC | TAC | GCA | GAC | TCC | GTG | 192 |
| Ser | Ala | Ile | Ser | Gly | Ser | Gly | Gly | Ser | Thr | Tyr | Tyr | Ala | Asp | Ser | Val | |
| | 50 | | | | | 55 | | | | | 60 | | | | | |
| AAG | GGC | CTA | TTC | ACC | ATC | TCC | AGA | GAC | AAC | GCC | AAG | AAC | ACG | CTG | TAT | 240 |
| Lys | Gly | Leu | Phe | Thr | Ile | Ser | Arg | Asp | Asn | Ala | Lys | Asn | Thr | Leu | Tyr | |
| 65 | | | | | 70 | | | | | 75 | | | | | 80 | |
| CTG | CAG | CTG | AAC | AGT | CTG | AGA | GCC | GAG | GAC | ACG | GCT | GTG | TAT | TAC | TGT | 288 |
| Leu | Gln | Leu | Asn | Ser | Leu | Arg | Ala | Glu | Asp | Thr | Ala | Val | Tyr | Tyr | Cys | |
| | | | | 85 | | | | | 90 | | | | | 95 | | |
| GCA | AGA | GCC | GAG | TTA | GGA | GGA | CTG | ATG | GTT | ATC | GTA | ACC | CCC | TCT | GAG | 336 |
| Ala | Arg | Ala | Glu | Leu | Gly | Gly | Leu | Met | Val | Ile | Val | Thr | Pro | Ser | Glu | |
| | | | 100 | | | | | 105 | | | | | 110 | | | |
| TAC | TGG | GGC | CAG | GGA | ACC | CTG | GTC | ACC | GTC | TCC | | | | | | 369 |
| Tyr | Trp | Gly | Gln | Gly | Thr | Leu | Val | Thr | Val | Ser | | | | | | |
| | | 115 | | | | | 120 | | | | | | | | | |

( 2 ) INFORMATION FOR SEQ ID NO:38:

( i ) SEQUENCE CHARACTERISTICS:
    ( A ) LENGTH: 123 amino acids
    ( B ) TYPE: amino acid
    ( D ) TOPOLOGY: linear ( i i ) MOLECULE TYPE: protein ( x i ) SEQUENCE DESCRIPTION: SEQ ID NO:38:

| | | | | | | | | | | | | | | | |
|---|---|---|---|---|---|---|---|---|---|---|---|---|---|---|---|
| Gln | Val | Lys | Leu | Leu | Glu | Ser | Gly | Gly | Thr | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |

|  | 20 |  |  |  |  | 25 |  |  |  |  | 30 |  |  |  |
|---|---|---|---|---|---|---|---|---|---|---|---|---|---|---|
| Ala | Met | Ser | Trp | Val | Arg | Gln | Ala | Pro | Gly | Lys | Gly | Leu | Glu | Trp | Val |
|  |  | 35 |  |  |  |  | 40 |  |  |  |  | 45 |  |  |  |
| Ser | Ala | Ile | Ser | Gly | Ser | Gly | Gly | Ser | Thr | Tyr | Tyr | Ala | Asp | Ser | Val |
|  | 50 |  |  |  |  | 55 |  |  |  |  |  | 60 |  |  |  |
| Lys | Gly | Leu | Phe | Thr | Ile | Ser | Arg | Asp | Asn | Ala | Lys | Asn | Thr | Leu | Tyr |
| 65 |  |  |  |  | 70 |  |  |  |  |  | 75 |  |  |  | 80 |
| Leu | Gln | Leu | Asn | Ser | Leu | Arg | Ala | Glu | Asp | Thr | Ala | Val | Tyr | Tyr | Cys |
|  |  |  |  | 85 |  |  |  |  | 90 |  |  |  |  | 95 |  |
| Ala | Arg | Ala | Glu | Leu | Gly | Gly | Leu | Met | Val | Ile | Val | Thr | Pro | Ser | Glu |
|  |  |  | 100 |  |  |  |  | 105 |  |  |  |  | 110 |  |  |
| Tyr | Trp | Gly | Gln | Gly | Thr | Leu | Val | Thr | Val | Ser |  |  |  |  |  |
|  |  | 115 |  |  |  |  | 120 |  |  |  |  |  |  |  |  |

( 2 ) INFORMATION FOR SEQ ID NO:39:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SpA1-30

( i x ) FEATURE:
        ( A ) NAME/KEY: CDS
        ( B ) LOCATION: 1..360

( x i ) SEQUENCE DESCRIPTION: SEQ ID NO:39:

| GTG | AAA | CTG | CTC | GAG | CAG | TCT | GGG | GGA | GGA | TTG | GTA | CAG | CCT | GGG | GGG | 48 |
| Val | Lys | Leu | Leu | Glu | Gln | Ser | Gly | Gly | Gly | Leu | Val | Gln | Pro | Gly | Gly |  |
| 1 |  |  |  | 5 |  |  |  |  | 10 |  |  |  |  | 15 |  |  |
| TCC | CTG | AGA | CTC | TCC | TGT | GCA | GCC | TCT | GGA | TTC | ACC | TTT | AGC | AGC | CAT | 96 |
| Ser | Leu | Arg | Leu | Ser | Cys | Ala | Ala | Ser | Gly | Phe | Thr | Phe | Ser | Ser | His |  |
|  |  |  | 20 |  |  |  |  | 25 |  |  |  |  | 30 |  |  |  |
| GCC | ATG | AGC | TGG | GTC | CGC | CAG | GCT | CCA | GGG | AGG | GGC | CTG | GAG | TGG | GTC | 144 |
| Ala | Met | Ser | Trp | Val | Arg | Gln | Ala | Pro | Gly | Arg | Gly | Leu | Glu | Trp | Val |  |
|  |  | 35 |  |  |  |  | 40 |  |  |  |  | 45 |  |  |  |  |
| TCA | GAT | ATT | AGT | GCC | AGT | GGT | GGT | AGC | ACA | TAT | TAT | GCA | GAC | TCC | GTG | 192 |
| Ser | Asp | Ile | Ser | Ala | Ser | Gly | Gly | Ser | Thr | Tyr | Tyr | Ala | Asp | Ser | Val |  |
|  | 50 |  |  |  |  | 55 |  |  |  |  |  | 60 |  |  |  |  |
| AAG | GGC | CGG | TTC | ACC | ATC | TCC | AGA | GAC | AAT | TCC | AAG | AAC | ACG | CTG | TAT | 240 |
| Lys | Gly | Arg | Phe | Thr | Ile | Ser | Arg | Asp | Asn | Ser | Lys | Asn | Thr | Leu | Tyr |  |
| 65 |  |  |  |  | 70 |  |  |  |  |  | 75 |  |  |  | 80 |  |
| TTG | CAA | ATG | AAC | AGC | CTG | AGA | GCC | GAA | GAC | ACG | GCC | TTA | TAT | TAC | TGT | 288 |
| Leu | Gln | Met | Asn | Ser | Leu | Arg | Ala | Glu | Asp | Thr | Ala | Leu | Tyr | Tyr | Cys |  |
|  |  |  |  | 85 |  |  |  |  | 90 |  |  |  |  | 95 |  |  |
| GCG | TCC | AAC | GGC | GCG | GGA | TGG | GGG | CTA | CCT | TCC | CTT | GAC | TAC | TGG | GGC | 336 |
| Ala | Ser | Asn | Gly | Ala | Gly | Trp | Gly | Leu | Pro | Ser | Leu | Asp | Tyr | Trp | Gly |  |
|  |  |  | 100 |  |  |  |  | 105 |  |  |  |  | 110 |  |  |  |
| CAG | GGA | ACC | CTG | GTC | ACC | GTC | TCC |  |  |  |  |  |  |  |  | 360 |
| Gln | Gly | Thr | Leu | Val | Thr | Val | Ser |  |  |  |  |  |  |  |  |  |
|  |  | 115 |  |  |  |  | 120 |  |  |  |  |  |  |  |  |  |

( 2 ) INFORMATION FOR SEQ ID NO:40:

( i ) SEQUENCE CHARACTERISTICS:
        ( A ) LENGTH: 120 amino acids
        ( B ) TYPE: amino acid
        ( D ) TOPOLOGY: linear (i) MOLECULE TYPE: protein (xi) SEQUENCE DESCRIPTION: SEQ ID NO:40:

| Val | Lys | Leu | Leu | Glu | Gln | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | His |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Arg | Gly | Leu | Glu | Trp | Val |
|---|---|---|---|---|---|---|---|---|---|---|---|---|---|---|---|
| | | 35 | | | | | 40 | | | | | 45 | | | |

| Ser | Asp | Ile | Ser | Ala | Ser | Gly | Gly | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Ser | Asn | Gly | Ala | Gly | Trp | Gly | Leu | Pro | Ser | Leu | Asp | Tyr | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser |
|---|---|---|---|---|---|---|---|
| | | 115 | | | | | 120 |

(2) INFORMATION FOR SEQ ID NO:41:

(i) SEQUENCE CHARACTERISTICS:
(A) LENGTH: 345 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: SpA1-29

(ix) FEATURE:
(A) NAME/KEY: CDS
(B) LOCATION: 1..345

(xi) SEQUENCE DESCRIPTION: SEQ ID NO:41:

| CAG | GTG | AAA | CTG | CTC | GAG | TCT | GGG | GGA | GGC | TTG | GTA | CAG | CCT | GGG | GGG | 48 |
|---|---|---|---|---|---|---|---|---|---|---|---|---|---|---|---|---|
| Gln | Val | Lys | Leu | Leu | Glu | Ser | Gly | Gly | Gly | Leu | Val | Gln | Pro | Gly | Gly | |
| 1 | | | | 5 | | | | | 10 | | | | | 15 | | |

| TCC | CTG | AGA | CTC | TCC | TGT | GCA | GCC | TCT | GGA | TTC | ACC | TTT | AGT | AAT | TAT | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Asn | Tyr | |
| | | | 20 | | | | | 25 | | | | | 30 | | | |

| GCC | ATG | AGC | TGG | GTC | CGC | CAG | GCT | CCA | GGG | AAG | GGG | CTG | GAG | TGG | GTC | 144 |
|---|---|---|---|---|---|---|---|---|---|---|---|---|---|---|---|---|
| Ala | Met | Ser | Trp | Val | Arg | Gln | Ala | Pro | Gly | Lys | Gly | Leu | Glu | Trp | Val | |
| | | 35 | | | | | 40 | | | | | 45 | | | | |

| TCA | GGT | ATT | AGT | GCC | AGT | GGT | GAT | ACC | ACA | TAC | TAC | GCA | GAC | TCC | GTG | 192 |
|---|---|---|---|---|---|---|---|---|---|---|---|---|---|---|---|---|
| Ser | Gly | Ile | Ser | Ala | Ser | Gly | Asp | Thr | Thr | Tyr | Tyr | Ala | Asp | Ser | Val | |
| | 50 | | | | | 55 | | | | | 60 | | | | | |

| AGG | GGC | CGG | TTC | GCC | ATC | TCC | AGA | GAC | AAT | TTC | AAG | AAC | ACG | CTG | TAT | 240 |
|---|---|---|---|---|---|---|---|---|---|---|---|---|---|---|---|---|
| Arg | Gly | Arg | Phe | Ala | Ile | Ser | Arg | Asp | Asn | Phe | Lys | Asn | Thr | Leu | Tyr | |
| 65 | | | | | 70 | | | | | 75 | | | | | 80 | |

| CTG | CAA | ATG | AAC | AGC | CTG | AGA | GCC | GAG | GAC | ACG | GCT | GTG | TAT | TAC | TGT | 288 |
|---|---|---|---|---|---|---|---|---|---|---|---|---|---|---|---|---|
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| GGT | AGA | GGA | TAC | AGC | TAC | CCT | GTC | TGG | GGG | CAA | GGG | ACC | ACG | GTC | ACC | 336 |
|---|---|---|---|---|---|---|---|---|---|---|---|---|---|---|---|---|
| Gly | Arg | Gly | Tyr | Ser | Tyr | Pro | Val | Trp | Gly | Gln | Gly | Thr | Thr | Val | Thr | |
| | | | 100 | | | | | 105 | | | | | 110 | | | |

| GTC | TCC | TCA | | | | | | | | | | | | | | 345 |
|---|---|---|---|---|---|---|---|---|---|---|---|---|---|---|---|---|
| Val | Ser | Ser | | | | | | | | | | | | | | |
| | | 115 | | | | | | | | | | | | | | |

( 2 ) INFORMATION FOR SEQ ID NO:42:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Gln Val Lys Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Glu Trp Val
        35                  40                  45
 Ser Gly Ile Ser Ala Ser Gly Asp Thr Thr Tyr Tyr Ala Asp Ser Val
        50                  55                  60
Arg Gly Arg Phe Ala Ile Ser Arg Asp Asn Phe Lys Asn Thr Leu Tyr
65                  70                  75                  80
Leu Gln Met Asn Ser Leu Arg Ala Glu Asp Thr Ala Val Tyr Tyr Cys
                85                  90                  95
Gly Arg Gly Tyr Ser Tyr Pro Val Trp Gly Gln Gly Thr Thr Val Thr
               100                 105                 110
Val Ser Ser
           115
```

( 2 ) INFORMATION FOR SEQ ID NO:43:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SpA1-14

( i x ) FEATURE:
        ( A ) NAME/KEY: CDS
        ( B ) LOCATION: 1..372

( x i ) SEQUENCE DESCRIPTION: SEQ ID NO:43:

```
CAG GTG AAA CTG CTC GAG TCT GGG GGA GGC TTA GTT CAG CCT GGG GGG      48
Gln Val Lys Leu Leu Glu Ser Gly Gly Gly Leu Val Gln Pro Gly Gly
 1               5                  10                  15
TCC CTG AGA CTC TCC TGT GCA GCC TCT GGA TTC ACC TTC AGT AGT TAC      96
Ser Leu Arg Leu Ser Cys Ala Ala Ser Gly Phe Thr Phe Ser Ser Tyr
            20                  25                  30
TGG ATG CAC TGG GTC CGC CAA GCT CCA GGG AAG GGC CTG GTG TGG GTC     144
Trp Met His Trp Val Arg Gln Ala Pro Gly Lys Gly Leu Val Trp Val
        35                  40                  45
TCA CGT ATT AAC ACT GAT GGG AGT AGA ACA AGT TAC GCG GAC TCC GTG     192
Ser Arg Ile Asn Thr Asp Gly Ser Arg Thr Ser Tyr Ala Asp Ser Val
        50                  55                  60
AAG GGC CGA TTC ACC ATC TCC AGA GAC AAC GCC AAG AAC ACC CTG TAT     240
Lys Gly Arg Phe Thr Ile Ser Arg Asp Asn Ala Lys Asn Thr Leu Tyr
65                  70                  75                  80
CTG CAA CTG AAC AGT CTG AGA GCC GAG GAC ACG GCT GTG TAT TAC TGT     288
Leu Gln Leu Asn Ser Leu Arg Ala Glu Asp Thr Ala Val Tyr Tyr Cys
                85                  90                  95
```

| GCA | AGA | GCC | GAA | TTG | CGA | CGG | CCC | AAT | GGT | TAT | GCT | AAC | CCC | CCT | CCT | 336 |
| Ala | Arg | Ala | Glu | Leu | Arg | Arg | Pro | Asn | Gly | Tyr | Ala | Asn | Pro | Pro | Pro | |
| | | | 100 | | | | | 105 | | | | | 110 | | | |

| GAG | TAC | TGG | GGC | CAG | GGA | ACC | CTG | GTC | ACC | GTC | TCC | 372 |
| Glu | Tyr | Trp | Gly | Gln | Gly | Thr | Leu | Val | Thr | Val | Ser | |
| | | 115 | | | | | 120 | | | | | |

(2) INFORMATION FOR SEQ ID NO:44:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:44:

| Gln | Val | Lys | Leu | Leu | Glu | Ser | Gly | Gly | Gly | Leu | Val | Gln | Pro | Gly | Gly |
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |

| Trp | Met | His | Trp | Val | Arg | Gln | Ala | Pro | Gly | Lys | Gly | Leu | Val | Trp | Val |
| | | 35 | | | | | 40 | | | | | 45 | | | |

| Ser | Arg | Ile | Asn | Thr | Asp | Gly | Ser | Arg | Thr | Ser | Tyr | Ala | Asp | Ser | Val |
| | 50 | | | | | 55 | | | | | 60 | | | | |

| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |

| Leu | Gln | Leu | Asn | Ser | Leu | Arg | Ala | Glu | Asp | Thr | Ala | Val | Tyr | Tyr | Cys |
| | | | | 85 | | | | | 90 | | | | | 95 | |

| Ala | Arg | Ala | Glu | Leu | Arg | Arg | Pro | Asn | Gly | Tyr | Ala | Asn | Pro | Pro | Pro |
| | | | 100 | | | | | 105 | | | | | 110 | | |

| Glu | Tyr | Trp | Gly | Gln | Gly | Thr | Leu | Val | Thr | Val | Ser |
| | | 115 | | | | | 120 | | | | |

(2) INFORMATION FOR SEQ ID NO:45:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: 0-19

(ix) FEATURE:
        (A) NAME/KEY: CDS
        (B) LOCATION: 1..339

(xi) SEQUENCE DESCRIPTION: SEQ ID NO:45:

| CAG | GTG | AAA | CTG | CTC | GAG | TCT | GGG | GGA | GGC | TTG | GTC | CAG | CCT | GGG | AGG | 48 |
| Gln | Val | Lys | Leu | Leu | Glu | Ser | Gly | Gly | Gly | Leu | Val | Gln | Pro | Gly | Arg | |
| 1 | | | | 5 | | | | | 10 | | | | | 15 | | |

| TCC | CTG | AGA | CTG | TCC | TGT | ACA | GCG | TCT | GGA | TTC | ACC | TTC | AGT | ACC | TTT | 96 |
| Ser | Leu | Arg | Leu | Ser | Cys | Thr | Ala | Ser | Gly | Phe | Thr | Phe | Ser | Thr | Phe | |
| | | | 20 | | | | | 25 | | | | | 30 | | | |

| GCC | ATG | AAC | TGG | GTC | CGC | CAG | GCT | CCA | GGC | AAG | GGC | CTG | GAG | TGG | GTC | 144 |
| Ala | Met | Asn | Trp | Val | Arg | Gln | Ala | Pro | Gly | Lys | Gly | Leu | Glu | Trp | Val | |
| | | 35 | | | | | 40 | | | | | 45 | | | | |

| GCA | GTT | GTA | TGG | TAT | GAT | GGA | ACT | ACT | AAG | TAC | TAT | GCA | GAC | TCC | GTG | 192 |
| Ala | Val | Val | Trp | Tyr | Asp | Gly | Thr | Thr | Lys | Tyr | Tyr | Ala | Asp | Ser | Val | |
| | 50 | | | | | 55 | | | | | 60 | | | | | |

| CAG | GGC | CGA | TTC | ACC | ATC | TCT | AGA | GAC | AAC | TCC | GAG | AAC | ACC | CTG | TAT | 240 |
| Gln | Gly | Arg | Phe | Thr | Ile | Ser | Arg | Asp | Asn | Ser | Glu | Asn | Thr | Leu | Tyr | |
| 65 | | | | | 70 | | | | | 75 | | | | | 80 | |

| CTG | CAA | ATG | AAC | AGC | CTG | AGA | GTC | GAG | GAC | ACG | GCT | GTC | TAT | TAC | TGT | 288 |
| Leu | Gln | Met | Asn | Ser | Leu | Arg | Val | Glu | Asp | Thr | Ala | Val | Tyr | Tyr | Cys | |
| | | | | 85 | | | | | 90 | | | | | 95 | | |

| GCG | AAA | GGA | TAC | CAG | TTG | TTG | CAT | GGG | CAG | ACC | CTG | GTC | ACC | GTC | TCC | 336 |
| Ala | Lys | Gly | Tyr | Gln | Leu | Leu | His | Gly | Gln | Thr | Leu | Val | Thr | Val | Ser | |
| | | | 100 | | | | | 105 | | | | | 110 | | | |

| TCA | | | | | | | | | | | | | | | | 339 |
| Ser | | | | | | | | | | | | | | | | |

( 2 ) INFORMATION FOR SEQ ID NO:46:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

| Gln | Val | Lys | Leu | Leu | Glu | Ser | Gly | Gly | Gly | Leu | Val | Gln | Pro | Gly | Arg |
| 1 | | | | 5 | | | | | 10 | | | | | 15 | |

| Ser | Leu | Arg | Leu | Ser | Cys | Thr | Ala | Ser | Gly | Phe | Thr | Phe | Ser | Thr | Phe |
| | | | 20 | | | | | 25 | | | | | 30 | | |

| Ala | Met | Asn | Trp | Val | Arg | Gln | Ala | Pro | Gly | Lys | Gly | Leu | Glu | Trp | Val |
| | | 35 | | | | | 40 | | | | | 45 | | | |

| Ala | Val | Val | Trp | Tyr | Asp | Gly | Thr | Thr | Lys | Tyr | Tyr | Ala | Asp | Ser | Val |
| | 50 | | | | | 55 | | | | | 60 | | | | |

| Gln | Gly | Arg | Phe | Thr | Ile | Ser | Arg | Asp | Asn | Ser | Glu | Asn | Thr | Leu | Tyr |
| 65 | | | | | 70 | | | | | 75 | | | | | 80 |

| Leu | Gln | Met | Asn | Ser | Leu | Arg | Val | Glu | Asp | Thr | Ala | Val | Tyr | Tyr | Cys |
| | | | | 85 | | | | | 90 | | | | | 95 | |

| Ala | Lys | Gly | Tyr | Gln | Leu | Leu | His | Gly | Gln | Thr | Leu | Val | Thr | Val | Ser |
| | | | 100 | | | | | 105 | | | | | 110 | | |

Ser ( 2 ) INFORMATION FOR SEQ ID NO:47:

( i ) SEQUENCE CHARACTERISTICS:
        ( A ) LENGTH: 294 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: VH26C ( i x ) FEATURE:
        ( A ) NAME/KEY: CDS
        ( B ) LOCATION: 1..294

( x i ) SEQUENCE DESCRIPTION: SEQ ID NO:47:

| GAG | GTG | CAG | CTG | TTG | GAG | TCT | GGG | GGA | GGC | TTG | GTA | CAG | CCT | GGG | GGG | 48 |
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |

| TCC | CTG | AGA | CTC | TCC | TGT | GCA | GCC | TCT | GGA | TTC | ACC | TTT | AGC | AGC | TAT | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| GCC | ATG | AGC | TGG | GTC | CGC | CAG | GCT | CCA | GGG | AAG | GGG | CTG | GAG | TGG | GTC | 144 |
| Ala | Met | Ser | Trp | Val | Arg | Gln | Ala | Pro | Gly | Lys | Gly | Leu | Glu | Trp | Val | |

|     |     |     |     |     | 35  |     |     |     |     | 40  |     |     |     |     | 45  |     |     |     |
|-----|-----|-----|-----|-----|-----|-----|-----|-----|-----|-----|-----|-----|-----|-----|-----|-----|-----|-----|
| TCA | GCT | ATT | AGT | GGT | AGT | GGT | GGT | AGC | ACA | TAC | TAC | GGA | GAC | TCC | GTG |     |     | 192 |
| Ser | Ala | Ile | Ser | Gly | Ser | Gly | Gly | Ser | Thr | Tyr | Tyr | Gly | Asp | Ser | Val |     |     |     |
|     | 50  |     |     |     | 55  |     |     |     |     | 60  |     |     |     |     |     |     |     |     |
| AAG | GGC | CGG | TTC | ACC | ATC | TCC | AGA | GAC | ATT | TCC | AAG | AAC | ACG | CTG | TAT |     |     | 240 |
| Lys | Gly | Arg | Phe | Thr | Ile | Ser | Arg | Asp | Ile | Ser | Lys | Asn | Thr | Leu | Tyr |     |     |     |
| 65  |     |     |     |     | 70  |     |     |     |     | 75  |     |     |     |     | 80  |     |     |     |
| CTG | CAA | ATG | AAC | AGC | CTG | AGA | GCC | GAG | GAC | ACG | GCC | GTA | TAT | TAC | TGT |     |     | 288 |
| Leu | Gln | Met | Asn | Ser | Leu | Arg | Ala | Glu | Asp | Thr | Ala | Val | Tyr | Tyr | Cys |     |     |     |
|     |     |     |     | 85  |     |     |     |     | 90  |     |     |     |     | 95  |     |     |     |     |
| GCG | AAA |     |     |     |     |     |     |     |     |     |     |     |     |     |     |     |     | 294 |
| Ala | Lys |     |     |     |     |     |     |     |     |     |     |     |     |     |     |     |     |     |

(2) INFORMATION FOR SEQ ID NO:48:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:48:

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Leu | Arg | Leu | Ser | Cys | Ala | Ala | Ser | Gly | Phe | Thr | Phe | Ser | Ser | Tyr |
|     |     |     | 20  |     |     |     |     | 25  |     |     |     |     | 30  |     |     |
| Ala | Met | Ser | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |
| Ser | Ala | Ile | Ser | Gly | Ser | Gly | Gly | Ser | Thr | Tyr | Tyr | Gly | Asp | Ser | Val |
|     | 50  |     |     |     | 55  |     |     |     |     | 60  |     |     |     |     |     |
| Lys | Gly | Arg | Phe | Thr | Ile | Ser | Arg | Asp | Ile | Ser | Lys | Asn | Thr | Leu | Tyr |
| 65  |     |     |     |     | 70  |     |     |     |     | 75  |     |     |     |     | 80  |
| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

Ala Lys (2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: DomD 5'

(ix) FEATURE:
        (A) NAME/KEY: CDS
        (B) LOCATION: 1..25

(xi) SEQUENCE DESCRIPTION: SEQ ID NO:49:

GACTCTCAAG ATCTAAAAGC TGATG        25

(2) INFORMATION FOR SEQ ID NO:50:

(i) SEQUENCE CHARACTERISTICS:
        (A) LENGTH: 42 base pairs
        (B) TYPE: nucleic acid
        (C) STRANDEDNESS: single
        (D) TOPOLOGY: linear -continued ( i i ) MOLECULE TYPE: DNA (genomic)

( v i i ) IMMEDIATE SOURCE:
( B ) CLONE: DomDAS 3'

( i x ) FEATURE:
( A ) NAME/KEY: CDS
( B ) LOCATION: 1..42

( x i ) SEQUENCE DESCRIPTION: SEQ ID NO:50:

TTTGTGGATC CTTCTTCTTG AGCTCCTTGG TACCTTTCGG TG 42

( 2 ) INFORMATION FOR SEQ ID NO:51:

( i ) SEQUENCE CHARACTERISTICS:
( A ) LENGTH: 62 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( B ) CLONE: SpA Domain D VH3 Ig Binding Region ( i x ) FEATURE:
( A ) NAME/KEY: Peptide
( B ) LOCATION: 1..62

( x i ) SEQUENCE DESCRIPTION: SEQ ID NO:51:

Ala Asp Ala Gln Gln Asn Asn Phe Asn Lys Asp Gln Gln Ser Ala Phe
1 5 10 15

Tyr Glu Ile Leu Asn Met Pro Asn Leu Asn Glu Ala Gln Arg Asn Gly
20 25 30

Glu Phe Ile Gln Ser Thr Lys Asp Asp Pro Ser Gln Ser Thr Asn Val
35 40 45

Leu Gly Glu Ala Lys Lys Leu Asn Glu Ser Gln Ala Pro Lys
50 55 60